(12) United States Patent
Kellenberger et al.

(10) Patent No.: US 8,410,065 B2
(45) Date of Patent: Apr. 2, 2013

(54) MACROLIDES AND THEIR USE

(75) Inventors: Johannes Laurenz Kellenberger, Riehen (CH); Jürg Dreier, Witterswil (CH); Stefan Bernhard Reinelt, Weil am Rhein (DE)

(73) Assignee: Basilea Pharmaceutica AG, Basel (CH)

( * ) Notice: Subject to any disclaimer, the term of this patent is extended or adjusted under 35 U.S.C. 154(b) by 22 days.

(21) Appl. No.: 12/864,921

(22) PCT Filed: Feb. 9, 2009

(86) PCT No.: PCT/EP2009/051441
§ 371 (c)(1),
(2), (4) Date: Nov. 11, 2010

(87) PCT Pub. No.: WO2009/106419
PCT Pub. Date: Sep. 3, 2009

(65) Prior Publication Data
US 2011/0053876 A1 Mar. 3, 2011

(30) Foreign Application Priority Data
Feb. 8, 2008 (EP) ..................................... 08101438

(51) Int. Cl.
*A61K 31/70* (2006.01)
*C07H 17/08* (2006.01)
(52) U.S. Cl. .............. 514/29; 536/7.2; 536/7.3; 536/7.4
(58) Field of Classification Search .................... 536/7.2, 536/7.3, 7.4
See application file for complete search history.

(56) References Cited

U.S. PATENT DOCUMENTS

| 6,720,308 | B1 | 4/2004 | Vo et al. |
| 2004/0038915 | A1 | 2/2004 | Vo et al. |

FOREIGN PATENT DOCUMENTS

| WO | 97/42205 | 11/1997 |
| WO | 02/16380 | 2/2002 |
| WO | 03/004509 | 1/2003 |
| WO | 03/024986 | 3/2003 |
| WO | 03/042228 | 5/2003 |
| WO | 03/072588 | 9/2003 |
| WO | 2004/013153 | 2/2004 |
| WO | 2004016634 | 2/2004 |
| WO | 2005/067919 | 7/2005 |
| WO | 2006084410 | 8/2006 |
| WO | 2007/129646 | 11/2007 |

OTHER PUBLICATIONS

The International Search Report and Written Opinion by the International Searching Authority, issued on Jul. 6, 2009, in the PCT application No. PCT/EP2009/051441.
Hunziker et al., "Novel ketolide antibiotics with a fused five-membered lactone ring-synthesis, physicochemical and antimicrobial properties," Bioorg Med Chem. Jul. 1, 2004;12(13):3503-19.
Lipworth, "Phosphodiesterase-4 inhibitors for asthma and chronic obstructive pulmonary disease," The Lancet, vol. 365, Issue 9454, pp. 167-175.
Giembycz, "Life after PDE4: overcoming adverse events with dual-specificity phosphodiesterase inhibitors," Curr Pharmacol. Jun. 2005;5(3):238-44.
McEwan et al., "Chemoresistant KM12C Colon Cancer Cells Are Addicted to Low Cyclic AMP Levels in a Phosphodiesterase 4—Regulated Compartment via Effects on Phosphoinositide 3-Kinase," Cancer Res 2007; 67: (11). Jun. 1, 2007.
Odingo, "Inhibitors of PDE4: a review of recent patent literature," Expert Opinion on Therapeutic Patents, Jul. 2005, vol. 15, No. 7, pp. 773-787.
Hendrix et al., "9 Phosphodiesterase Inhibitors: A Chemogenomic View," Chemogenomics in Drug Discovery: A Medicinal Chemistry Perspective, Oct. 2004, pp. 243-288.
Tanikawa et al., "Synthesis and antibacterial activity of a novel series of acylides: 3-O-(3-pyridyl)acetylerythromycin A derivatives," J Med Chem. Jun. 19, 2003;46(13):2706-15.
Heggelund et al., "Preparation of cyclic 2',3'-carbamate derivatives of erythromycin macrolide antibiotics," Bioorg Med Chem. May 1, 2007;15(9):3266-77.
Labro, "Anti-inflammatory activity of macrolides: a new therapeutic potential?" Journal of Antimicrobial Chemotherapy vol. 41, Issuesuppl 2 pp. 37-46, 1998.
Baker et al., "Modification of macrolide antibiotics. Synthesis of 11-deoxy-11-(carboxyamino)-6-O-methylerythromycin A 11,12-(cyclic esters) via an intramolecular Michael reaction of O-carbamates with an alpha,beta-unsaturated ketone," J. Org. Chem., 1988, 53 (10), pp. 2340-2345.
Lartey et al., "Synthesis of 4-Deoxy Motilides: Identification of a Potent and Orally Active Prokinetic Drug Candidate," J. Med. Chem., 1995, 38 (10), pp. 1793-1798.
11. Nishimura et al., "Bis-3-oxo-λ5-phosphole: Isolation, Structural Analyses, and Synthesis of Phosphorus-ylide Containing Conjugated Heterocycle," J. Org. Chem., 2010, 75 (11), pp. 3875-3877.
12. Elliott et al., "Anhydrolide Macrolides. 1. Synthesis and Antibacterial Activity of 2,3-Anhydro-6-O-methyl 11,12-Carbamate Erythromycin A Analogues," J. Med. Chem., 1998, 41 (10), pp. 1651-1659.
13. Agouridas et al., "Synthesis and antibacterial activity of ketolides (6-O-methyl-3-oxoerythromycin derivatives): a new class of antibacterials highly potent against macrolide-resistant and -susceptible respiratory pathogens," J. Med. Chem. Oct. 8, 1998;41(21):4080-100.
14. Torphy et al., "Stimulation of beta adrenoceptors in a human monocyte cell line (U937) up-regulates cyclic AMP-specific phosphodiesterase activity," JPET Dec. 1992 vol. 263 No. 3 1195-1205.

*Primary Examiner* — Elli Peselev

(57) ABSTRACT

The invention relates to antibiotic macrolides of formula (I),

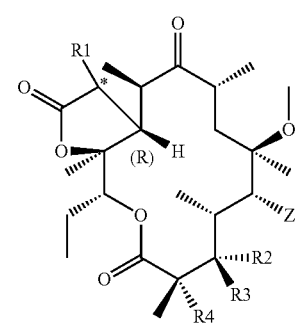

(I)

which have improved anti-inflammatory activity mediated through inhibition of phosphodiesterase 4 (PDE4) useful for the treatment and/or prevention of inflammatory, allergic and proliferative diseases.

42 Claims, No Drawings

MACROLIDES AND THEIR USE

This application is a National Stage Application of PCT/EP2009/051441, filed Feb. 9, 2009, which claims priority from European Patent Application 08101438.3 filed on Feb. 8, 2008. The priority of both said PCT and European Patent Application is claimed.

The invention relates to novel macrolide compounds, the use of said compounds as medicaments, in particular for the treatment or prevention of inflammatory and allergic diseases, pharmaceutical compositions containing said compounds and to processes for their preparation. The invention relates in particular to macrolide compounds with anti-inflammatory activity mediated primarily through inhibition of phosphodiesterase 4 (PDE4) which makes them useful for the treatment and/or prevention of inflammatory and allergic diseases such as chronic obstructive pulmonary disease (COPD), asthma, rheumatoid arthritis, atopic dermatitis or inflammatory bowel disease or proliferative diseases such as cancer.

Cyclic adenosine monophosphate (cAMP) is a key second messenger in cells. Increased levels of cyclic AMP are known to suppress cellular responses in various types of inflammatory and immune cells including lymphocytes, monocytes, macrophages, neutrophils, eosinophils, basophils and lung epithelial cells. Intracellular concentrations of cAMP are regulated by adenylyl cyclase and by cyclic nucleotide phosphodiesterases (PDEs). PDEs are a family of enzymes that inactivate cyclic nucleotides cAMP and cGMP through hydrolysis to AMP and GMP. The cAMP-specific enzyme PDE4 is the predominant enzyme in pro-inflammatory cells. PDE4 has been shown to be involved in inflammatory processes (cf. e.g. Lipworth B. J., Lancet (2005) 365, p. 167 or Giembycz M. A., Curr. Opin. Pharmacol. (2005), 5, p. 238). Therefore, inhibitors of PDE4 are useful in the treatment and/or prophylaxis of inflammatory and allergic diseases such as asthma, chronic bronchitis, emphysema, atopic dermatitis, urticaria allergic rhinitis, allergic conjunctivitis, psoriasis, rheumatoid arthritis, chronic obstructive pulmonary disease (COPD), septic shock, ulcerative colitis, Crohn's disease, adult respiratory distress syndrome and multiple sclerosis. PDE4 inhibitors are also useful for the treatment of proliferative diseases such as human cancer (cf e.g. Cancer Research, 2007, 67, p. 5248). Numerous PDE4 inhibitors have been disclosed in the literature. (see for example J. O. Odingo, Expert. Opin. Ther. Patents, 2005, 15(7), 773; M. Hendrix, C. Kallus, Methods and Principles in Medicinal Chemistry (2004), Vol. 22 (Chemogenomics in Drug Discovery), 243-288 (Wiley-VCH)). Many of the known PDE4 inhibitors show dose-limiting side-effects such as emesis and headache.

Erythromycin derivatives having a five-membered lactone ring fused to the 11,12-positions of the macrolactone ring have been disclosed in e.g. WO 02/16380, WO 03/004509, WO 03/042228, WO 03/072588, WO 03/024986, US 2004/0038915 and in WO2005067919. Documents WO 02/16380, WO 03/072588, WO 03/024986 and US 2004/0038915 describe exclusively so-called ketolides having a carbonyl group at position 3 of the erythromycin scaffold. WO 03/042228, WO 03/004509 and WO2005/067919 disclose macrolide derivatives with a 11,12 lactone ring fused to the 11,12-positions and a cladinose sugar substituent at position 3 of the erythromycin scaffold.

Erythromycin derivatives with a double bond at positions 2,3 of the erythromycin scaffold, so-called anhydrolides, have been disclosed e.g. in WO97/42205 and U.S. Pat. No. 6,720,308. Compounds with a hydroxyl group in position 3 of the erythromycin scaffold are found as intermediates in the synthesis of various compounds mentioned above and are also disclosed in e.g. WO2004/013153. Formation of 3-acyl-derivatives is described in e.g. J. Med. Chem. 2003, 46, 2706.

Most of the molecules described in the references cited above have anti-infective activity. However, if erythromycin derivatives are foreseen for chronic treatment of diseases not caused by pathogenic bacteria, it is desirable to have compounds devoid of anti-infective activity in order to avoid the development of antibiotic-resistant bacteria. It has been reported that modifications of the desosamine moiety can lead to a loss of antibacterial activity. Various modifications of the desosamine sugar moiety of erythromycin derivatives have been described in the literature as exemplified by the following publications: WO2007/129646, WO2004/013153 and Bioorg. Med. Chem. 2007, 15, 3266.

Erythromycin-derived macrolides have also been reported to possess anti-inflammatory activity (e.g. Journal of Antimicrobial Chemotherapy, 1998, 41, Suppl. B, 37-46). All macrolide compounds described in the above-mentioned documents have been disclosed as useful for the treatment of bacterial infections. Furthermore, erythromycin-derived macrolides are known to accumulate in inflammatory cells.

Surprisingly, it has now been found that certain macrolide compounds having a five-membered lactone ring fused to the erythromycin scaffold and being substituted with specific side chains, without having significant antibacterial activity, inhibit phosphodiesterases and in particular selectively inhibit PDE4, a newly found activity not described so far for this kind of molecules. These macrolides are therefore useful for the treatment and/or prevention of inflammatory and allergic diseases as well as proliferative diseases such as e.g. cancer. The molecules described herein are structurally distinct from currently known PDE4 inhibitors and therefore have the potential to overcome the above-mentioned side effects.

The present invention accordingly relates to macrolide compounds of formula I:

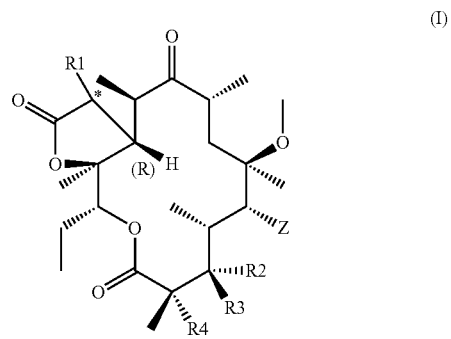

wherein
R1 is a residue -Y-X-Q;
Y is S, SO or $SO_2$;
X is a bond or a linear group consisting of hydrogen atoms and 1 to 9 atoms selected from C, N, O and S, of which up to 2 atoms can be N and one atom can be O or S, one carbon atom can appear as a CO group and the sulphur atom can appear as an $SO_2$ group and two adjacent C atoms can be present as —CH═CH— or —C≡C— and which group X is unsubstituted or is substituted with —COO—W or —CONH—W;
Q is W, a residue —V-A1-L-A2-W or, if X does not represent a bond, may also be —NR10R11

V is an optionally substituted divalent aromatic or heterocyclic group;

W is optionally substituted aryl or heterocyclyl; or in a group —V-A1-L-A2-W, wherein at least one of the groups A1, L or A2 is present, can also be a monovalent substituted or unsubstituted, saturated or unsaturated linear group consisting of hydrogen and 1 to 5 atoms C, N, O and/or S of which one carbon can appear as a CO group one sulphur atom can appear as an $SO_2$ group, A1 and A2 are, independently of each other, either absent or a $C_1$-$C_4$alkylene group;

L is a single bond, —O—, —S—, —$SO_2$—, —NH—, —CO—, —(CO)O—, —O(OC)—, —(CO)NH—, —NH(CO)—, —($SO_2$)NH—, —HN($SO_2$)—, —HN(CO)NH—, —O(CO)NH—, —NH(CO)O—, or can also be absent if A1 and/or A2 are present;

R2 is OR2a or

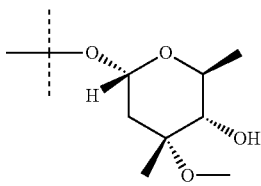

wherein

represents the linking bond;

R2a is hydrogen, acetyl, —(C=O)$CH_2$NR2bR2c, or —(C=O)$CH_2$$CH_2$NR2bR2c;

R2b and R2c independently of each other, are hydrogen or C1-C6 alkyl which can be substituted or unsubstituted and wherein up to two atoms can be N, O or S and one carbon atom can appear as C=O, taken together with the nitrogen atom to which they are linked, form a 4-7 membered-ring of which up to two atoms can be N, O or S and one carbon can appear as C=O;

R3 is hydrogen or

R2 and R3 taken together with the carbon atom to which they are linked, represent a C=O group;

R4 is hydrogen or

R2 and R4 taken together with the bond between the carbon atoms to which they are linked, represent a double bond between said carbon atoms;

Z is

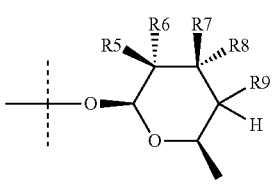

wherein

represents the linking bond;

R5 is hydrogen or —OR5a or —NR5bR5c;

R6 is hydrogen or —OR6a or —NR6bR6c; or

R5 and R6 taken together with the carbon atom to which they are linked, represent a C=O group;

R7 is hydrogen or —OR7a or —NR7bR7c;

R8 is hydrogen or —OR8a or —NR8bR8c; or

R7 and R8 taken together with the carbon atom to which they are linked, represent a C=O group; or one of R5 and R6 taken together with one of R7 and R8 represent a group of formula —NR56(CO)O— or —O(CO)NR78

R9 is hydrogen or

R8 and R9 taken together with the bond between the carbon atoms to which they are linked, represent a double bond between said carbon atoms;

R5a, R6a,

R7a and R8a, independently of each other, are hydrogen or C1-C6 alkyl which can be substituted or unsubstituted and wherein one or more single bonds can be replaced by double and/or triple bonds and where one carbon atom can appear as C=O and up to two atoms can be N, O or S;

R56 and R78 are hydrogen or C1-C6 alkyl;

R5b, R5c,

R6b, R6c,

R7b, R7c,

R8b and R8c independently of one another, are hydrogen, C1-C6alkyl which can be substituted or unsubstituted and up to two atoms can be N, O or S and where one carbon atom can appear as C=O, or —(C=O)heterocyclyl or, taken together with the nitrogen atom to which they are linked, form a 4-7 membered-ring of which up to two atoms can be N, O or S and one carbon can appear as C=O;

R10 and R11 are independently selected from hydrogen, methyl; from optionally substituted groups selected from aryl; aralkyl; heterocyclyl and heterocyclylalkyl groups, and one of R10 and R11 can also be a group -L-A2-W; and

* indicates a chiral centre which is in the (R) or (S) form;

provided that

Z is not a group of formula

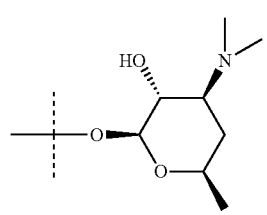

wherein

represents the linking bond.

For the purposes of the present invention the term "macrolide compound" is understood to include the separate stereomeric forms of the compounds as well as diastereomeric mixtures.

Furthermore, the term "macrolide compound" is understood in the present invention to include pharmaceutically acceptable salts and N-oxides of compounds of formula (I), as well as in vivo cleavable esters.

The compounds of the invention exhibit substantial inhibitory activity towards phosphodiesterases (PDEs), in particular towards PDE4, in particular human phosphodiesterases (PDEs and PDE4, which has been shown to be involved in inflammatory processes (cf. e.g. Lipworth B. J., Lancet (2005) 365, p. 167 or Giembycz M. A., Curr. Opin. Pharmacol. (2005), 5, p. 238). This is shown in the examples. The use of the compounds according to the present invention for the treatment of diseases and disorders in a subject, selected from animals like e.g. mammals, and particularly humans which can be ameliorated or relieved by inhibition of phosphodiesterases, in particular phosphodiesterase 4 (PDE4) is therefore a further aspect of the present invention. Based on this activity the present compounds are particularly useful for the prevention and/or treatment of inflammatory diseases as well as for the treatment and/or prevention of allergic diseases and for the prevention and/or treatment of diseases associated with uncontrolled cellular growth, proliferation and/or survival in such subjects, e.g. cancer. A use for humans is preferred.

Particularly important examples of such diseases are chronic obstructive pulmonary disease (COPD), asthma, rheumatoid arthritis, atopic dermatitis or inflammatory bowel disease and said cancer diseases.

For the purposes of the present invention the terms "aromatic group" and "aryl" refer to aromatic groups with one or more preferably 6-membered nuclei and having from 6 to 14 carbon atoms. Examples are in particular phenyl, naphthyl, anthryl and phenanthryl. These groups may be further substituted with 1, 2, 3 or 4 substituents selected from, for example, alkyl such as defined hereinafter, lower alkoxy such as $C_1$-$C_4$alkoxy like methoxy, ethoxy, propyloxy or n-butoxy, $C_3$-$C_7$cycloalkyloxy or $C_3$-$C_7$cycloalkyl-$C_1$-$C_4$alkoxy like cyclopentyloxy, cyclopropylmethyloxy, halogen such as defined hereinafter, halogen substituted alkyl groups such as difluoromethyl or trifluoromethyl, trichloroethyl, halogen substituted alkoxy groups such as difluoromethoxy, cyano, nitro, amino, alkylamino, dialkylamino, alkylthio, mercapto, hydroxy, carbamoyl, carboxyl group. In case more than one substituent is attached to the aryl group, these substituents can be identical or different from each other. Also encompassed by the scope of the present invention are different possible regioisomers (constitution isomers) of a specific group, for example "dimethoxy-phenyl" means that both methoxy substituents may be attached to the phenyl ring in the 2,3-position, the 2,4-position, the 2,5-position, the 2,6-position, the 3,4-position, the 3,5-position and the 3,6-position.

As used herein the term "heterocyclic group" or "heterocyclyl" refers to an unsaturated or saturated, unsubstituted or substituted 5- to 10-membered (mono- or bicyclic) heterocyclic ring system containing at least one hetero atom selected from the group consisting of sulfur, oxygen, and, preferably, nitrogen. Exemplary heterocyclic substituents include, but are not limited to, for example, the following groups: piperidinyl, morpholinyl, 2-, 3- or 4-pyridyl, pyrrolidinyl, piperazinyl, 1H-pyrazol-1-yl, 1H-imidazol-1-yl, 1H-imidazol-2-yl, pyrazinyl, pyrimidyl, pyridazinyl, pyrazolyl, triazinyl, thiazolyl, thiadiazolyl, oxadiazolyl, triazolyl, e.g. 1H-[1,2,4]-triazol-1-yl, 1H-tetrazolyl, 2H-tetrazolyl; thienyl, furyl (2-furanyl or 3-furanyl), 1H-azepinyl, tetrahydrothiophenyl, 3H-1,2,3-oxathiazolyl, 1,2,3-oxadiazolyl, 1,2,5-oxadithiolyl, isoxazo lyl, isothiazo lyl, 4H-1,2,4-oxadiazinyl, 1,2,5-oxathiazinyl, 1,2,3,5-oxathiadiazinyl, 1,3,4-thiadiazepinyl, 1,2,5,6-oxatriazepinyl, oxazolidinyl, tetrahydrothienyl, and the like, or condensed heterocyclic ring systems such as quinolinyl, e.g. quinolin-8-yl, quinolin-5-yl, quinolin-2-yl, quinolin-6-yl, quinolin-3-yl, isoquinolinyl (6-isoquinolinyl), quinazolinyl, 1H-benztriazolyl, 1H-imidazo[4,5-c]pyridinyl, 5H-imidazo[4,5-c]pyridinyl, 1H-imidazo[4,5-b]pyridin-1-yl, 3H-imidazo[4,5-b]pyridin-3-yl, 1H-pyrazolo[3,4-b]pyridinyl, 1,2,3,4-tetrahydro-quinolinyl, 1,2,3,4-tetrahydro-isoquinolinyl, thieno[2,3-b]pyridinyl, benzothiazolyl (e.g. 2-benzothiazolyl), 1H-benzoimidazolyl, 1H-indolyl, 1,2,3,4-tetrahydroquinolinyl, purinyl, e.g. 9H-purin-9-yl, 6-amino-9H-purin-9-yl, 2,6-diamino-9H-purin-9-yl, 1H-purin-6-yl, 1H-2,3-dihydroindol-1-yl, 2,1,3-benzoxadiazol-5-yl, 2,1,3-benzoxadiazol-4-yl, 1,3-benzodioxol-5-yl, 2,3-benzoxazolinyl, 1,2-dihydro-oxazolo[5,4-c]pyridinyl, 6-quinoxalinyl, 2-benzo[b]thien-3-yl, 3,4-dihydro-1H-2-oxo-quinolin-6-yl.

The heterocyclyl groups may be further substituted by one or more substituents. Such substituents include, for example, alkyl groups such as defined hereinafter, lower alkoxy such as $C_1$-$C_4$alkoxy like methoxy, ethoxy, propyloxy or n-butoxy, $C_3$-$C_7$cycloalkyloxy or $C_3$-$C_7$cycloalkyl-$C_1$-$C_4$alkoxy like cyclopentyloxy, cyclopropylmethyoxy, halogen such as defined hereinafter, halogen substituted alkyl groups such as trifluoromethyl, trichloroethyl; halogen substituted alkoxy groups such as difluoromethloxy; cyano, nitro, amino, alkylamino, dialkylamino, alkylthio, mercapto, hydroxy, carbamoyl, carboxyl, an oxo group. In case more than one substituent is attached to the heterocyclyl group, these substituents can be identical or different from each other. Different regioisomers are also included within the scope of the present definition, for example "dimethylpyridyl" means that both methyl substituents may be attached to the pyridyl at all chemically possible positions. For example both methyl substituents may be attached to the 2-pyridyl in the 3,4-position, the 4,5-position, the 5,6-position, the 3,5-position, the 3,6-position, and the 4,6-position. Both methyl substituents may be attached to the 3-pyridyl in the 2,4-position, the 2,5-position, the 2,6-position, the 4,5-position, the 4,6-position, and the 5,6-position. Both methyl substituents may be attached to the 4-pyridyl in the 2,3-position, the 2,5-position, the 2,6-position, and the 3,5-position.

Especially preferred substituents for the heterocyclyl groups are alkyl, alkoxy, oxo, halogen, amino, alkylamino or dialkylamino, wherein alkyl and alkoxy are as defined hereinabove.

Examples of preferred substituted heterocyclic rings are 1H-pyrimidin-2,4-dione, 1H,3H-pyrimidin-2,4-dione-5-methyl, 1H-pyrimidin-4-amino-2-on, 6-amino-9H-purin, 6-dimethylamino-9H-purin, 2,6-diamino-9H-purin, 6-amino-8-[(3-pyridinylmethyl)amino]-9H-purin, 4-amino-imidazo[4,5-c]pyridine, 4-methoxy-imidazo[4,5-c]pyridine, 1-ethyl-pyrazolo[3,4-b]pyridine, 4-phenyl-1H-pyrazol, 3-(pyridin-3-yl)-1H-pyrazol, 3-(pyridin-4-yl)-1H-pyrazol-1-yl, 3-(pyridin-3-yl)-1H-imidazol-1-yl, 3-(pyridin-4-yl)-1H- imidazol-1-yl, 3-(pyridin-3-yl)-1H-[1,2,4]triazol, 3-(pyridin-4-yl)-1H-[1,2,4]triazol and 2-oxo-1,2,3,4-tetrahydroquinoline.

As used herein the term "alkyl" refers to branched or straight chain saturated hydrocarbon groups having preferably 1 to 6 carbon atoms. Such groups are for example methyl, ethyl, n-propyl, isopropyl, tertiary butyl, pentyl, hexyl and the like. Such alkyl groups may be further substituted with one or more substituents selected from, for example, lower alkoxy such as $C_1$-$C_4$alkoxy like methoxy, ethoxy, propyloxy or n-butoxy, $C_3$-$C_7$cycloalkyloxy or $C_3$-$C_7$cycloalkyl-$C_1$-$C_4$alkoxy like cyclopentyloxy, cyclopropylmethyloxy, halogen such as defined below, halogen substituted alkyl groups such as difluoromethyl or trifluoromethyl, trichloroethyl, cyano, nitro, amino, alkylamino, dialkylamino, alkylthio, mercapto, hydroxy, carbamoyl, carboxyl, or oxo. If more than one substituent are present, these can be either identical or different from each other.

The term aliphatic group refers to branched or preferably straight chain hydrocarbon groups having preferably 1 to 6 carbon atoms, which can be saturated or unsaturated. Examples include those mentioned for alkyl, vinyl, n-propenyl, n-propinyl, butenyl groups, butadienyl, pentenyl groups, and the like.

The term "halogen" refers to fluorine, chlorine, bromine or iodine preferably fluorine and chlorine.

In the combinations "heterocyclylalkyl" and "aralkyl" the single parts "heterocyclyl", "ar" i.e. aryl, and "alkyl" have the meanings indicated above.

The term $C_1$-$C_4$alkylene group refers e.g. to methylene, ethylene, n-propylene, iso-propylene or n-butylene.

R1 is a residue of formula -Y-X-Q.

In this formula Y may generally be S, SO or $SO_2$; preferred are S and $SO_2$, in particular S.

X is either a bond; i.e. is "absent", or a linear group consisting of hydrogen atoms and up to 9 atoms selected from C, N, O and/or S, of which up to 2 atoms can be N and one atom can be O or S, one carbon atom can appear as a CO group and the sulphur atom can appear as an $SO_2$ group. Two adjacent C atoms can also be present as —CH═CH— or —C≡C—. The group X can be unsubstituted or is substituted with a substituent of formula —COO—W or —CONH—W, wherein W has the meaning defined herein. As already indicated, the spacer group X with up to 9 atoms may carry additional hydrogen atoms to saturate a C atom to form a methylene group or to saturate a N atom to form an amino group. Preferably, this spacer consists of 2 to 5 atoms selected from C, N, O and/or S.

Preferred groups X are:
$(CH_2)_n$, $(CH_2)_mOCH_2$, $(CH_2)_2NCH_3(CH_2)_2$, $CH_2CH_2NH$, $(CH_2)_pCOO$, $(CH_2)_pCONH$; $O(CH_2)_p$ or $HN(CH_2)_p$, where n and p are 1, 2 or 3 and m is 0 or preferably 1, 2 or 3 and which are linked with the group Y via a carbon atom.

Particularly preferred groups X are 1,2-ethylene, n-propylene or iso-propylene and $O(CH_2)_p$ or $HN(CH_2)_p$, where p is 2 or 3, preferably 2.

Suitable combinations of Y and X are e.g as follows:
For Y═S, X is 1,2-ethylene, 1,2- and 1,3-propylene, $CH_2CO$, $CH_2COCH_2$, $CH_2CONR$, $CH_2CONRCH_2$, $CH_2CONRCH_2CH_2$, $CH_2CH_2O$, $CH_2CH_2CONR$, $CH_2CH_2CONRCH_2$, $CH_2CH_2NR$, $CH_2CH_2NRCO$, $CH_2CH_2NRSO_2$, $CH_2CH_2NRCOO$, $CH_2CH_2OCH_2$, $CH_2SO_2NR$, $CH_2SO_2NRCH_2$, $CH_2CH_2OCONR$, $CH_2CH═CH$ or $CH_2C≡C$; where R in the above expressions is hydrogen or methyl and which are linked with the group Y via a carbon atom.

Particularly preferred combinations of Y and X are $SCH_2CH_2$, $SCH_2CH_2N$, $SCH_2CH_2O$, $SCH_2CH_2CH_2$, $SCH_2CH_2CH_2N$ and $SCH_2CH_2CH_2O$.

In formula I, Q is W or a residue of the formula —V-A1-L-A2-W. Alternatively and if X does not represent a bond, Q in formula I may also be —NR10R11.

V can be a divalent aromatic or heterocyclic group, e.g. one of those specifically mentioned above.

In another preferred group of compounds of formula I, V is a divalent group of formula

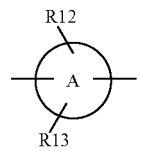

wherein

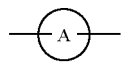

is a phenylene ring or a x-membered saturated or unsaturated divalent heteroaliphatic or heteroaromatic ring containing from 2 to (x−1) carbon atoms with x being 5 to 8, preferably 5 or 6, and from 1 to 4 hetero atoms selected from the group consisting of sulfur, and preferably oxygen and nitrogen, R12 and R13 are independently selected from the group consisting of hydrogen, $C_1$-$C_4$alkyl, $C_1$-$C_4$alkoxy, $C_3$-$C_7$cycloalkyloxy, $C_3$-$C_7$cycloalkyl-$C_1$-$C_4$alkoxy, halogen, halogen-substituted $C_1$-$C_4$alkyl groups, halogen substituted, $C_1$-$C_4$alkoxy groups, cyano, nitro, amino, $C_1$-$C_4$alkylamino, di($C_1$-$C_4$) alkylamino, $C_1$-$C_4$alkylthio, mercapto, hydroxy, carbamoyl, a carboxyl group, an oxo group; or from aryl or heterocyclyl, which may be unsubstituted or substituted with one or more of the above identified substituents other than aryl or heterocyclyl, or when both substituents R12 and R13 are located at adjacent carbon atoms of the ring

these two substituents, taken together with said adjacent carbon atoms, can also form a 5- or 6-membered aromatic or a x-membered saturated or unsaturated heteroaliphatic or heteroaromatic ring containing from 2 to (x−1) carbon atoms with x being 5 to 8, preferably 5 or 6, and from 1 to 4 hetero atoms selected from the group consisting of sulfur and preferably, oxygen and nitrogen, and wherein V can have all together one to four substituents of the kind as defined for R12 and R13 and the free valences can be located either on one or on both rings of the group V.

Particularly preferred meanings of V include:

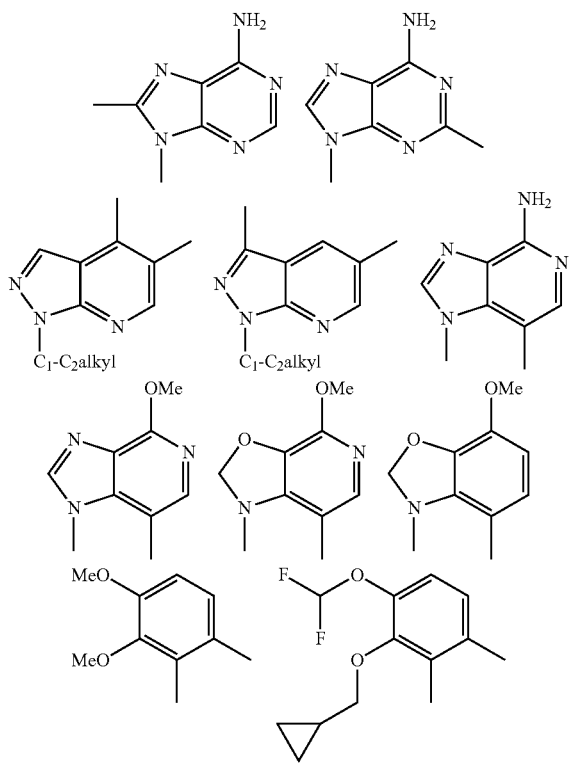

W in formula I can be either aryl or, preferably, heterocyclyl, both as explained above.

In a group —V-A1-L-A2-W, wherein at least one of the groups A1; L or A2 is present, W can also be a monovalent substituted or unsubstituted, saturated or unsaturated linear group with up to 5 atoms consisting of C, N, O and/or S of which one carbon can appear as a CO group one sulphur atom can appear as an $SO_2$ group. In this case W may also carry additional hydrogen atoms to saturate a C or a N atom, as already described above with reference to group X.

In a preferred embodiment of formula I, W represents a group of formula

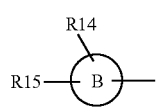

wherein is a phenyl ring or a x-membered saturated or unsaturated heteroaliphatic or heteroaromatic ring containing from 2 to (x−1) carbon atoms with x being 5 to 8, preferably 5 or 6, and from 1 to 4 hetero atoms selected from the group consisting of sulfur, and preferably oxygen and nitrogen, R14 and R15 are independently selected from the group consisting of hydrogen, $C_1$-$C_4$alkyl, $C_1$-$C_4$alkoxy, $C_3$-$C_7$cycloalkyloxy, $C_3$-$C_7$cycloalkyl-$C_1$-$C_4$alkoxy, halogen, halogen-substituted $C_1$-$C_4$alkyl groups, halogen substituted $C_1$-$C_4$alkoxy groups, cyano, nitro, amino, $C_1$-$C_4$alkylamino, di($C_1$-$C_4$)alkylamino, $C_1$-$C_4$alkylthio, mercapto, hydroxy, carbamoyl, a carboxyl group, and an oxo group; or when both substituents R14 and R15 are located at adjacent carbon atoms of the ring these two substituents, taken together with said adjacent carbon atoms, can also form a 5- or 6-membered aromatic or a x-membered saturated or unsaturated heteroaliphatic or heteroaromatic ring containing from 2 to (x−1) carbon atoms with x being 5 to 8, preferably 5 or 6, and from 1 to 3 hetero atoms selected from the group consisting of sulfur and preferably, oxygen and nitrogen, wherein W can have all together one to four substituents of the kind as defined for R14 and R15 and the free valence can be located on either ring of the group W.

Particularly preferred examples of W are the following groups:

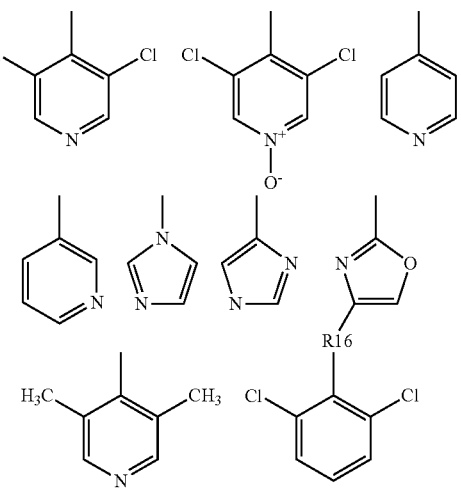

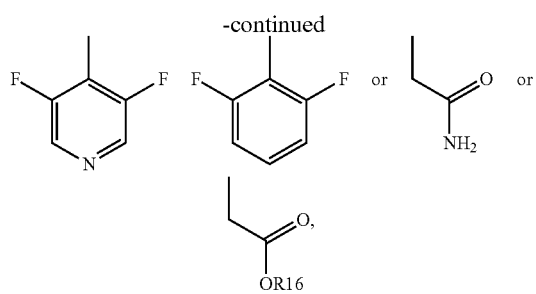

wherein R16 is hydrogen or $C_1$-$C_4$alkyl, in particular methyl.

In a group —V-A1-L-A2-W groups A1 and A2 are, in general, independently of each other either absent or a $C_1$-$C_4$alkylene group. L is generally selected from a single bond, —O—, —S—, —SO$_2$—, —NH—, —CO—, —(CO)O—, —O(OC)—, —(CO)NH—, —NH(CO)—, —(SO$_2$)NH—, —HN(SO$_2$)—, —HN(CO)NH—, —O(CO)NH—, and —NH(CO)O— in such group, but may also be absent if A1 and/or A2 are present.

In preferred examples of macrolide compounds according to the invention A1 and A2 are independently of each other either absent or represent a $C_1$-$C_2$alkylene group; and L is selected from —NH—, —(CO)NH— and —NH(CO)—; or is absent.

Particularly preferred are the compounds of formula (I) wherein
A1, A2 are independently of each other either absent or a $C_1$-$C_2$alkylene group;
L is —NH—, —(CO)NH— or —NH(CO)—;
V is a divalent group of formula

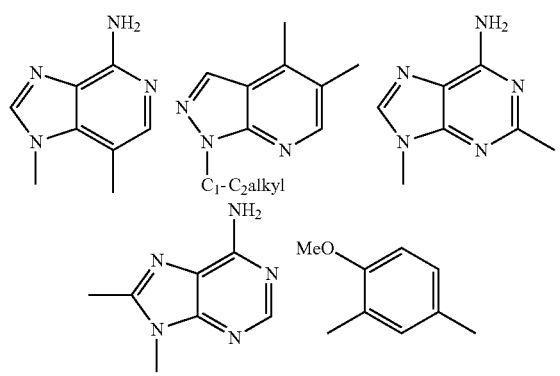

and
W is a group of formula

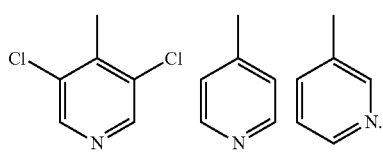

Also preferred are the compounds according to the present invention, in particular those mentioned in the preceding paragraph, wherein
Y is —S— and
X is —CH$_2$—CH$_2$—CH$_2$— or, preferably, —CH$_2$—CH$_2$—NH—, —CH$_2$—CH$_2$—O—, —CH$_2$—CH$_2$—CH$_2$—NH— or —CH$_2$—CH$_2$—CH$_2$—O— linked to the residue Q via the NH group or O atom respectively, or —CH$_2$—CH$_2$—, most preferably —CH$_2$—CH$_2$—.

Preferred examples of corresponding macrolide compounds according to the invention are compounds of formula I wherein Q has the following formula

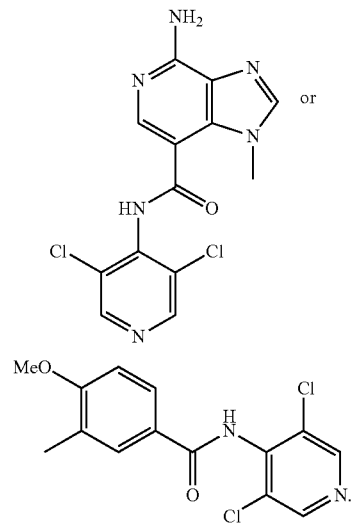

If X does not represent a bond in formula I, then Q may also be —NR10R11. In this case R10, and R11 may be independently selected from aryl, aralkyl, heterocyclyl and heterocyclylalkyl, e.g. as explained above, and one of R10 and R11 can also be a group -L-A2-W; wherein L and W have one of the meanings mentioned above.

Preferred examples of corresponding macrolide compounds according to the invention are compounds of formula I wherein Q is a group —NR10R11 and has one of the following formulae

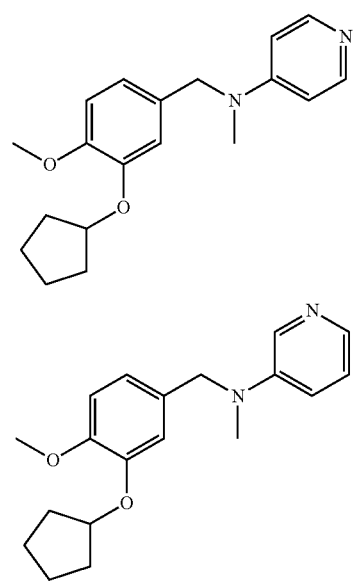

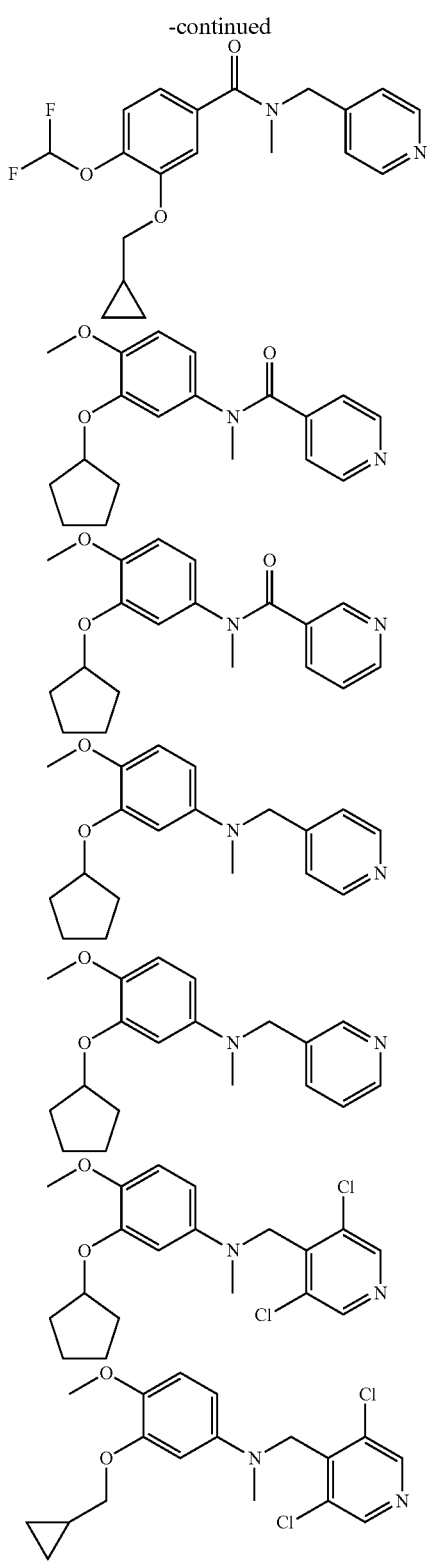
wherein
means a methoxy residue.
In specific embodiments of the compounds of formula (I) group Q represents a residue W as generally defined above. Specific compounds of this type comprise as group W a group of one of the formulae
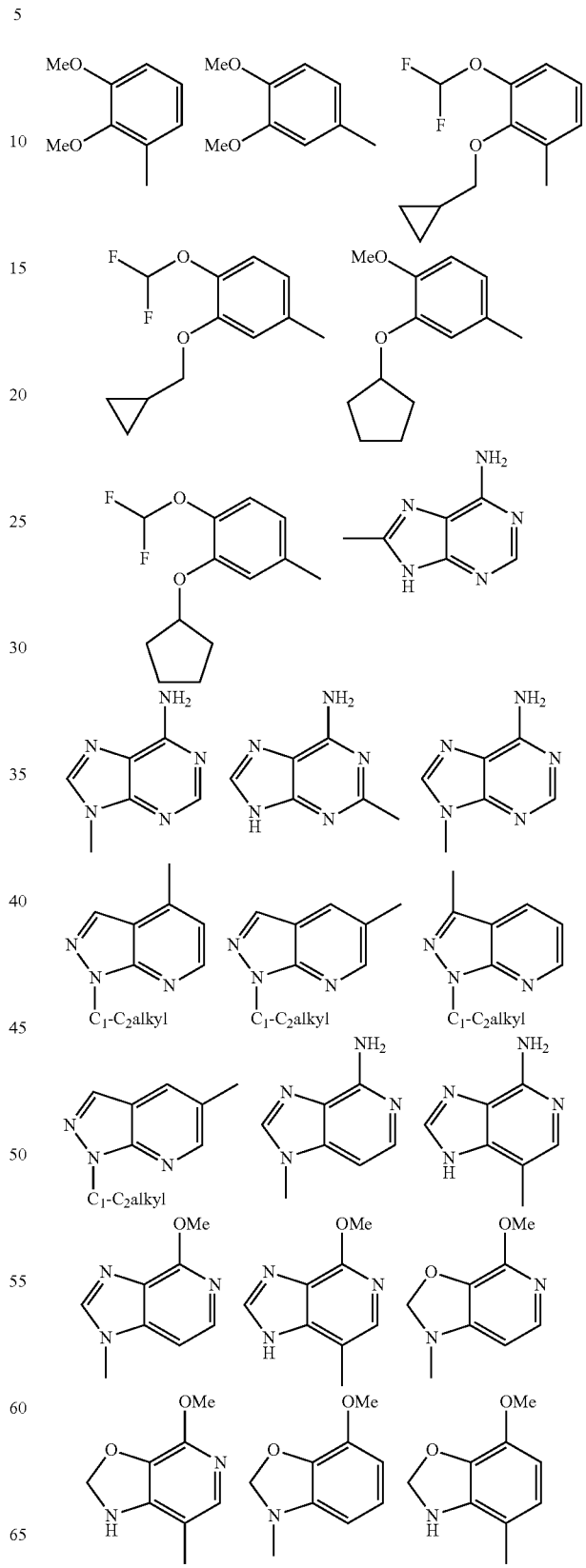

-continued

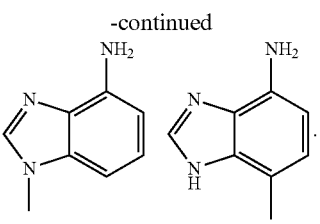

It is furthermore preferred, when one of the residues R5 and R6 and/or one of the residues R7 and R8 is hydrogen and the respective other one is not hydrogen, also in combination with other preferences described herein.

Preferred as well are compounds of formula I, wherein either R5 is —NR5aR5b and/or R7 is —NR7aR7b.

Also preferred are compounds according to the invention, wherein R6 is —OR6a and/or R8 is —OR8a.

Further preferred embodiments of the compounds of the present invention include: the compounds, wherein R8 and R9 taken together with the bond between the carbon atoms to which they are linked, form a double bond;

the compounds wherein R9 is hydrogen;

the compounds, wherein R5a, R6a, R7a, R8a, independently of each other, are hydrogen or C1-C6alkyl or vinyl, or R56 and R78, R5b, R5c, R6b, R6c, R7b, R7c, R8b and R8c, independently of each other, are hydrogen or C1-C6 alkyl;

the compounds, wherein R2 is

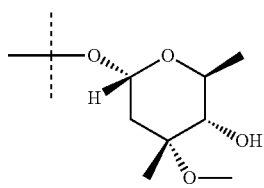

wherein

represents the linking bond;

the compounds wherein R2a is hydrogen;

the compounds, wherein R2 and R3 taken together with the carbon atom to which they are linked, represent a C=O group; or the compounds, wherein R2 and R4 taken together with the bond between the carbon atoms to which they are linked, form a double bond.

Further preferred compounds according to the invention are the following:

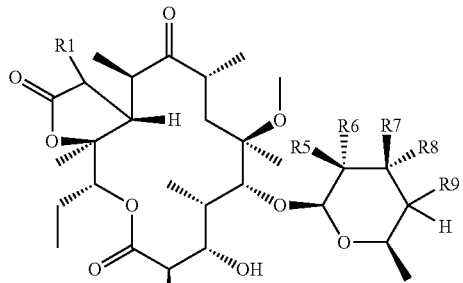

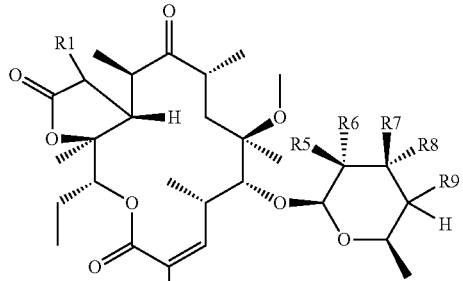

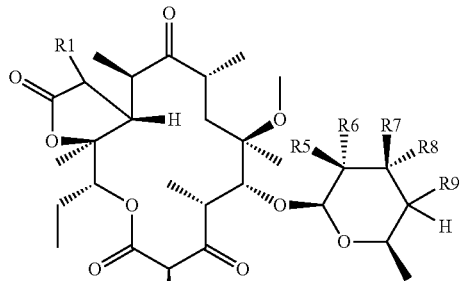

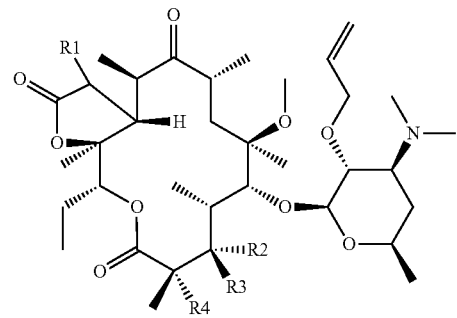

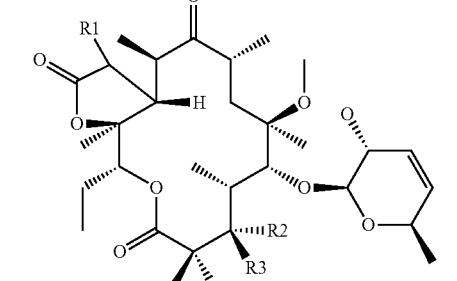

17
-continued
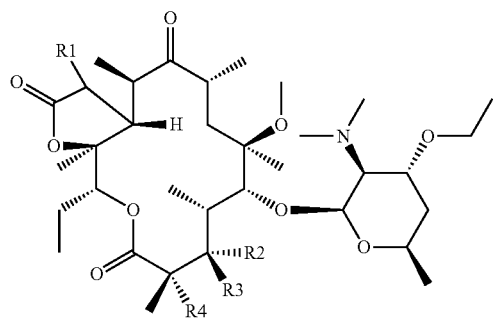
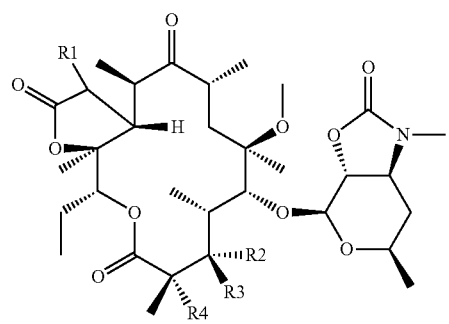
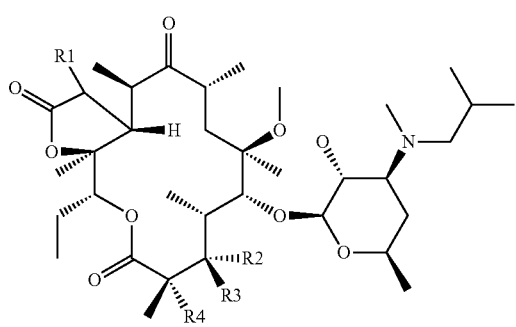
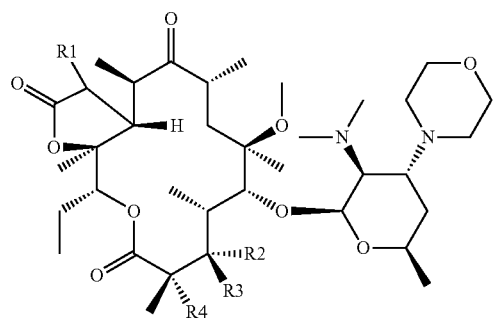
18
-continued
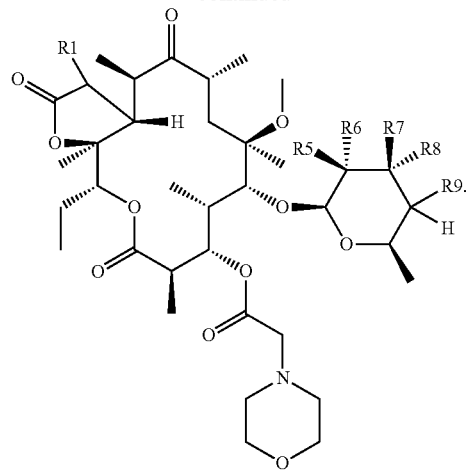
Specific examples of the compounds of the present invention include, e.g.:
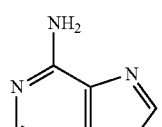
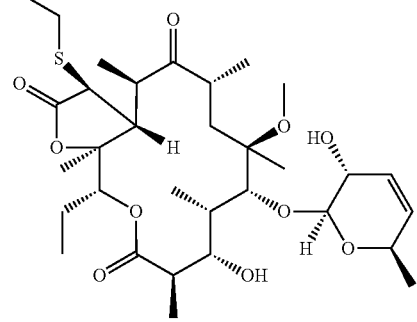
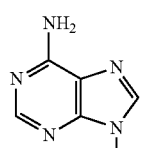
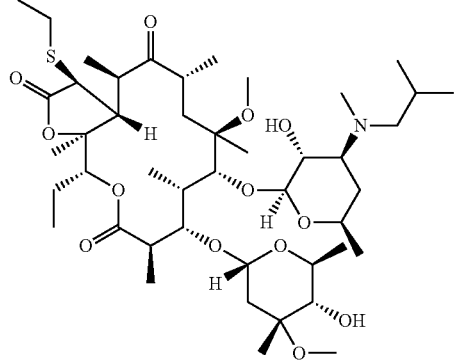

19
-continued
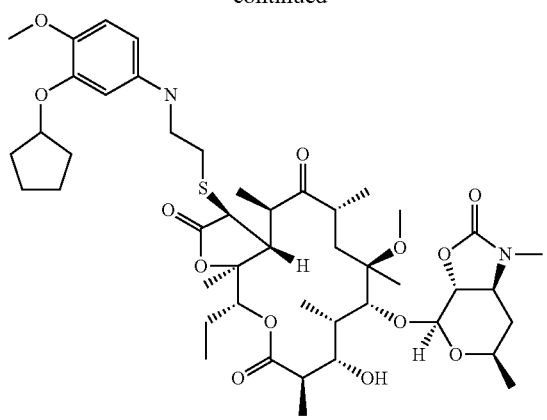
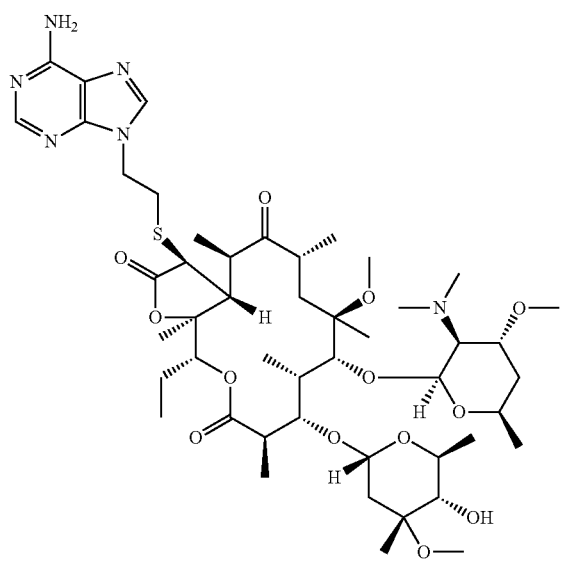 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@@H](OC)[C@@H]2N(C)C)[C@](C)(OC)C[C@@H](C)C(=O)[C@H](C)[C@H]2[C@H](SCCn3cnc4c(N)ncnc43)C(=O)O[C@@]21C]
as well as the compounds of formula:
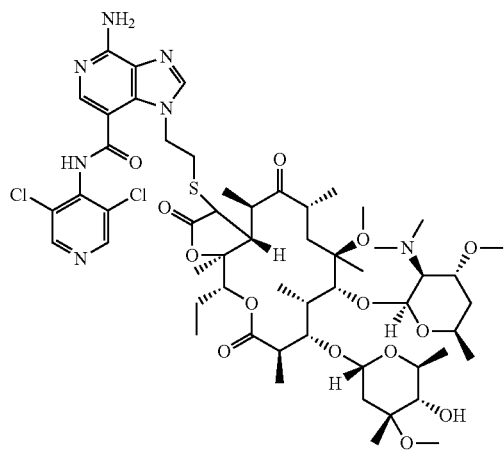
20
-continued
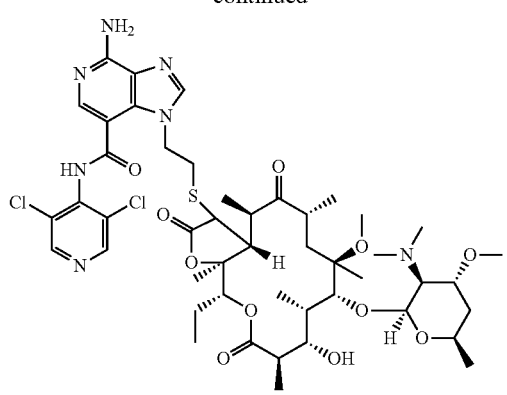
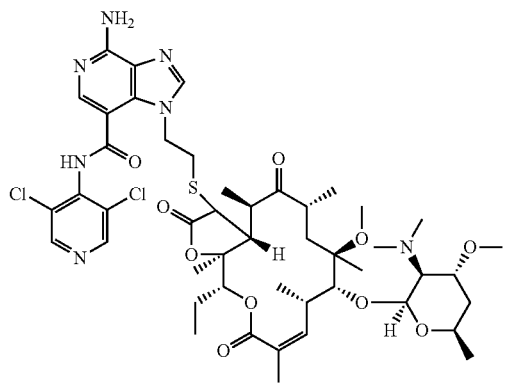
and the compounds of formula:
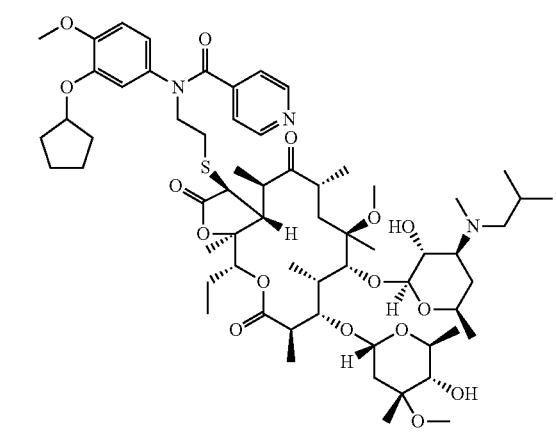

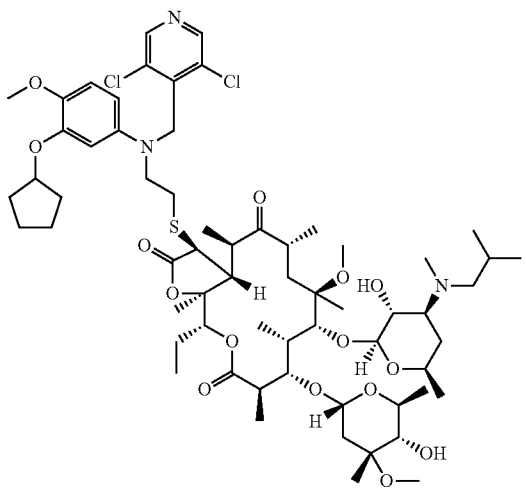

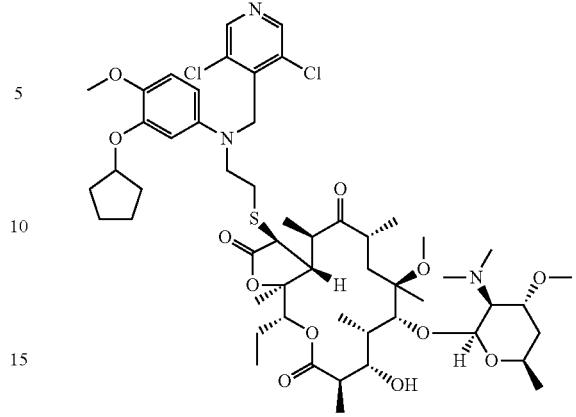

A further preferred compound according to the invention is:

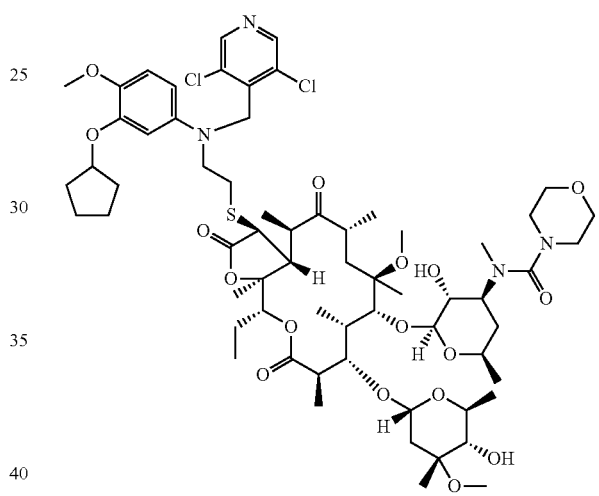

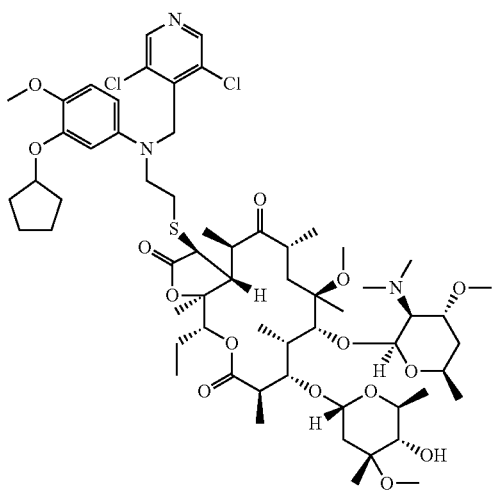

As already indicated above, the macrolide compounds of formula I can, if desired, also be present and used as pharmaceutically acceptable acid addition salts. Not only salts with inorganic acids, but also salts with organic acids come into consideration. Hydrochlorides, hydrobromides, sulfates, nitrates, citrates, acetates, trifluoroacetates, maleates, succinates, methanesulphonates, p-toluenesulphonates and the like are examples of such salts.

Further, the compounds of formula I can be in form of in vivo cleavable esters, for example esters with of the 2'-hydroxy group of the sugar moiety. Suitable esters are generally acetates, pivaloyl esters, tartrates, maleates, succinates, and the like.

The compounds of the present invention including their pharmaceutically acceptable acid addition salts or in vivo cleavable esters thereof are useful for the prevention and/or treatment of diseases such as chronic obstructive pulmonary disease (COPD), asthma, rheumatoid arthritis, atopic dermatitis or inflammatory bowel disease.

The compounds of the present invention and their pharmaceutically acceptable acid addition salts or in vivo cleavable esters thereof can also be used for the prevention and/or treatment of diseases such as chronic bronchitis, emphysema, urticaria, allergic rhinitis, allergic conjunctivitis, psoriasis, septic shock, adult respiratory distress syndrome and multiple sclerosis and for the treatment of human (+animal) diseases associated with uncontrolled cellular growth, proliferation and/or survival e.g. cancer.

The compounds in accordance with the invention can be used as medicaments. A further embodiment of the present invention are thus medicaments comprising compounds of formula I, their pharmaceutically acceptable acid addition salts, N-oxides or in vivo cleavable esters thereof for the treatment and prevention of inflammatory diseases or allergic diseases or diseases associated with uncontrolled cellular growth, proliferation and/or survival in subjects selected from animals, e.g. mammals, and preferably humans, for example, in the form of pharmaceutical preparations for enteral (oral) administration. The products in accordance with the invention can be administered, for example, perorally, such as in the form of tablets, film coated tablets, sugar coated tablets, hard and soft capsules, solutions, emulsions or suspensions, or rectally, such as in the form of suppositories, or parenterally e.g. by injection, or nasally, or by inhalation or transdermally, or locally for example by topical administration, preferably the compounds are administered topically or orally.

Pharmaceutical compositions containing these compounds can be prepared using conventional procedures familiar to those skilled in the art, such as by combining the ingredients into a dosage form together with suitable, non-toxic, inert, therapeutically compatible solid or liquid carrier materials and, if desired, the usual pharmaceutical adjuvants.

It is contemplated that the compounds are ultimately embodied into compositions of suitable oral, parenteral or topical dosage forms. The compositions of this invention can contain, as optional ingredients, any of the various adjuvants which are used ordinarily in the production of pharmaceutical preparations. Thus, for example, in formulating the present compositions into the desired oral dosage forms, one may use, as optional ingredients, fillers, such as microcrystalline cellulose, calcium phosphate or lactose; disintegrating agents, such as starch, crosslinked carboxymethylcellulose sodium or crosslinked polyvinylpyrrolidone; and lubricating agents, such as talc, magnesium stearate, calcium stearate, and the like. It should be fully understood, however, that the optional ingredients herein named are given by way of example only and that the invention is not restricted to the use hereof. Other such adjuvants, which are well known in the art, can be employed in carrying out this invention.

Suitable as such carrier materials are not only inorganic, but also organic carrier materials. Thus, for tablets, film coated tablets, sugar coated tablets and hard capsules there can be used, for example, lactose, maize starch or derivatives thereof, talc, stearic acid or its salts. Suitable carriers for soft capsules are, for example, vegetable oils, waxes, fats and semi-solid and liquid polyols (depending on the nature of the active substance). Suitable carrier materials for the preparation of solutions and syrups are, for example, water, alcohols, polyols, saccharose, invert sugar and glucose. Suitable carrier materials for suppositories are, for example, natural or hardened oils, waxes, fats and semi-liquid or liquid polyols.

As pharmaceutical adjuvants there are contemplated the usual preservatives, solubilizers, stabilizers, wetting agents, emulsifiers, sweeteners, colorants, flavoring agents, salts for adjusting the osmotic pressure, buffers, coating agents and antioxidants.

The compounds of formula I and their acid addition salts, N-oxides or in vivo cleavable esters thereof can be used for parenteral administration and for this purpose are preferably made into preparations for injection as lyophilisates or dry powders for dilution with customary agents, such as water or isotonic common salt solution.

The compounds of formula I and their acid addition salts, N-oxides or in vivo cleavable esters thereof can be used for topical administration and for this purpose are preferably made into preparations as ointments, creams or gels.

For the treatment and/or prevention of inflammatory and allergic diseases in mammals, humans and non-humans, a daily dosage of about 10 mg to about 2000 mg, especially about 50 mg to about 1000 mg, is usual, with those of ordinary skill in the art appreciating that the dosage will depend also upon the age, conditions of the mammals, and the kind of diseases being prevented or treated. The daily dosage can be administered in a single dose or can be divided over several doses. An average single dose of about 10 mg, 100 mg, 250 mg, 500 mg and 1000 mg can be contemplated.

The preparation of compounds of formula I can e.g. be carried out according to schemes 1-13.

Scheme 1

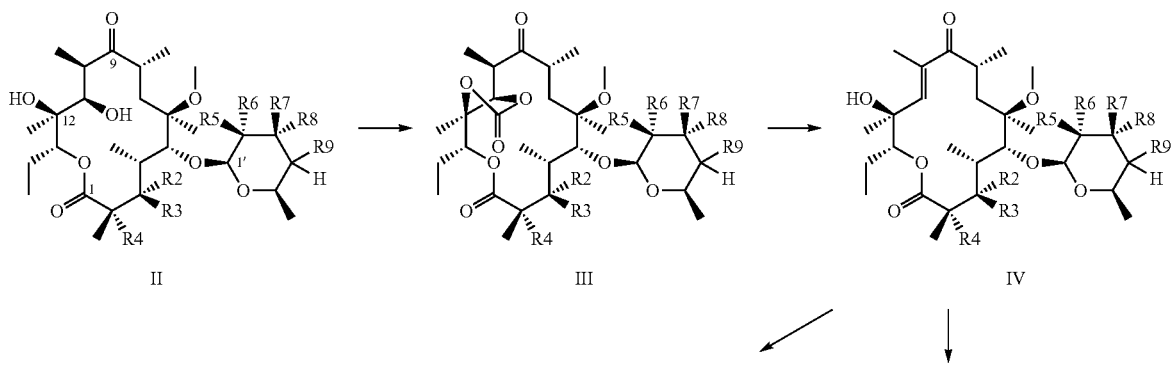

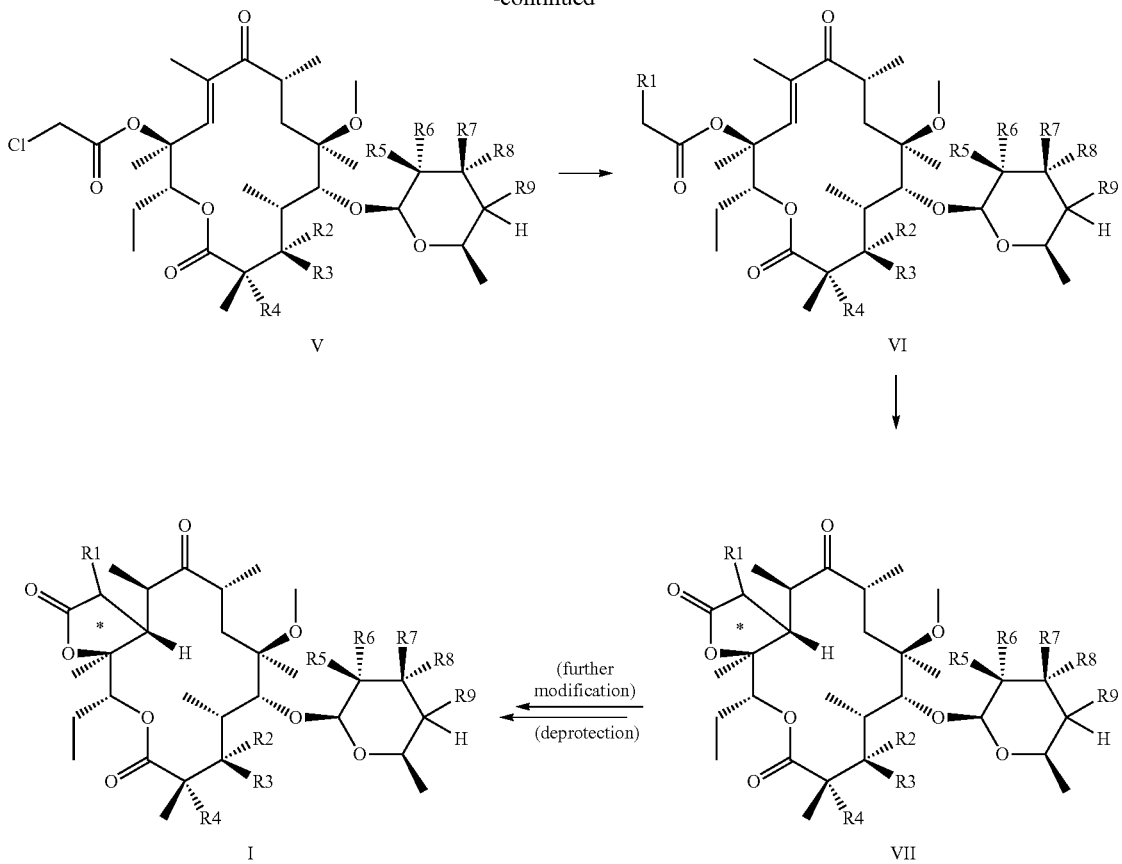

For example, compounds of the present invention can be prepared starting from clarithromycin as illustrated in general scheme 1. In a first step clarithromycin or a derivative thereof with the general formula II wherein the groups R2-R9 are as defined above or appropriately protected according to methods well known in the art are transformed into compounds of formula IV (via III) in a similar way as described in Baker et al., J. Org. Chem. 1988, 53, 2340-2345. The hydroxy group at position 12 of compounds of formula IV is esterified according to standard methods by treatment for example with 2-chloro acetic acid, an activating agent like DCC and DMAP or with 2-chloro acetic anhydride, pyridine, DMAP in a solvent such as methylene chloride. The intermediate V is then treated with the appropriate nucleophile Q-X—SH where Q and X are as defined above in acetone in the presence of a base such as DBU to give compounds of formula VI wherein R1-R9 are as defined above. Depending on the nature of R1 compounds of formula VI can also be synthesized by reacting compound of formula IV with an appropriate carboxylic acid (R1CH$_2$COOH), an activating agent like DCC and DMAP in a suitable solvent such as methylene chloride to give compounds of formula VI. Compounds of formula VI are treated with an alkali metal base such as NaH or potassium tert.-butoxide or LDA in an aprotic solvent such as DMF or THF to give compounds of formula VII where the groups R2-R9 are as defined above (scheme 1).

If necessary compounds of general formula VII are deprotected according to methods well known in the art as described e.g. in T. W. Green et al., Protective Groups in Organic Synthesis, John Wiley & Sons, 1999 to give compounds of general formula I.

In the case where R1 is S-Rp$_3$ (scheme 2) and Rp$_3$ is a sulphur protecting group e.g. benzyl, 4-methoxybenzyl, 3,4-dimethoxybenzyl or 4-nitro-benzyl, preferably 4-methoxybenzyl, the intermediate VIIa is transformed into disulfide derivative VIII wherein R2-R9 are as defined above and Rp$_4$ is e.g. 3-nitro-2-pyridinyl or methyl similar to the method described in WO03/072588 or in WO2006084410. Compounds of formula VIII are treated with a reducing agent such as a trialkyl phosphine, preferably tributyl phosphine, or a triaryl phosphine, preferably triphenyl phosphine, in a solvent such as aqueous acetone, aqueous dimethyl formamide, aqueous dioxane or aqueous tetrahydrofuran, preferably aqueous dimethyl formamide, preferably at 0° C. to 60° C., for 1 minute to 1 hour, to give compound IX. Compound IX is treated, preferably without isolation, directly in the same solvent system with compounds of the formula Q-X-Lg, in which Q and X are as defined before and Lg is a leaving group, e.g. chloride, bromide, iodide, methanesulfonyloxy, p-tosylsulfonyloxy, trifluoromethanesulfonyloxy to give, after removal of any protecting group, compounds of formula Ia (scheme 2). The reaction is preferably effected in the presence of a base such as alkali metal carbonate or hydrogen carbonate, e.g. potassium carbonate, cesium carbonate or sodium hydrogen carbonate, or an organic base, e.g. triethylamine, N-ethyl N,N-diisopropylamine, 1,8-diazabicyclo [5.4.0]undec-7-ene or 1,5-diazabicyclo[4.3.0]non-5-ene, preferably 1,8-diazabicyclo[5.4.0]undec-7-ene at temperature between 0° C. and 50° C. It can be advantageous to add catalytic amounts of an iodide salt, preferably sodium iodide, to the reaction mixture. If required, protecting groups are removed according to methods well known in the art as described e.g. in T. W. Green et al., Protective Groups in Organic Synthesis, John Wiley & Sons, 1999.

Scheme 2

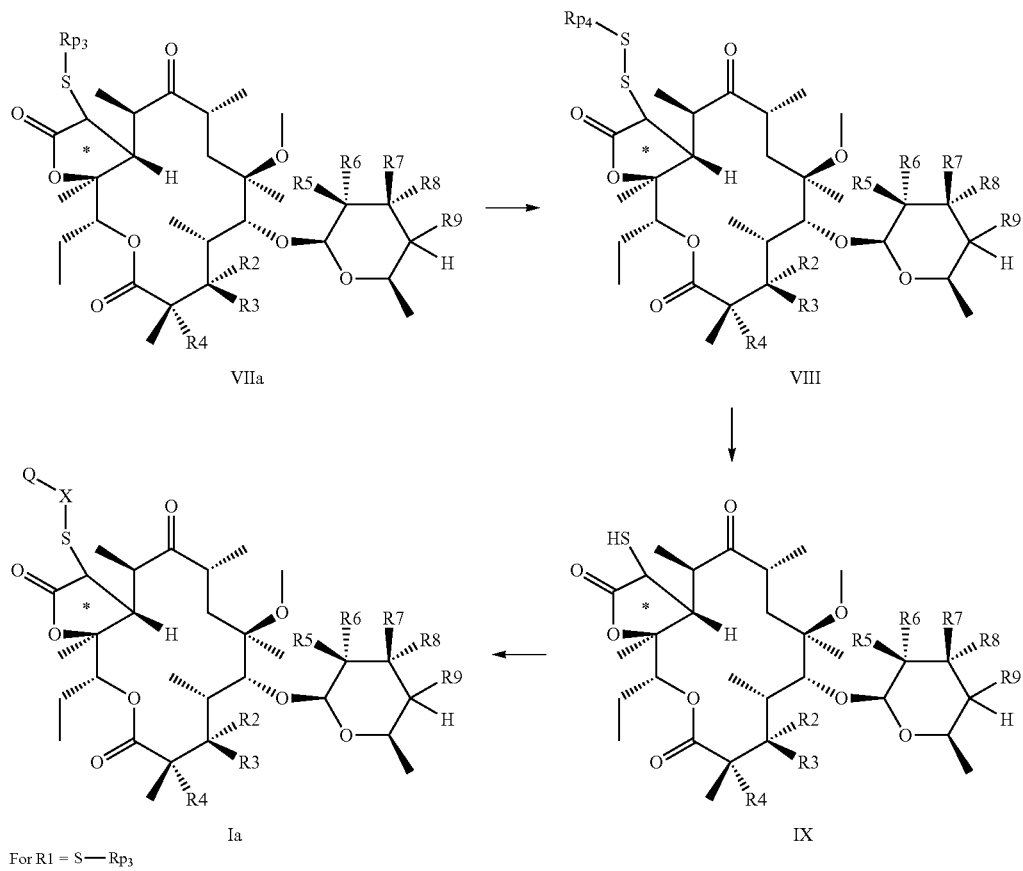

Modifications at positions 2 and/or 3 of the macrolactone ring (i.e. R2-R4) and at positions 1'-4' of the sugar moiety (i.e. R5-R9) can be introduced before, during or at the end of the preparation of molecules of general formula I according to the general schemes 1 and 2. The appropriate time point for such modifications depends on the nature of the conditions applied as it is well known to any person skilled in the art and might require protection of certain functional groups with a suitable protecting group and subsequent deprotection according to standard procedures described in T. W. Green et al., Protective Groups in Organic Synthesis, John Wiley & Sons, 1999. Such modifications are further described in schemes 3-14.

Scheme 3

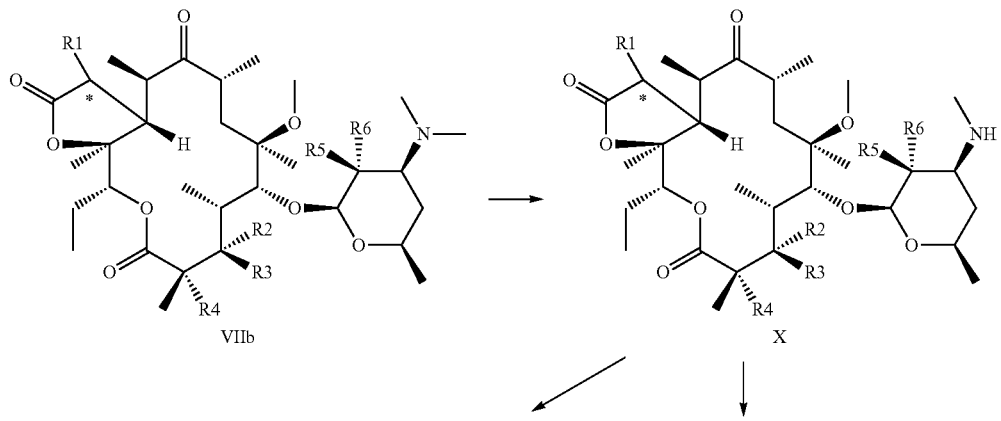

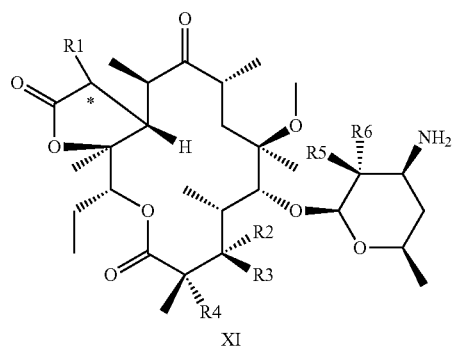
XI

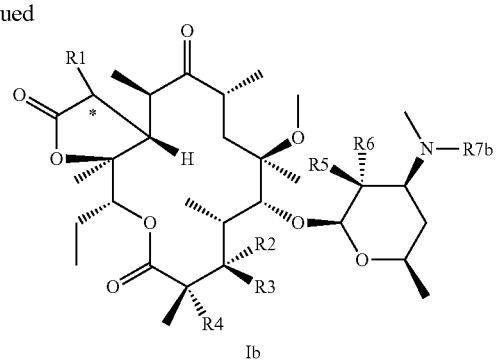
Ib

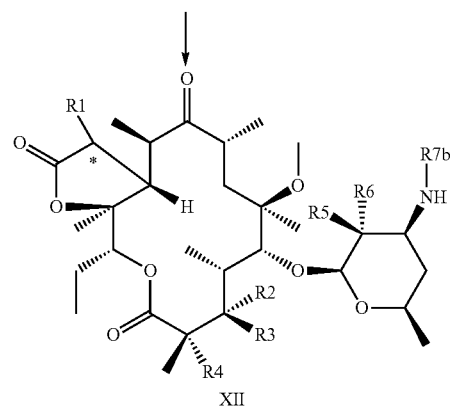
XII

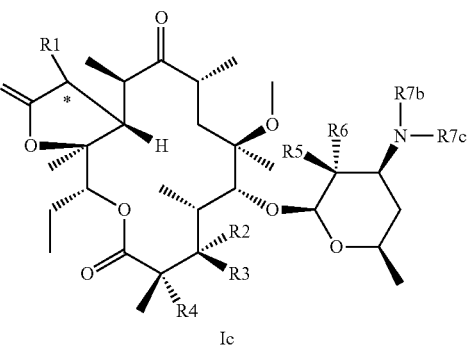
Ic

Compounds of formula Ib and Ic wherein R7b and R7c are as defined above but are not methyl may be prepared from compounds of formula VIIb (scheme 3). N-demethylation is for example performed using iodine under light or N-iodosuccinimide according to procedures described in the literature (J. Med. Chem., 1995, 38, 1793; J. Org. Chem. 2000, 65, 3875) to give compounds of formula X or of formula XI. Substituents R7b and R7c are introduced e.g. by reductive amination using the appropriate aldehyde in the presence of a reducing agent such as NaCNBH$_3$ in a solvent such as methanol preferably at room temperature or by alkylation with an alkylhalide in the presence of base such as sodium hydride or sodium carbonate in a solvent such as DMF, acetonitrile, toluene or the like to give compounds of formula Ib or Ic. The two groups R7b and R7c can be introduced simultaneously or sequentially, preferably sequentially. Compounds of formula X and XI can also react with a substituted chlorformiate, substituted carbonyl chloride or carboxylic acid under standard conditions known in the art for the formation of amide bonds. Alternatively, groups R7b and R7c may be introduced starting from compounds of formula XIII or XV according to similar methods as described above as shown in scheme 4 to give compounds of formula XIV and XVII. Those compounds are then further modified according to any of the schemes 1-14 to give compounds of general formula Ib and Ic.

Scheme 4

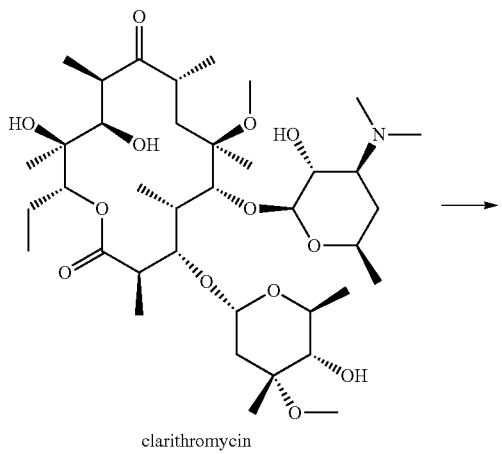
clarithromycin

-continued
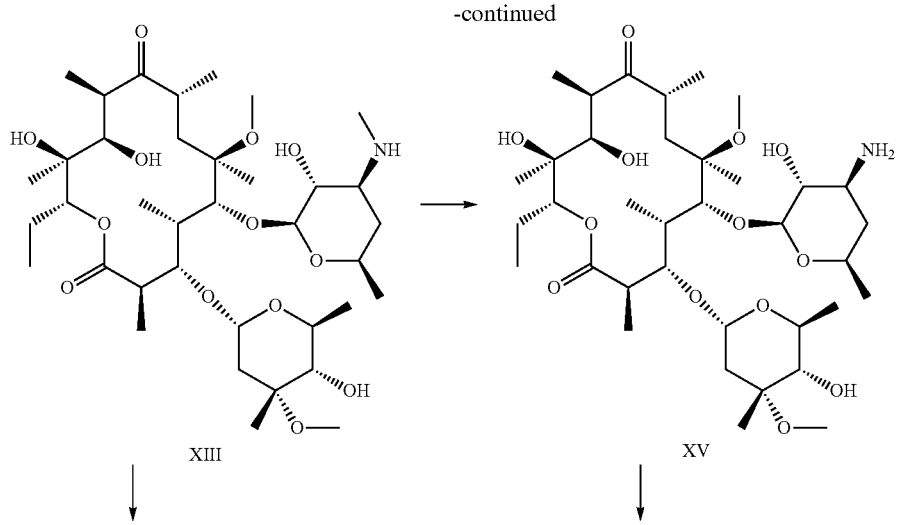
XIII → XV
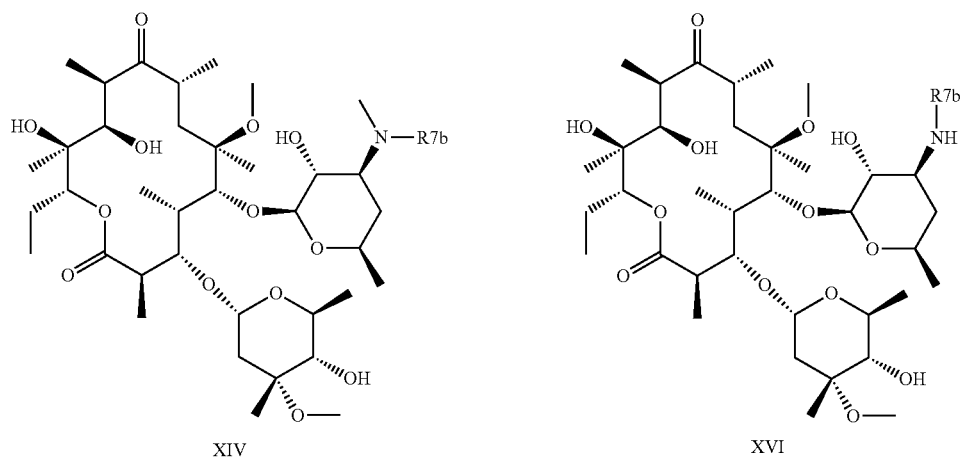
XIV    XVI
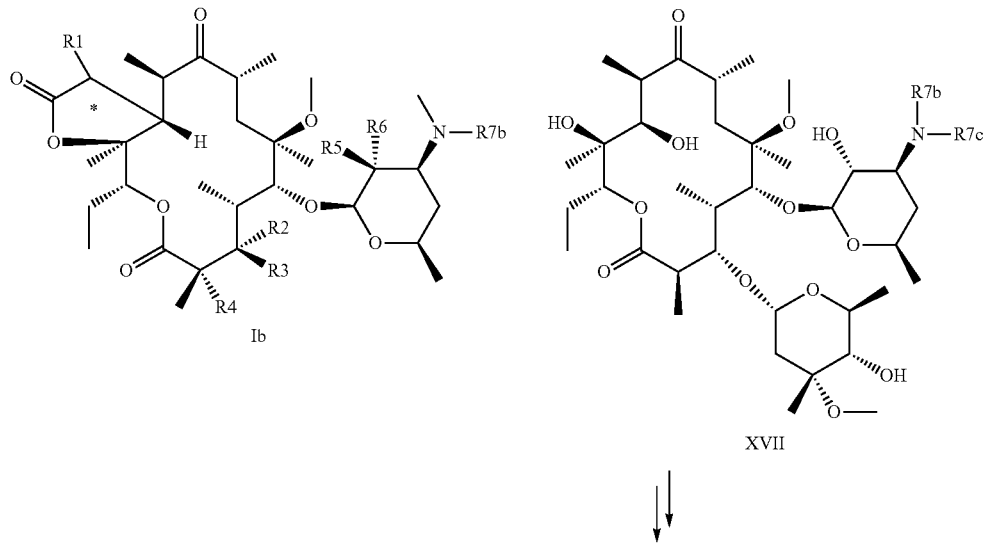
Ib    XVII

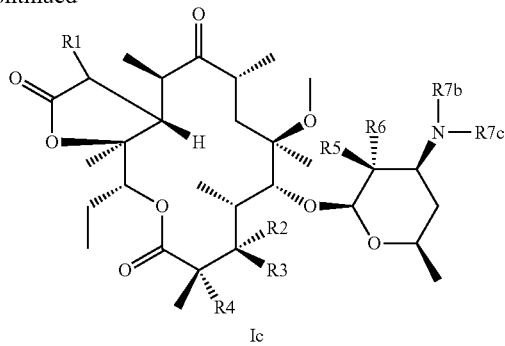

Ic

Compounds of formula Id and formula Ie may be prepared starting from clarithromycin. In a first step clarithromycin is treated for example with hydrogen peroxide in a solvent such as methanol preferably at room temperature to give compound XVIII. Compound XVIII is then pyrolyzed at preferably 150° C. to 190° C. to give a compound of formula XIX. Protection of the 2' and the 4"-hydroxyl groups can be achieved by reaction with a suitable acid anhydride or acid chloride by methods described in the literature to give compounds of formula XX where Rp1 and Rp2 are acetyl, benzoyl, benzyloxycarbonyl or the like. Alternatively compound of formula XIX is hydrogenated under an atmosphere of hydrogen gas in the presence of a catalyst such as palladium on carbon to give, after protection according to the method described above, compound of formula XXII. Compounds of formula XX and XXII are then further modified according to any of schemes 1-14 to give compounds of general formula Id and Ie.

Scheme 5

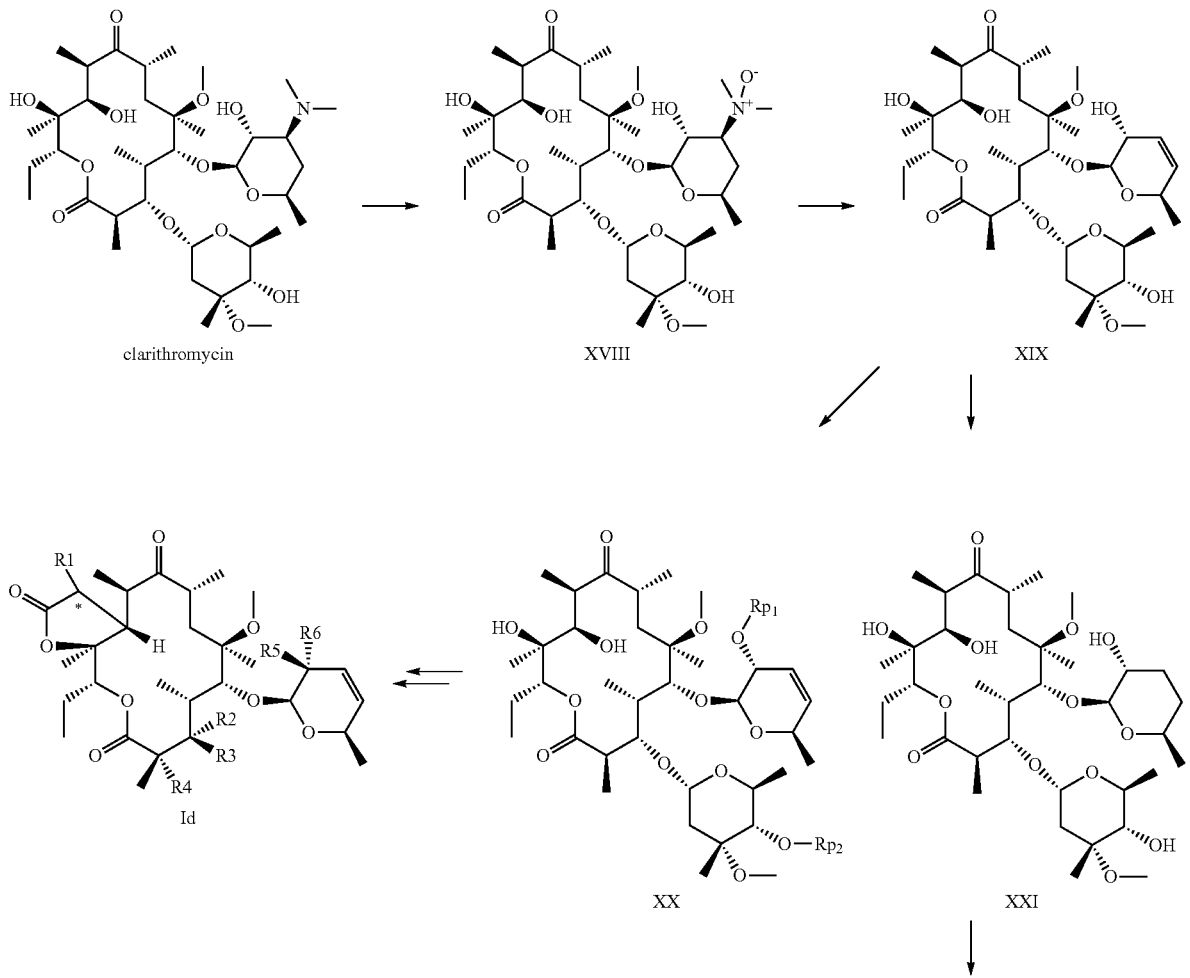

-continued

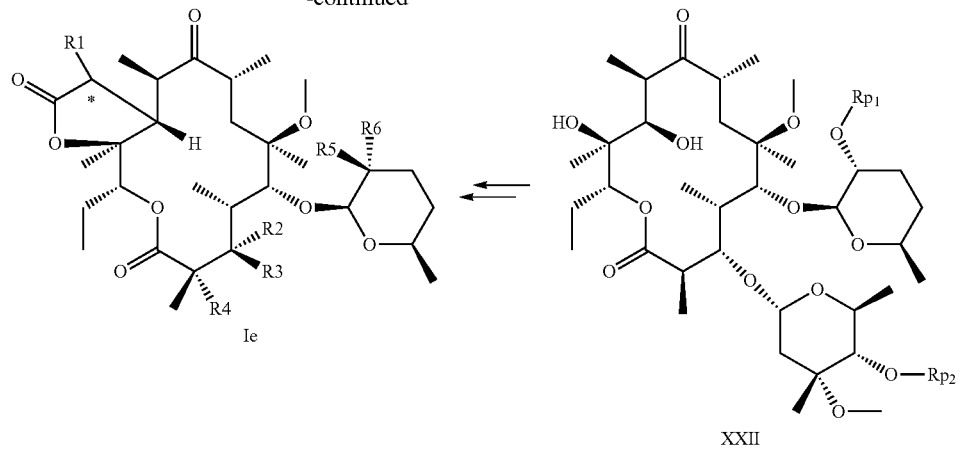

Compounds of formula XXVII may be obtained starting from compound XXIV where Rp1 and Rp2 are as defined above, preferably acetyl. Compound XXIV is selectively deprotected at position 2', in the case where Rp1 is acetyl by stirring in methanol at a temperature in the range of 20-50° C., to give compound of formula XXV. This intermediate is treated with a reagent such as mesyl chloride, methanesulfonic anhydride, tosylchloride, preferably methanesulfonic anhydride in a solvent such as dichloromethane in the presence of a base like pyridine at a temperature in the range of 0-30° C. to give compounds of formula XXVI where Ra is methyl, trifluoromethyl, or methylphenyl. Compound XXVI is then treated with the appropriate nucleophile comprising the group R8 such as for example methanol, ethanol, morpholine, dimethylamine and the like to give compounds of general formula XXVII. Compounds of formula XXVII are then further modified according to any of schemes 1-14 to give compounds of general formula If (scheme 6). Alternatively, compounds of formula If can be obtained starting from compounds of formula XXVIII as described in scheme 7 according to procedures similar to those described above. Compounds of formula XXVIII are obtained according to scheme 1.

Scheme 6

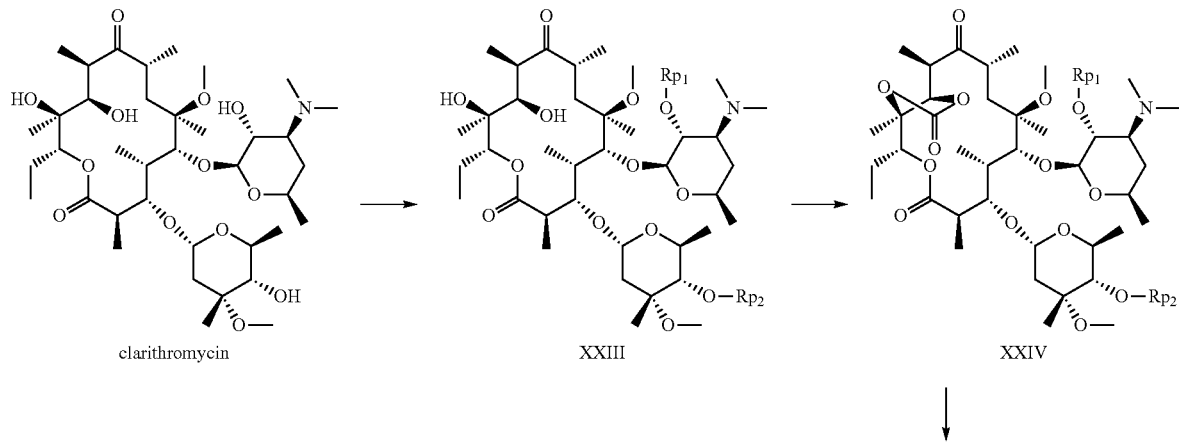

37
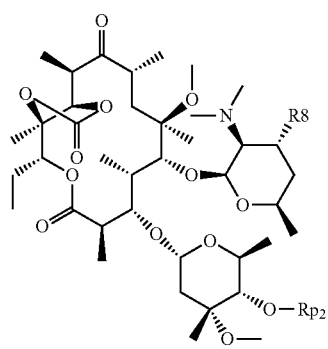
XXVII
-continued
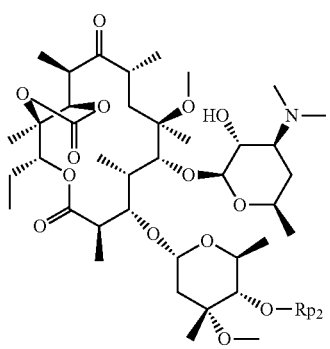
XXVI
38
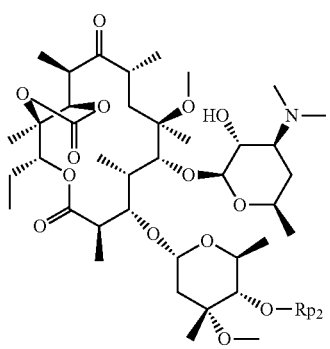
XXV
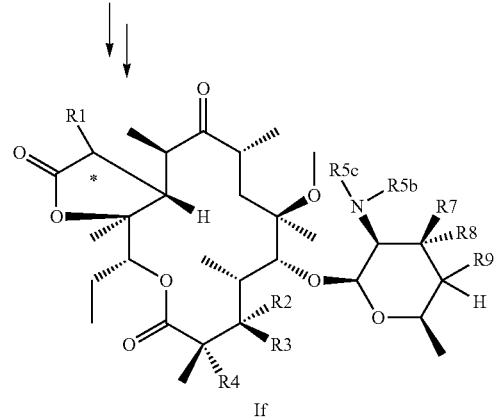
If Scheme 7
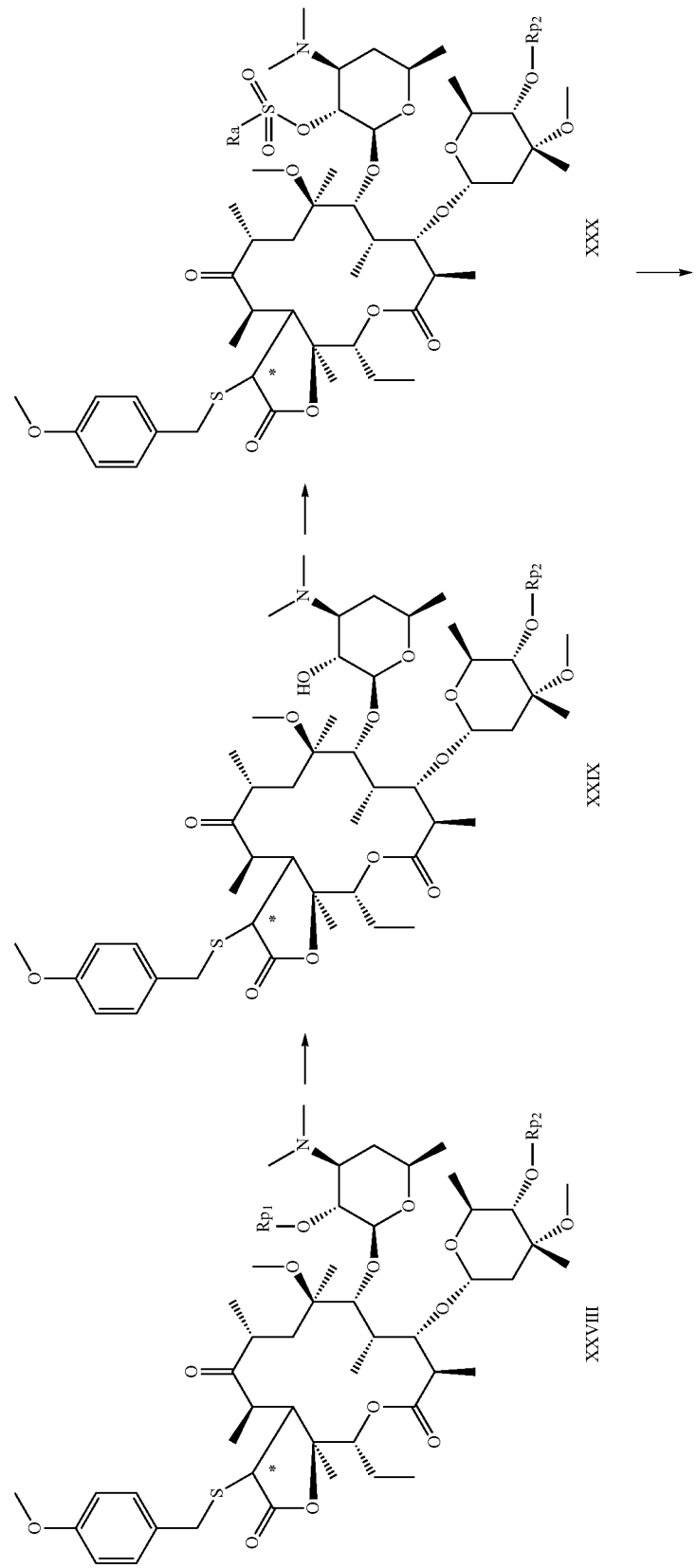

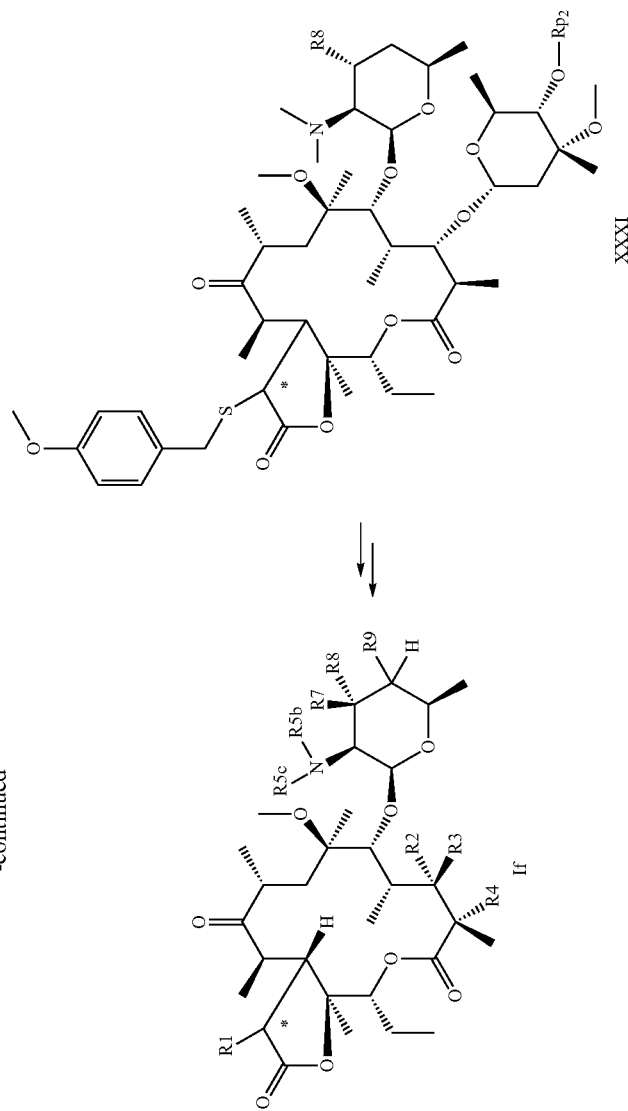

Compounds of general formula I where in R6 is O—R6a may be prepared from compounds of general formula XXXII. The hydroxyl group in position 2' can be alkylated following methods known in the art, for example by treatment with an alkylhalide in the presence of a base such as sodium hydride, sodium carbonate or potassium carbonate in a solvent such as DMF, THF, DMSO, acetone or a mixture thereof to give compounds of formula XXXIII (scheme 8). Compounds of formula XXXIII are then further modified according to any of the schemes 1-14 to give compounds of general formula Ih.

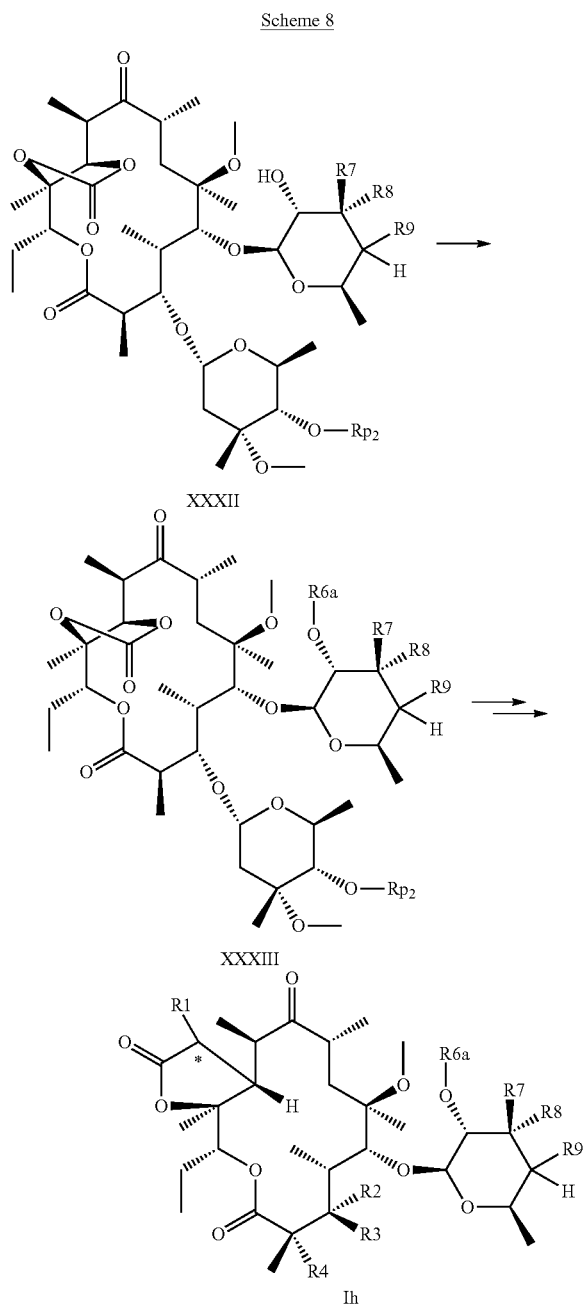

2,3-Anhydro-macrolactones may be prepared as described in scheme 9. Compound XXXIV (J. Med. Chem. 1998, 41, 1651) is treated with a base such as sodium hydride in a solvent such as DMF or THF or a mixture thereof at 0° C. to 25° C. to give the compound of formula XXXV. The compound of formula XXXV is then further modified according to any of schemes 1-14 to give compounds of general formula II (scheme 9).

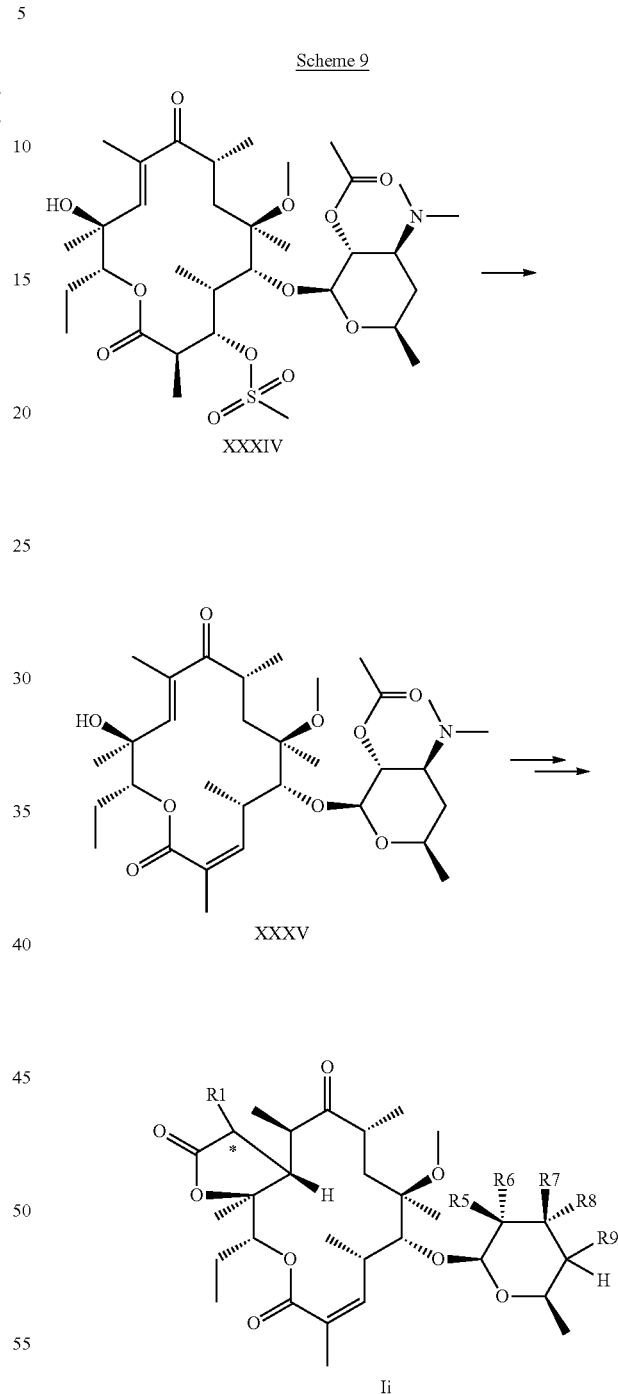

Compounds of formula I wherein R2 and R3 taken together form a carbonyl group may be synthesized starting from compound XXXVI (J. Med. Chem. 1998, 41, 4080). The compounds of formula XXXVI are then modified according to any of the schemes 1-14 to give compounds of general formula Ik (scheme 9). Alternatively, the carbonyl group at position 3 can be introduced later in the synthesis according to methods well known in the art (e.g. WO03/072588) (scheme 11).

Scheme 10

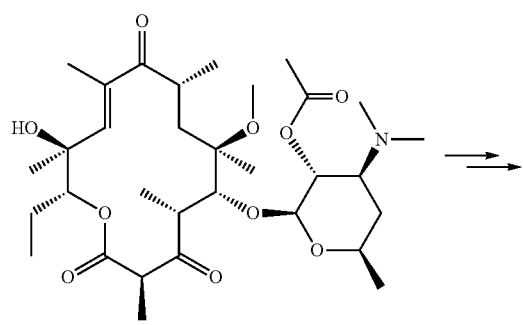

XXXVI

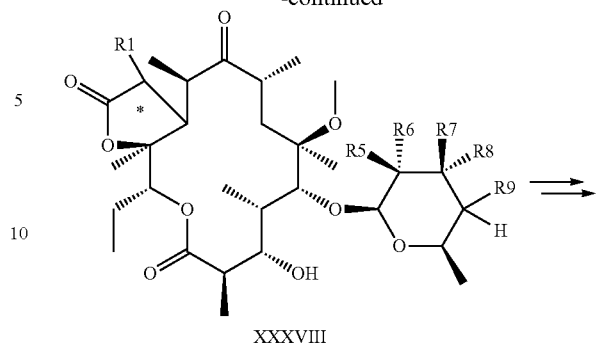

XXXVIII

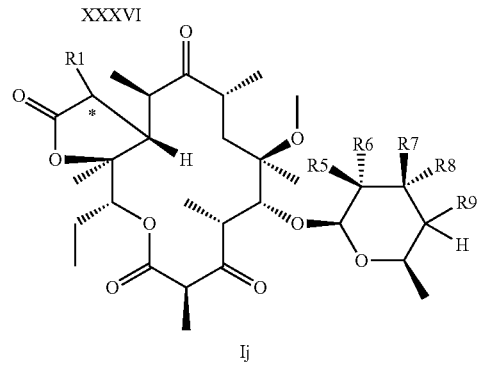

Ij

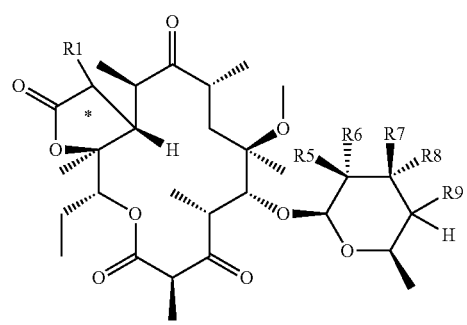

Ik

Scheme 11

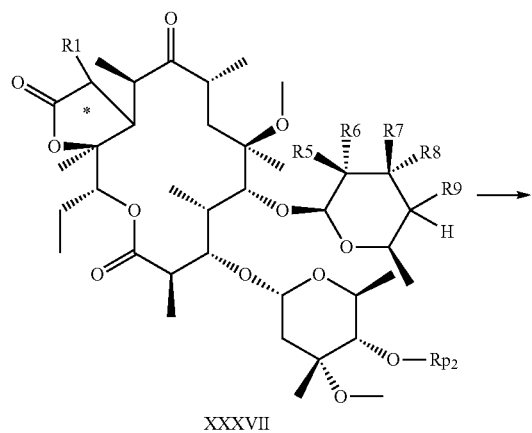

XXXVII

Compounds of formula Io may be obtained by reacting compound XXXIX with 2-chloroacetylchloride, 2-chloroacetic acid anhydride or 2-chloroacetic acid according to methods well known for the esterification of hydroxyl groups to give compounds of formula XL (Rb=$CH_2Cl$). This compound is then reacted with an appropriate nucleophile such as for example dimethylamine or morpholine to give compounds of formula Io (scheme 12). Compounds of formula In are obtained in a similar way by reacting compound XXXIX with acroyl chloride to give compound XL wherein Rb is CH=$CH_2$ followed by a reaction with an appropriate nucleophile such as for example, dimethylamine or morpholine to give compounds of formula In. Compounds of formula Im are prepared from compounds XXXIX by reaction of an acid anhydride, an acid chloride or an carboxylic acid in the presence of a base and an appropriate activating agent.

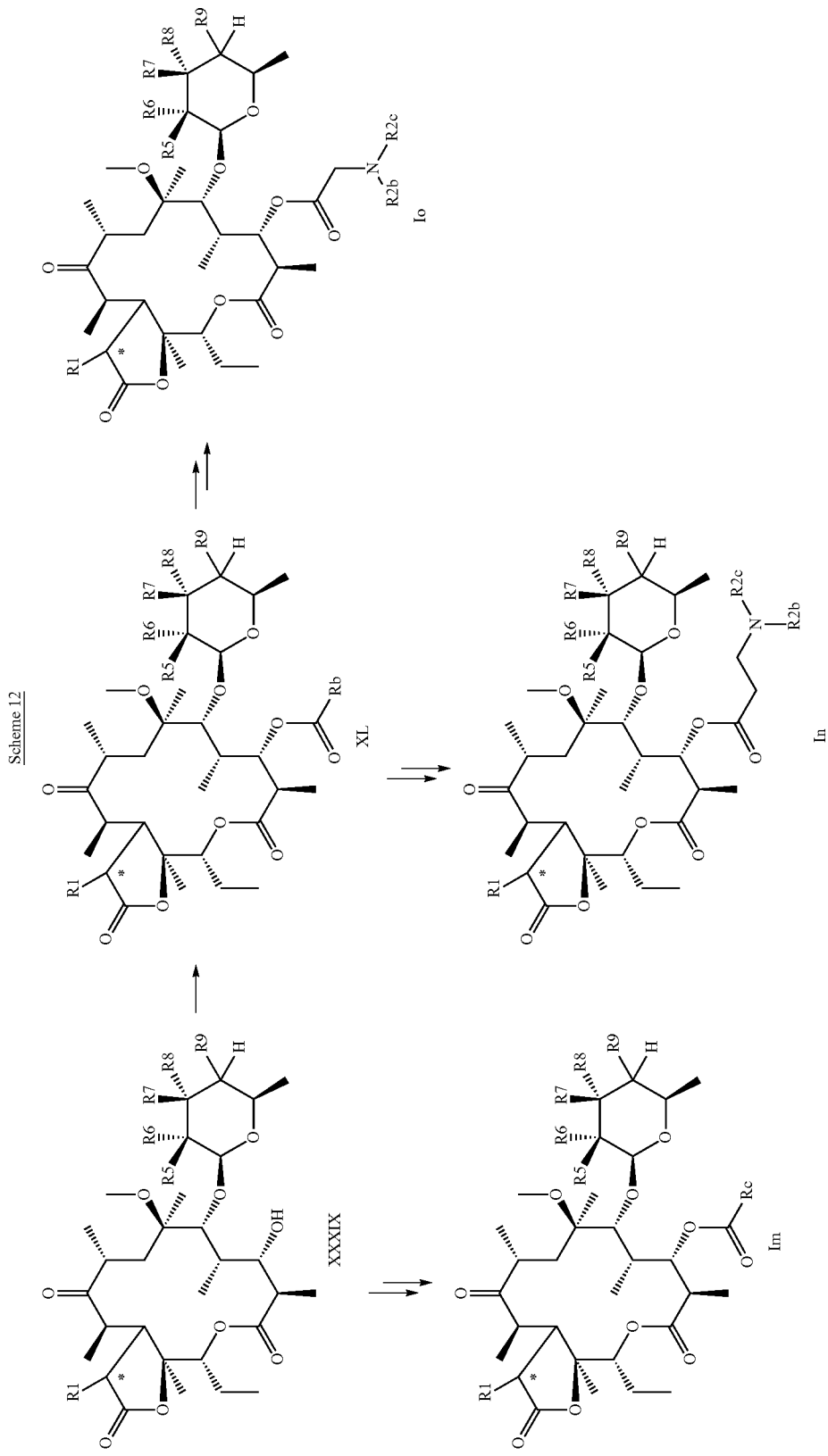

Compounds of formula Ip may be prepared according to any of the schemes 1-14 as summarized in scheme 13 starting from compound XLI (Bioorg. Med. Chem. 2007, 15, 3266).

Alternatively compounds of formula Ip are prepared starting from compound XXVIII according to similar methods as described in Bioorg. Med. Chem. 2007, 15, 3266.

Scheme 13
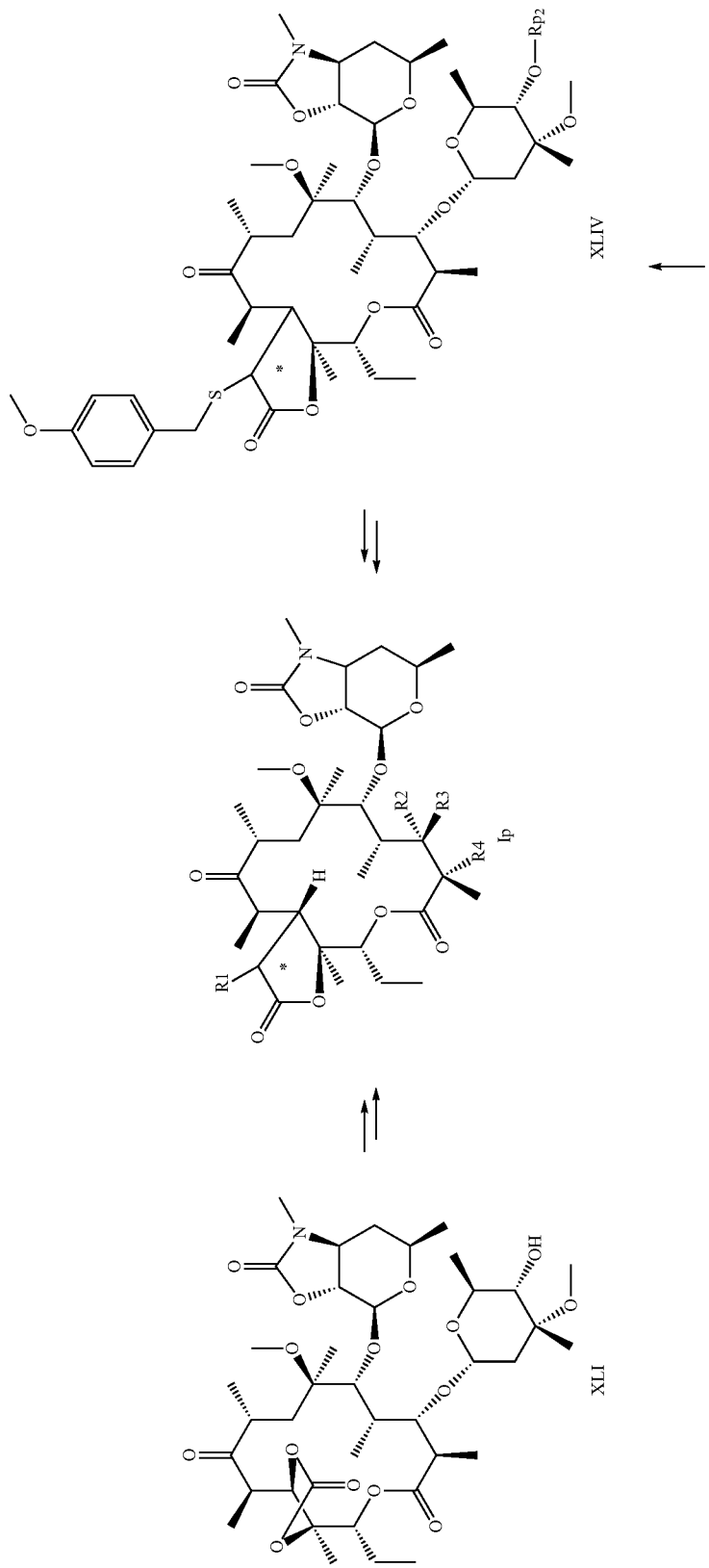

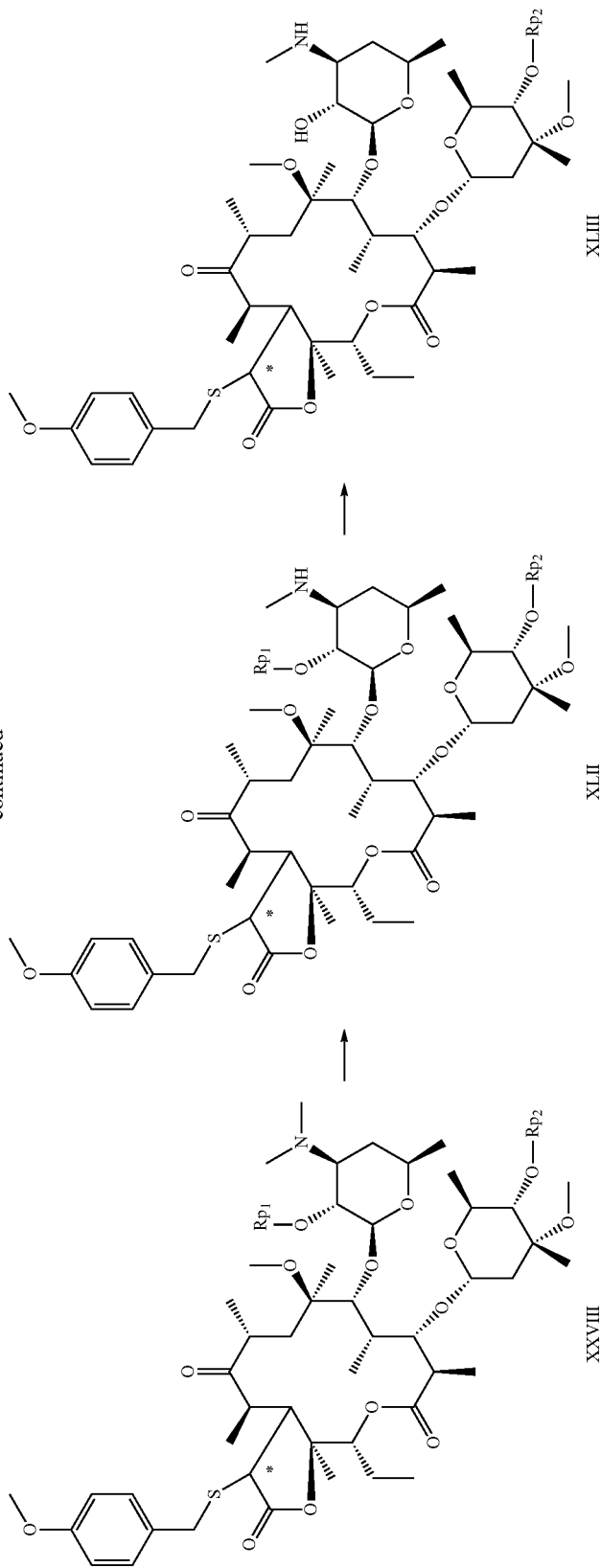

Compounds of formula Iq can e.g. be prepared by treatment of compounds of formula Ia (compound of formula I protecting group(s) can be removed following standard procedures also described in T. W. Green et al.

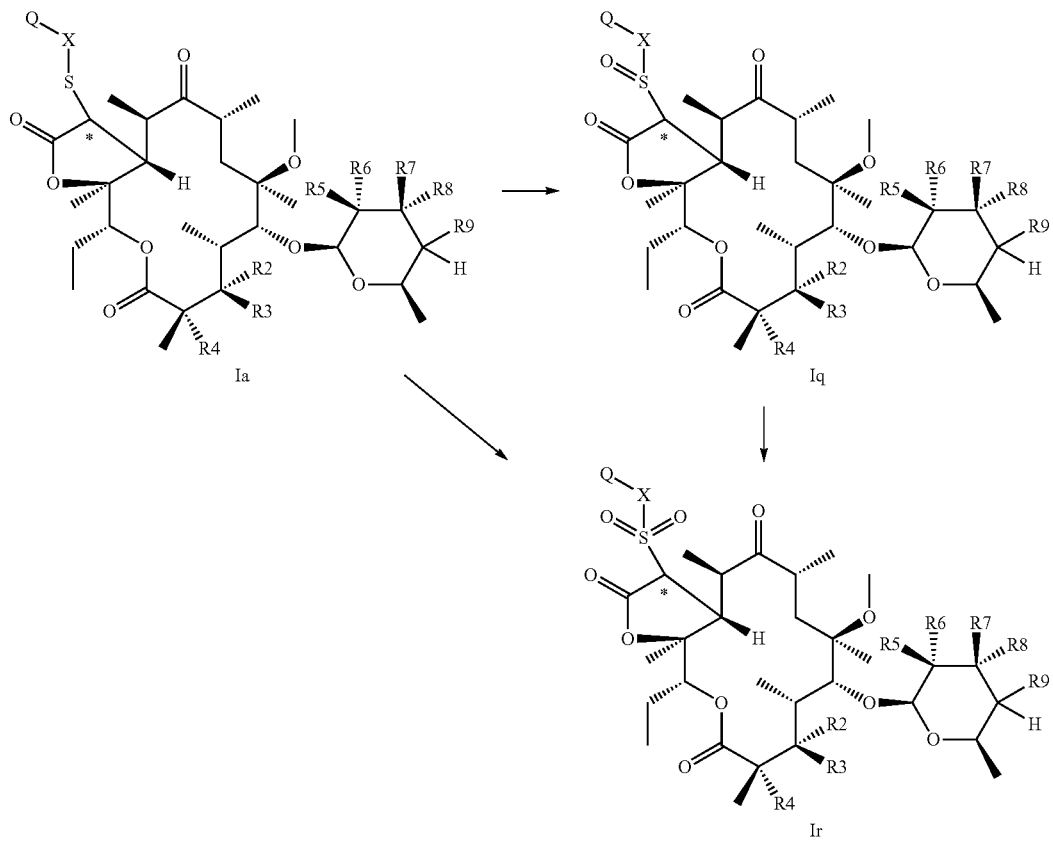

Scheme 14 where Y=S) with 2 to 2.5 equivalents of 3-chloroperoxybenzoic acid (mCPBA) and 4 to 5 equivalent of $NaHCO_3$ in a solvent such as methylene chloride at temperatures ranging from 0° C. to room temperature for 1 to 3 hours. The N-oxide which is formed on the dimethylamino group of the sugar residue during the reaction is reduced at work-up by treating the organic phase with an aqueous solution of sodium pyrosulfite at room temperature during 5 minutes to 24 hours to give the desired compounds of formula Iq as a mixture of diastereoisomers. Alternatively, if appropriate, the N-oxide is reduced by catalytic hydrogenation according to standard procedures. Compounds of formula Iq can be further oxidised as described above but at room temperature during 1 to 48 hours to give, after reduction of the N-oxide, compounds of formula Ir. Compounds Ir can also be obtained in one step from compounds of formula Ia by using 3.5 to 10 equivalents of the oxidising agent and 7 to 20 equivalent of $NaHCO_3$ at temperatures ranging from 0° C. to room temperature during 5 to 48 hours followed by the workup procedure described above (scheme 14).

In cases where Q is further substituted with oxidation sensitive substituents like amino groups, these substituents might need to be protected before submitting the sulfide Ia to oxidation. Suitable protecting groups commonly known in the art can be introduced according to standard procedures described in T. W. Green et al., Protective Groups in Organic Synthesis, John Wiley & Sons, 1999. After oxidation, the It is understood that individual modifications described in the schemes 1-14 can be performed sequentially with the same molecule to give compounds of general formula I i.e. modifications in positions 2 and 3 of the macro lactone ring as described for example in scheme 9 can be combined with a modification of the sugar moiety as described for example in scheme 4. To avoid interference with functional groups a person skilled in the art will carry out the reactions in an appropriate order and protect and subsequently deprotect functional groups if necessary.

It is further understood that R1 in compounds of e.g. formula I or I-A, and of intermediates like those mentioned above can be further modified. For example an ester group can be hydrolyzed and the resulting acid can be coupled with an amine to form a amide according to methods well known in the art.

The present invention accordingly furthermore relates to a process for the manufacture of a compound of formula (I) according to the present invention, comprising a) converting a macrolide compound having the formula (II)

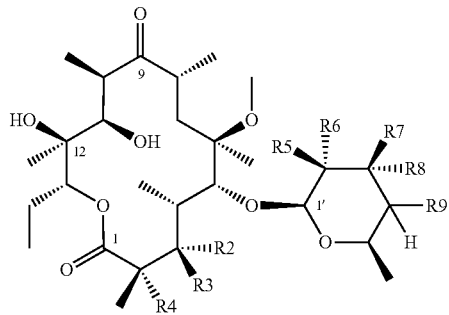

II wherein the groups R2 to R9 are defined above, after appropriate protection where necessary, in a manner known per se to a compound of formula IV

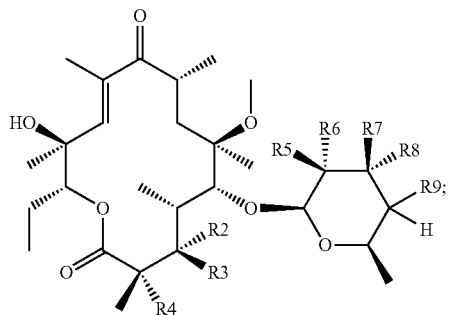

IV b) converting said compound of formula IV in a manner known per se to a compound of formula VI

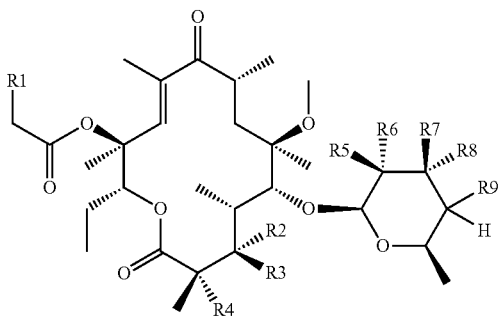

VI wherein R1 is as defined above or is a group of formula —S-Rp$_3$ wherein Rp$_3$ is a sulfur protecting group, c) reacting said compound of formula VI in an aprotic solvent with an alkali metal base to form a compound of formula VII

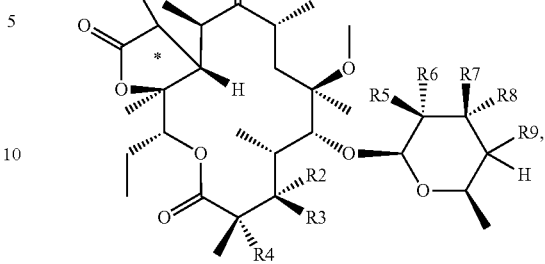

VII wherein R1 to R9 have the meaning above, and removing any protecting groups where necessary to form the compound of formula I, with the proviso that in case that R1 is S-Rp$_3$ the compound of formula VII is into the disulfide derivative of formula VIII (in case R2 represents a cladinosyl group in the presence of a molecular sieve) before removing any hydroxyl protecting groups present

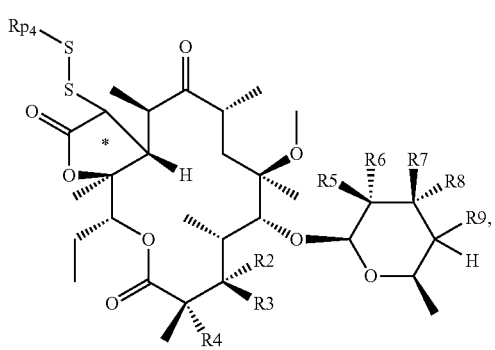

VIII wherein Rp$_4$ is $C_1$-$C_4$alkyl, in particular methyl, or 3-nitro-2-pyridinyl, which compound is treated with a reducing agent, in particular trialkyl phosphine or triaryl phosphine, in a solvent, in particular aqueous acetone, aqueous DMF, aqueous dioxane or aqueous THF, to give a compound of formula IX

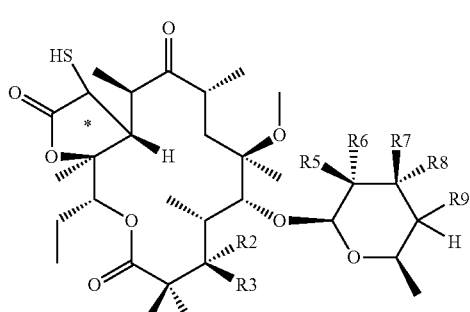

IX wherein R2 to R9 have the above meaning, which compound is then reacted with a compound of formula Q-X-Lg, wherein Q and X are as defined in formula (I) and Lg is a leaving group or, when X represents a carbonyl or sulfonyl group, a vinyl group, to give the compound of formula VII wherein R1 is as defined above.

The compound of formula (II)

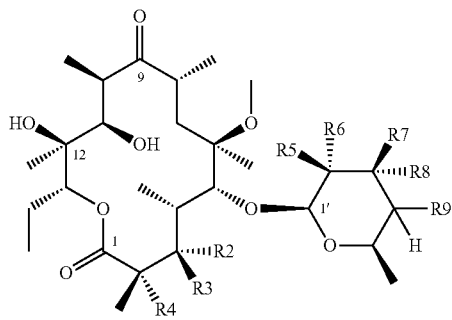

wherein the groups R2 to R9 are as defined above; the compound of formula IV

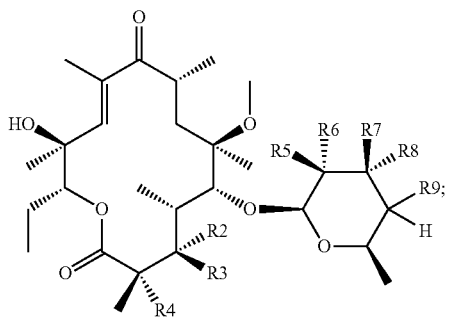

wherein the groups R2 to R9 are as defined above; the compound of formula VI

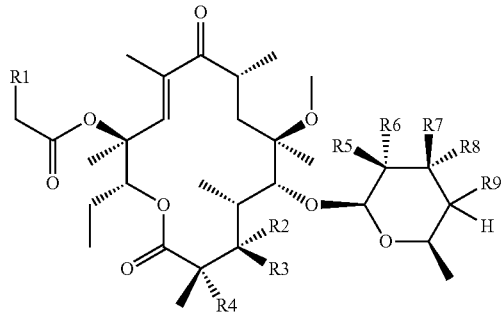

wherein R1, R2 to R9 are as defined above; as well as the compound of formula (VIII)

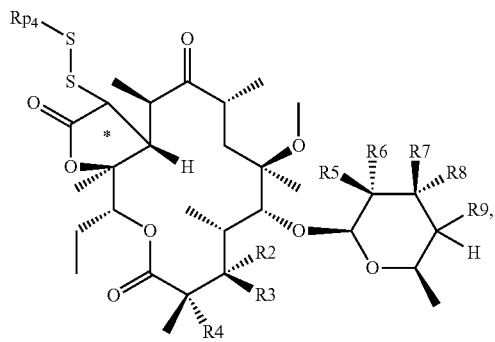

wherein $Rp_4$ R2 to R9 are as defined above;

are accordingly valuable intermediates for the manufacture of the compounds according to formula (I) and are a further subject of the invention.

The invention furthermore relates to a process for the manufacture of a compound of formula I according to claim 1, comprising converting a compound selected from the compounds of the formula

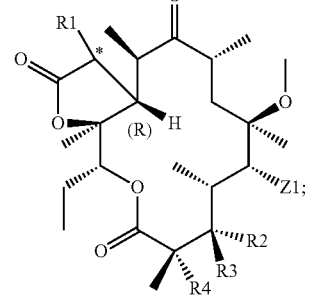

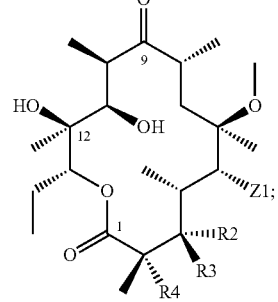

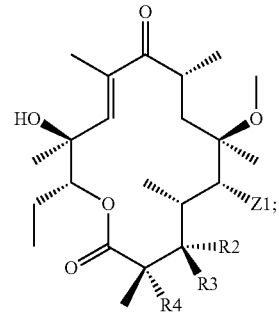

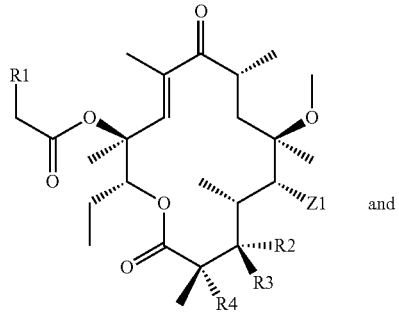

and

-continued

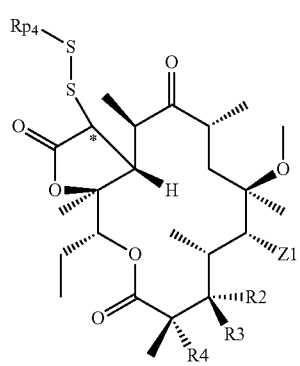
VIII-1 wherein
R1, R2, R3 and R4 have one of the meanings defined above and
Z1 is a group of formula

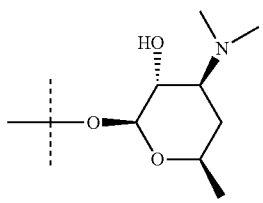

wherein

represents the linking bond;
in a manner known per se to the compound of formula (I) according to invention.

Said compounds of formula (I-1); (II-1); (IV-1); (VI-1) or (VII-1) are obtained according to the following process scheme:

a) converting a macrolide compound having the formula (II-1)

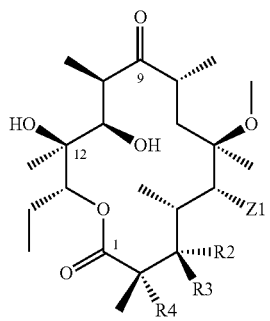
II-1 wherein the groups R2 to R4 and Z1 are defined as in claim 41, after appropriate protection
where necessary, in a manner known per se to the corresponding compound of formula (IV-1)

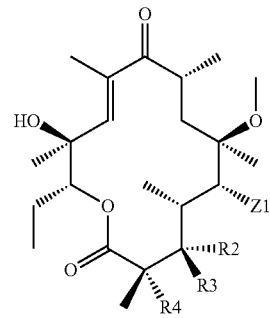
IV-1 b) converting said compound of formula (IV-1) in a manner known per se to the corresponding compound of formula (VI-1)

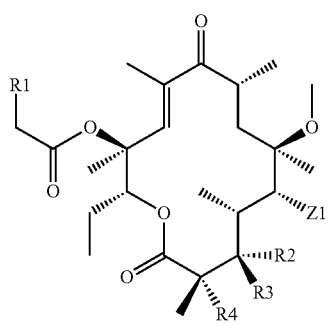
VI-1 wherein R1 is as defined in claim 1 or is a group of formula —S-Rp$_3$ wherein Rp$_3$ is a sulfur protecting group, c) reacting said compound of formula (VI-1) in an aprotic solvent with an alkali metal base to form the corresponding compound of formula (VII-1)

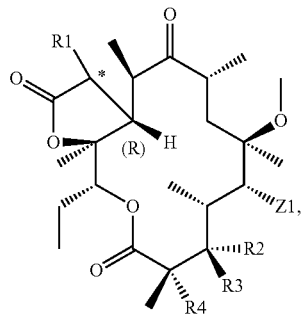
VII-1 and removing any protecting groups where necessary to form the compound of formula (I-1), or, in case that R1 is S-Rp$_3$, transforming the compound of formula (VII-1) into the disulfide derivative of formula (VIII-1) (in case R2 is a cladinoyl group in the presence of a molecular sieve) before removing any hydroxyl protecting groups

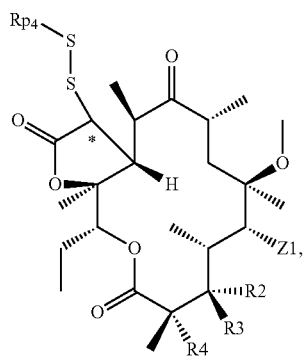

VIII-1 wherein $Rp_4$ is $C_1$-$C_4$alkyl, in particular methyl, or 3-nitro-2-pyridinyl, and are further processed in the way described above.

The following examples are given to further illustrate the invention and are not to be construed as in any way limiting the scope of the present invention.

EXAMPLES

The following examples are given to further illustrate the invention and are not to be construed as in any way limiting the scope of the present invention.

| Example | Structure |
|---|---|
| 1 | 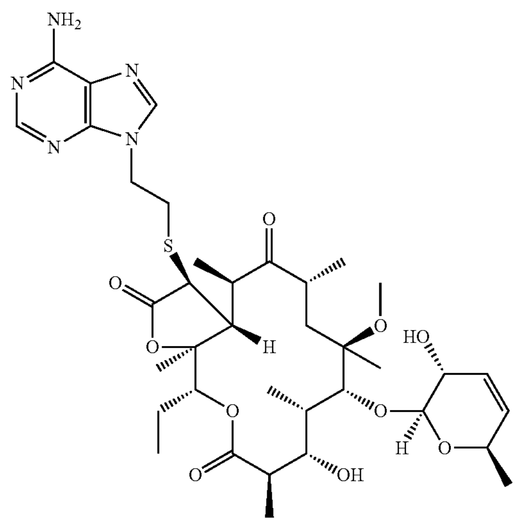 [SMILES: CC[C@H]1OC(=O)[C@H](C)[C@@H](O)[C@H](C)[C@@H](O[C@@H]2O[C@H](C)C=C[C@H]2O)[C@](C)(OC)C[C@@H](C)C(=O)[C@H](C)[C@H]2[C@H](SCCn3cnc4c(N)ncnc43)C(=O)O[C@@]21C] |
| 2 | 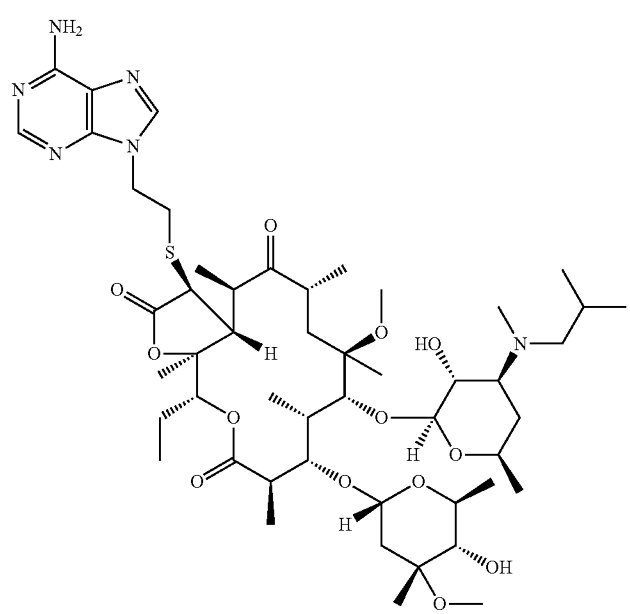 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CC(C)C)[C@H]2O)[C@](C)(OC)C[C@@H](C)C(=O)[C@H](C)[C@H]2[C@H](SCCn3cnc4c(N)ncnc43)C(=O)O[C@@]21C] |

-continued
| Example | Structure |
|---------|-----------|
| 3 | 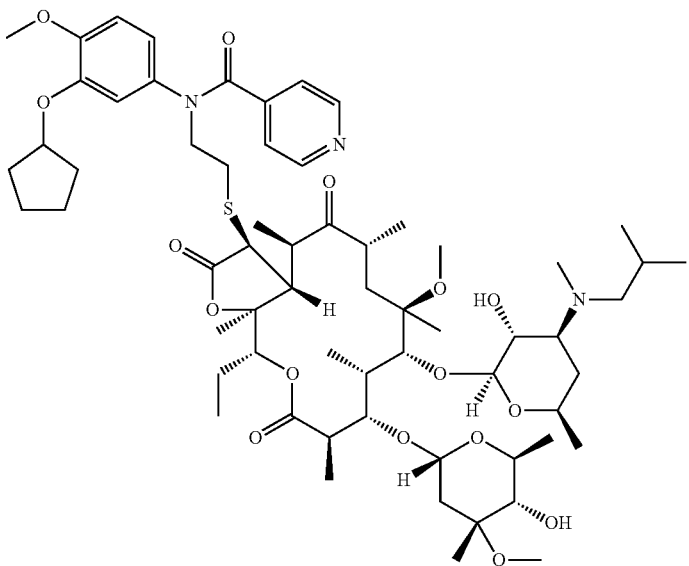 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CC(C)C)[C@H]2O)[C@](C)(OC)C[C@@H](C)C(=O)[C@H](C)[C@H]2[C@H](SCCN(C(=O)c3ccncc3)c3ccc(OC)c(OC4CCCC4)c3)C(=O)O[C@@]21C] |
| 4 | 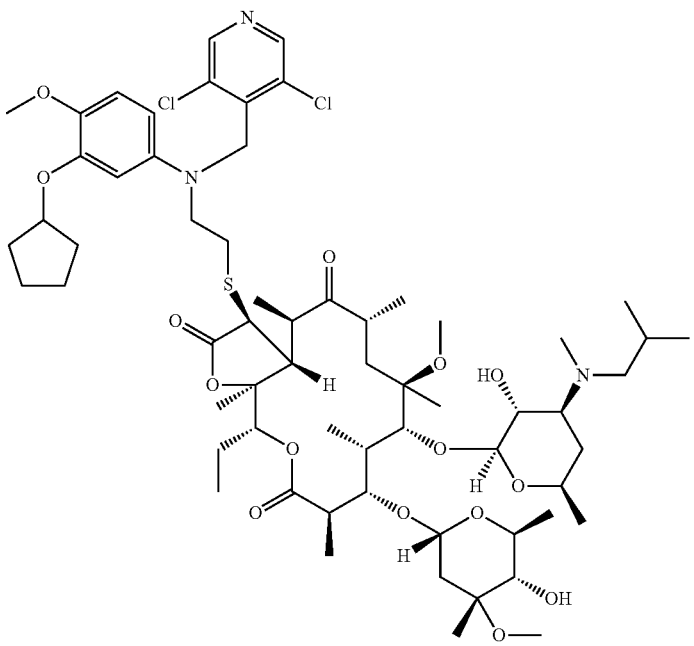 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CC(C)C)[C@H]2O)[C@](C)(OC)C[C@@H](C)C(=O)[C@H](C)[C@H]2[C@H](SCCN(Cc3c(Cl)cncc3Cl)c3ccc(OC)c(OC4CCCC4)c3)C(=O)O[C@@]21C] |

| Example | Structure |
|---------|-----------|
| 5 | 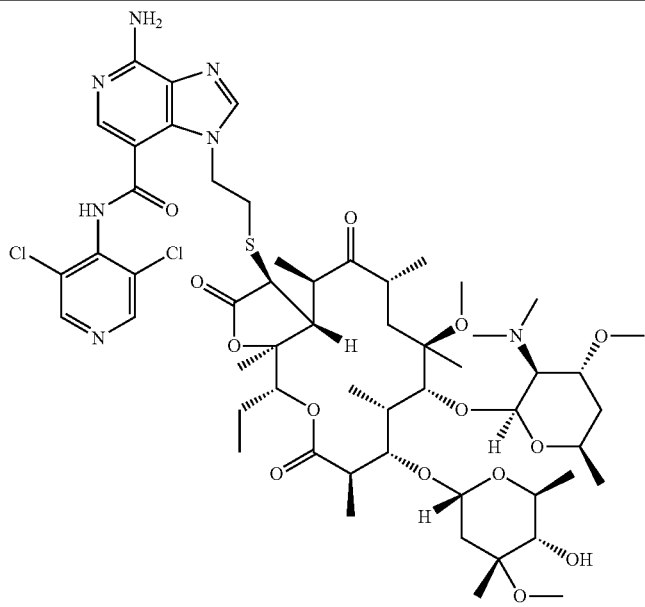 |
| 6 | 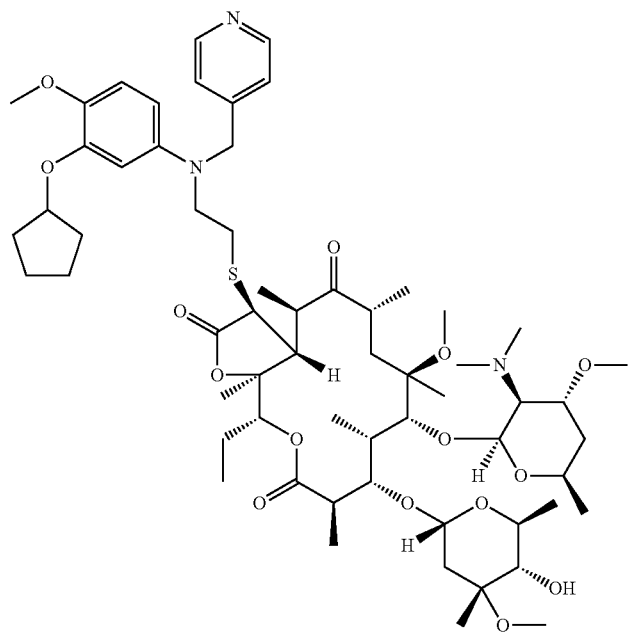 |

| Example | Structure |
|---|---|
| 7 | 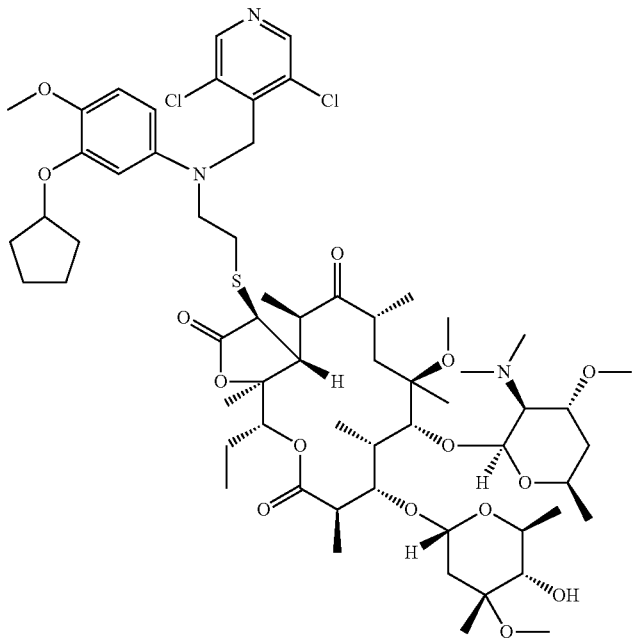 |
| 8 | 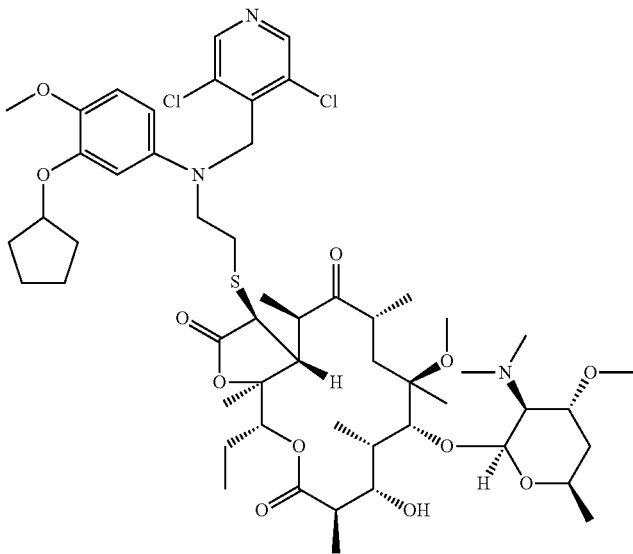 |

-continued
| Example | Structure |
|---------|-----------|
| 9 | 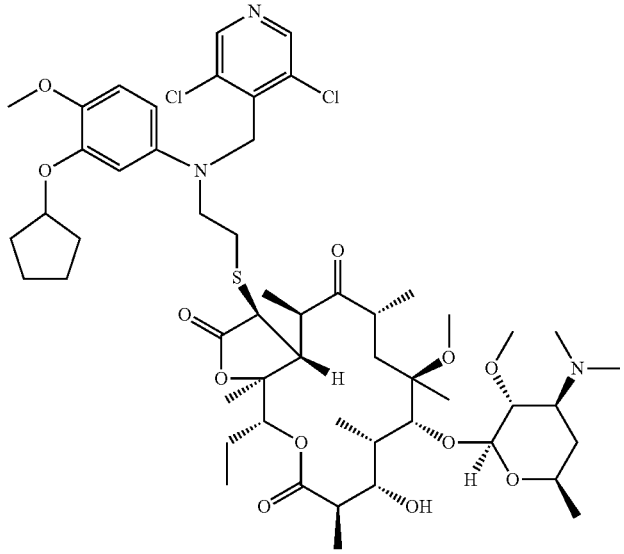 |
| 10 | 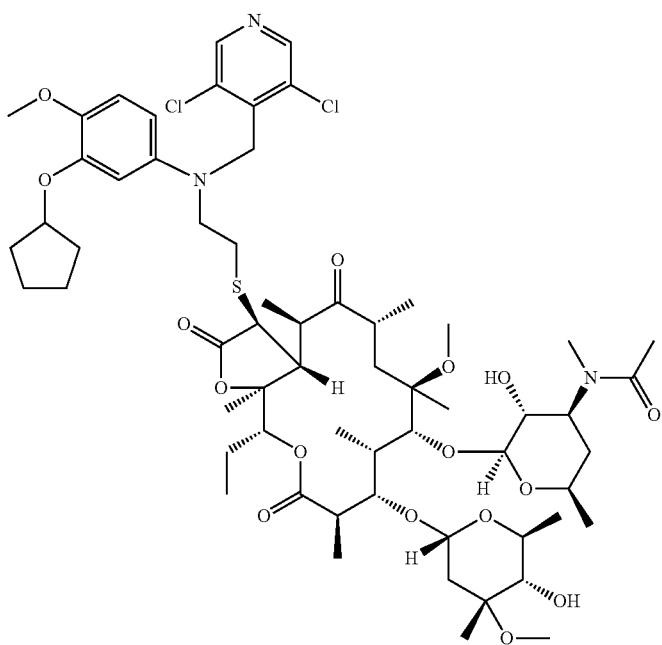 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C(C)=O)[C@H]2O)[C@](C)(OC)C[C@@H](C)C(=O)[C@H](C)[C@H]2[C@H](SCCN(Cc3c(Cl)cncc3Cl)c3ccc(OC)c(OC4CCCC4)c3)C(=O)O[C@@]21C] |

-continued
| Example | Structure |
|---------|-----------|
| 11 | 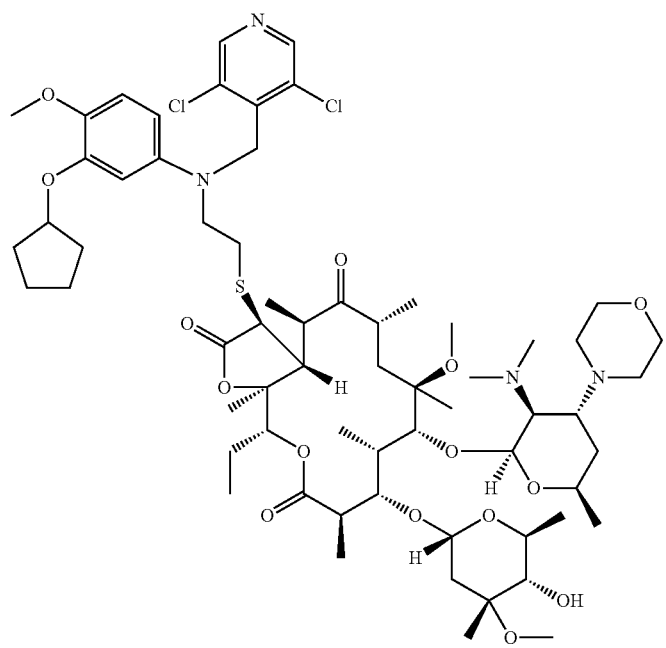 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@@H](N3CCOCC3)[C@@H]2N(C)C)[C@](C)(OC)C[C@@H](C)C(=O)[C@H](C)[C@H]2[C@H](SCCN(Cc3c(Cl)cncc3Cl)c3ccc(OC)c(OC4CCCC4)c3)C(=O)O[C@@]21C] |
| 12 | 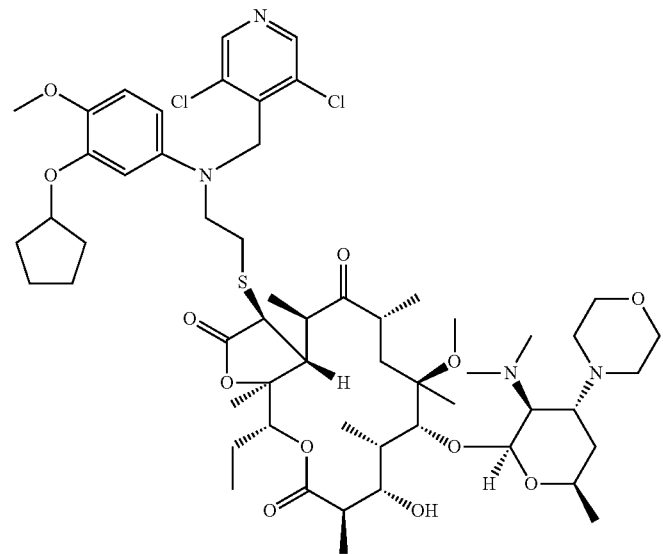 [SMILES: CC[C@H]1OC(=O)[C@H](C)[C@@H](O)[C@H](C)[C@@H](O[C@@H]2O[C@H](C)C[C@@H](N3CCOCC3)[C@@H]2N(C)C)[C@](C)(OC)C[C@@H](C)C(=O)[C@H](C)[C@H]2[C@H](SCCN(Cc3c(Cl)cncc3Cl)c3ccc(OC)c(OC4CCCC4)c3)C(=O)O[C@@]21C] |

| Example | Structure |
|---|---|
| 13 | 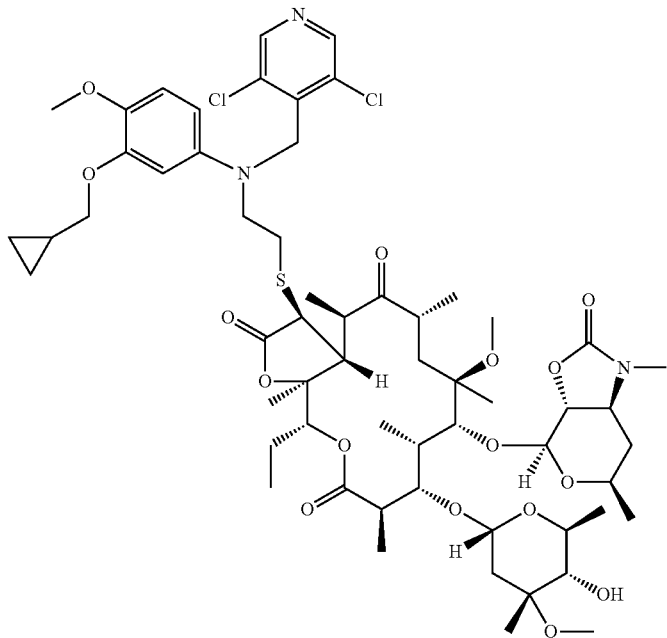 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H]3[C@H]2OC(=O)N3C)[C@](C)(OC)C[C@@H](C)C(=O)[C@H](C)[C@H]2[C@H](SCCN(Cc3c(Cl)cncc3Cl)c3ccc(OC)c(OCC4CC4)c3)C(=O)O[C@@]21C] |
| 14 | 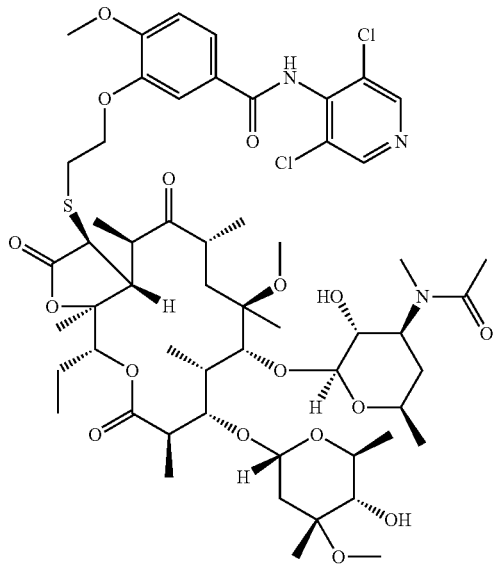 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C(C)=O)[C@H]2O)[C@](C)(OC)C[C@@H](C)C(=O)[C@H](C)[C@H]2[C@H](SCCOc3cc(C(=O)Nc4c(Cl)cncc4Cl)ccc3OC)C(=O)O[C@@]21C] |

-continued
| Example | Structure |
|---|---|
| 15 | 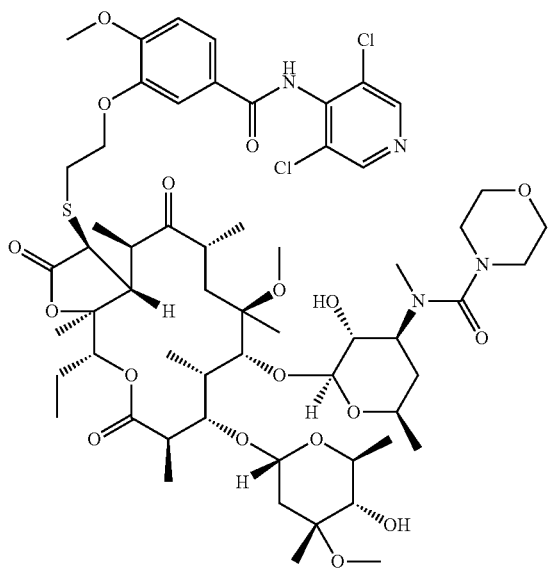 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C(=O)N3CCOCC3)[C@H]2O)[C@](C)(OC)C[C@@H](C)C(=O)[C@H](C)[C@H]2[C@H](SCCOc3cc(C(=O)Nc4c(Cl)cncc4Cl)ccc3OC)C(=O)O[C@@]21C] |
| 16 | 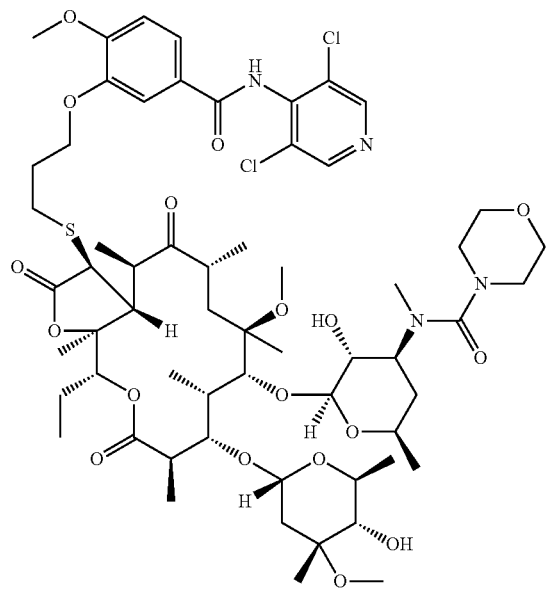 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C(=O)N3CCOCC3)[C@H]2O)[C@](C)(OC)C[C@@H](C)C(=O)[C@H](C)[C@H]2[C@H](SCCCOc3cc(C(=O)Nc4c(Cl)cncc4Cl)ccc3OC)C(=O)O[C@@]21C] |

-continued
| Example | Structure |
|---|---|
| 17 | 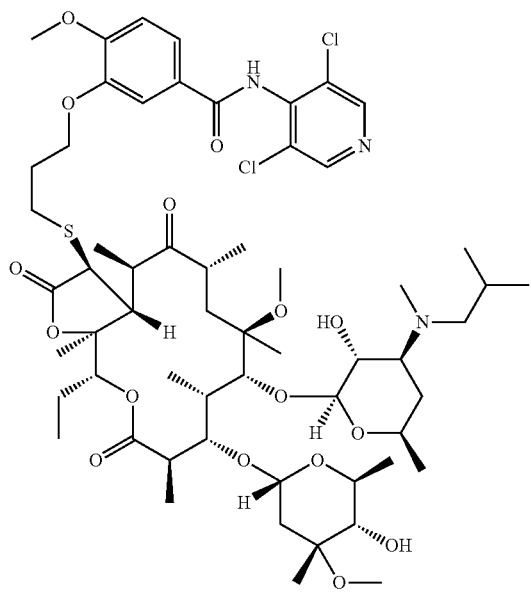 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CC(C)C)[C@H]2O)[C@](C)(OC)C[C@@H](C)C(=O)[C@H](C)[C@H]2[C@H](SCCCOc3cc(C(=O)Nc4c(Cl)cncc4Cl)ccc3OC)C(=O)O[C@@]21C] |
| 18 | 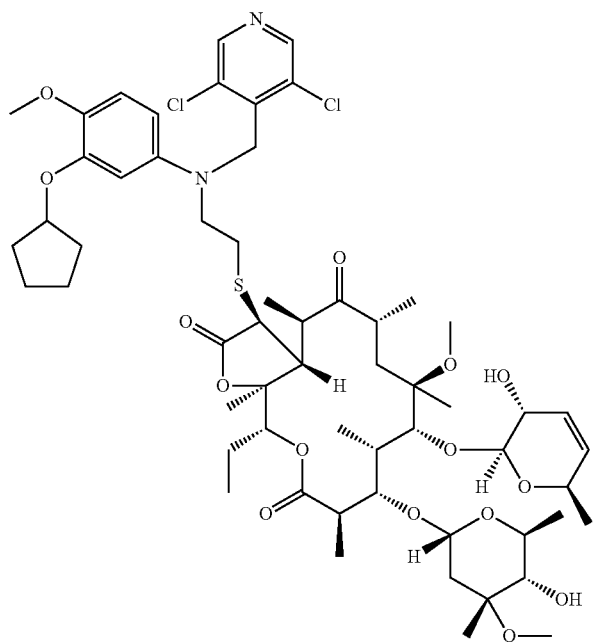 |

-continued

| Example | Structure |
|---------|-----------|
| 19 | 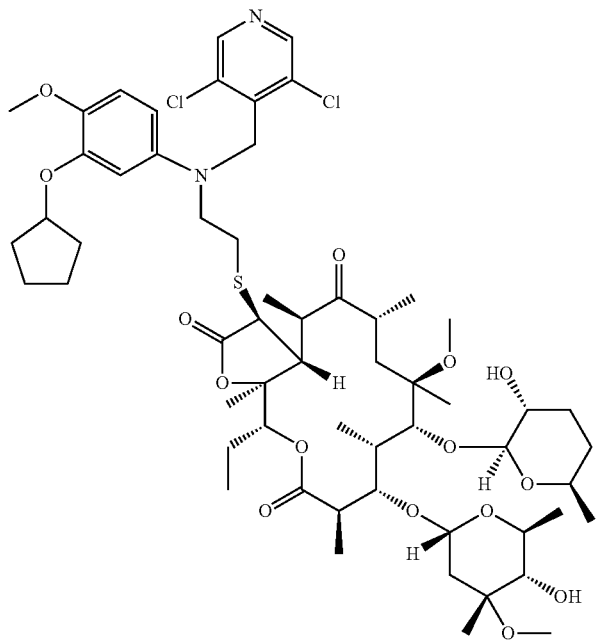 |
| 20 | 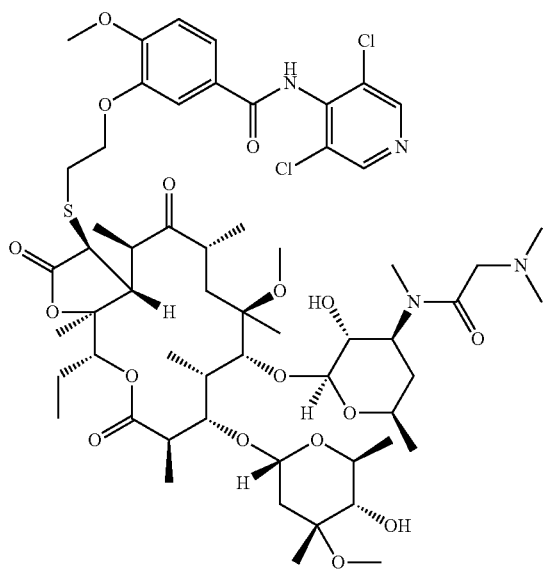 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C(=O)CN(C)C)[C@H]2O)[C@](C)(OC)C[C@@H](C)C(=O)[C@H](C)[C@H]2[C@H](SCCOc3cc(C(=O)Nc4c(Cl)cncc4Cl)ccc3OC)C(=O)O[C@@]21C] |

General remarks: MS spectra are measured using (A) a Micromass Waters ZQ system with Masslynx software and (B) using a Q-T of-Ultima (Waters AG) equipped with the Waters Acquity-LC. The system is equipped with the standard Lockspray interface. Spectra are measured with +ESI ionization and a capillary voltage of +3.4 kV with internal calibration. Accurate masses are given with four decimal digits with consideration of the electron mass. Analytical HPLC: System Aa: column: Bischoff Prontosil 120-3-C18 SH 3 µm, 75×4.6 mm; flow: 1.2 mL/min; detection: ELSD, UV; mobile phase A: water+3% acetonitrile+0.1% TFA; mobile phase B: acetonitrile+0.1% TFA; gradient: 0-2 min constant 5% B; 2-5 min linear from 5% to 30% B; 5-18 min linear from 30% to 55% B; 18-23.5 min linear from 55% to 95% B; 23.5-35 min 95% B. System Ba: column: Agilent ZORBAX Eclipse plus C18, 5 µm, 250×4.6 mm; flow: 1.0 mL/min; detection: 220 nm; mobile phase A: water/acetonitrile/TFA 98.9/1/0.1 (v/v/v); mobile phase B: water/acetonitrile/TFA 1/98.9/0.1 (v/v/v); gradient: 0-5 min constant 0% B; 5-45 min linear from 0% to 100% B; 45-55 min 100% B. Preparative HPLC: System Ap: Column: YMC ODS-AQ, 120A, 5 µm, 50×20 mm; precolumn: YMC ODS-AQ, 120A, 5 µm, 10×20 mm; flow: 30 ml/min; injection: 500 µA; detection: ELSD; mobile phase A: water+0.1% HCOOH; mobile phase B: acetonitrile; gradient: linear form 10 to 95% acetonitrile in 4 min. System Bp: Column: YMC Pro C18, 50×21.1 mm; flow: 30 ml/min; detection: ELSD; mobile phase A: 20 mM aqueous Ammoniumacetate mobile phase B: acetonitrile; gradient: 0.2 min linear from 90% B to 95% B; 2-6 min constant 95% B. Abbreviations: HPLC for high performance liquid chromatography; DMSO for dimethylsulphoxide; DBU for diazabicycloundecane; DCM for dichloromethane; DMF for dimethylformamide; THF for tetrahydrofurane; DCC for dicyclohexylcarbodiimide; DMAP for 4-dimethylaminopyridine; EDC.HCl for N-(3-dimethylaminopropyl)-N'-ethylcarbodiimide hydrochloride; HATU for O-(7-Azabenzotriazol-1-yl)-N,N,N',N'-tetramethyluronium hexafluorophosphate; HOBt for 1-hydroxy-benzotriazol; MTBE for methyl tent-butyl ether TBDMSC1 for tert-butyl-dimethyl-silylchloride, TBAF for tetrabutylammoniumfluoride, MS for mass spectrometry; NMR for nuclear magnetic resonance; ESI for electrospray ionization.

Example 1

Preparation of I-1, compound of formula I where R1 is [2-(6-amino-9H-purin-9-yl)ethyl]thio, R2 is c-OH, R6 is hydroxy, R8 and R9 taken together with the bond between the carbon atoms to which they are linked form a double bond, and R3, R4, R5 and R7 are hydrogen.

A] Preparation of compound 1-A

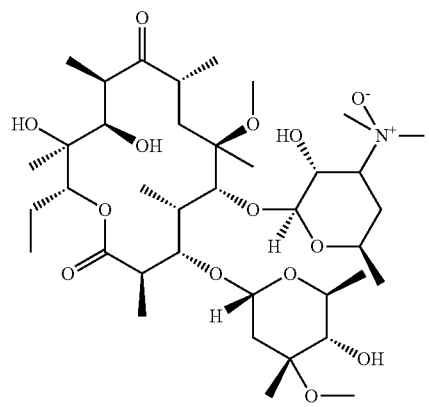 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)CC([N+](C)(C)[O-])[C@H]2O)[C@](C)(OC)C[C@@H](C)C(=O)[C@H](C)[C@@H](O)[C@]1(C)O]

To a solution of 30.0 g clarithromycin in 800 ml methanol are added 270 ml of a solution of hydrogen peroxide (10% in water) in three portions and the resulting suspension is stirred at 15° C. for 20 hours. The reaction mixture becomes clear. Methanol is removed in vacuo leading to precipitation of a white solid. The solid is isolated by filtration and dried to give 35.2 g of the crude product which is suspended in 200 ml of tert-butyl methyl ether. The suspension is stirred during three hours and then filtered. The solids are washed with 80 ml of tert-butyl methyl ether and dried in vacuo at 75° C. to give 28.4 g (92%) of the desired compound as white solid.

MS (ESI): 764.6 [MH]$^+$

Ret. Time (system Aa): 10.9 min.

B] Preparation of Compound 1-B

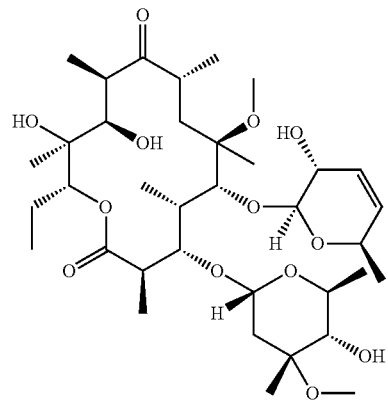 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C=C[C@H]2O)[C@](C)(OC)C[C@@H](C)C(=O)[C@H](C)[C@@H](O)[C@]1(C)O]

2 g of compound 1-A are heated to 160-180° C. under vacuum (~70 Pa) for 2 hours. The light yellow powder is subsequently dissolved in methanol and decolorized with charcoal to give a light grey solid. This solid is crystallized from 60 ml of a mixture of methanol and water (3:1) to give 620 mg of an off-white solid which is further purified by column chromatography on silica gel (DCM:MeOH 120:1 then 60:1) to give 420 mg (22%) of the desired product as a white solid.

MS (–ESI): 747.5 [MHCOO]$^-$

Ret. Time (system Aa): 17.2 min.

C] Preparation of Compound 1-C 1.6 ml (17 mmol; 4 eq.) acetic anhydride are added to a stirred solution of 3.0 g (4.24 mmol) of compound 1-B and 0.2 g (1.7 mmol, 0.4 eq.) DMAP in 100 ml dichloromethane and the mixture is stirred overnight at 32° C. Now additional 1.2 ml (12.2 mmol; 3 eq.) acetic anhydride and 1.0 ml triethylamine are added and the mixture is again stirred over night and subsequently diluted with 10 ml DCM. The organic layer is washed twice with 100 water, dried over Na$_2$SO$_4$ and evaporated in vacuo to give a light yellow solid. The crude product is triturated with 6 ml MTBE for 1 hour, filter and dried to give 2.5 g (74%) of the desired product as white solid.

MS (–ESI): 831.6 [MHCOO]$^-$

Ret. Time (system Aa): 23.4 min.

D] Preparation of Compound 1-D

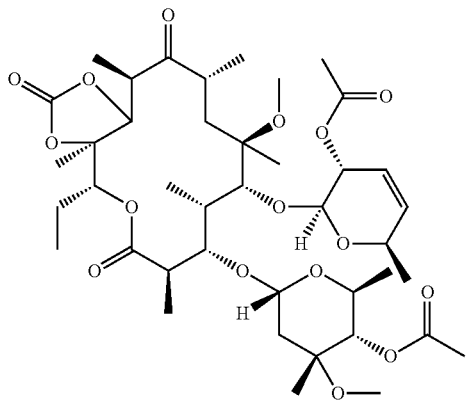 [SMILES: CC[C@H]1OC(=O)[C@H](C)[C@@H](O[C@H]2C[C@@](C)(OC)[C@@H](OC(C)=O)[C@H](C)O2)[C@H](C)[C@@H](O[C@@H]2O[C@H](C)C=C[C@H]2OC(C)=O)[C@](C)(OC)C[C@@H](C)C(=O)[C@H](C)C2OC(=O)O[C@@]21C]

400 mg (0.51 mmol) of compound 1-C are dissolved in 10 ml dry THF at −50° C. and treated dropwise with 0.9 ml of a 1 M solution of sodium bis(trimethylsilyl)amide in THF (0.91 mmol) over 5 min. After 40 min. at −50° C., 0.206 g (1.27 mmol) carbonyldiimidazole in 5 ml THF are added. The reaction mixture is stirred at −50° C. for 20 min, then warmed to 0° C. over a period of 15 min and kept at 0-3° C. for 5 hours. The reaction mixture is quenched with 10 ml of saturated aqueous $NH_4Cl$. The mixture is diluted with 40 ml water and the solution is extracted with three times 30 ml ethyl acetate. The combined organic layers are washed twice with 30 ml water and with 40 ml brine, dried over sodium sulfate and evaporated under reduced pressure to afford 410 mg of a light yellow solid. 230 mg of the crude product are purified by column chromatography on silica gel (hexane:ethyl acetate 4:1) to give 120 mg of the desired product as a white solid.

Ret. Time (system Aa): 23.0 min.

$^1$H-NMR ($CDCl_3$):(diagnostic signals only) 5.74 (d, 1H); 5.49 (d, 1H); 5.21 (m, 1H); 5.02 (d, 1H); 4.94 (d, 1H); 4.84 (d, 1H); 4.66 (d, 1H); 4.58 (s, 1H); 4.51 (m, 1H); 4.36 (m, 1H); 3.77 (d, 1H); 3.60 (d, 1H); 3.28 (s, 3H); 2.99 (s, 3H); 2.92 (m, 1H); 2.82 (m, 1H); 2.64 (m, 1H); 2.37 (d, 1H); 2.09 (s, 3H); 2.04 (s, 3H); 1.83 (m, 2H); 1.48 (s, 3H); 1.38 (s, 3H); 0.95 (d, 3H); 0.87 (t, 3H).

E] Preparation of Compound 1-E

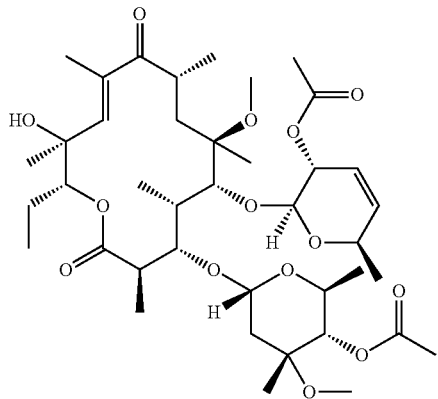 [SMILES: CC[C@H]1OC(=O)[C@H](C)[C@@H](O[C@H]2C[C@@](C)(OC)[C@@H](OC(C)=O)[C@H](C)O2)[C@H](C)[C@@H](O[C@@H]2O[C@H](C)C=C[C@H]2OC(C)=O)[C@](C)(OC)C[C@@H](C)C(=O)/C(C)=C/[C@]1(C)O]

180 mg (0.22 mmol) of compound 1-D and 0.1 ml (0.66 mmol) DBU dissolved in 15 ml toluene are heated to 100° C. for 24 h, cooled to room temperature and poured into 10 ml 0.5 M aqueous $NaH_2PO_4$. The aqueous layer is extracted twice with 10 ml ethyl acetate. The combined organic extracts are washed with 10 ml 0.5 M $NaH_2PO_4$, 10 ml water and twice with 10 ml brine, dried over $Na_2SO_4$ and concentrated to give the crude product as a light yellow foam. The crude product is purified by column chromatography on silica gel (DCM:ethyl acetate 10:1) to give 65 mg (38%) of the desired product.

MS (−ESI): 813.6 [MHCOO]$^-$
Ret. Time (system Aa): 22.8 min.

F] Preparation of Compound 1-F

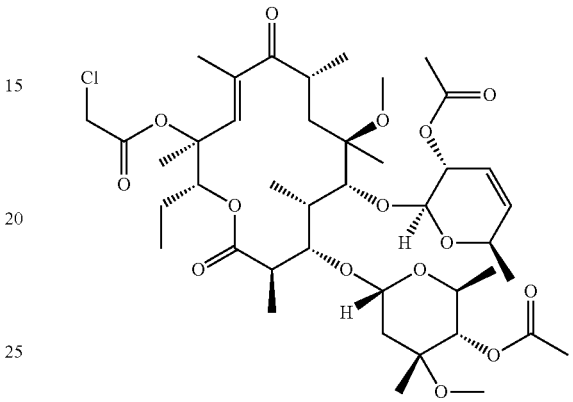

To a solution of 9.94 g (12.9 mmol) of compound 1-E, 0.6 g (4.9 mmol) 4-dimethylaminopyridine and 1.95 g of pyridine in 215 ml dichloromethane is added dropwise a solution of 4.42 g of chloroacetic acid anhydride (25.8 mmol) in 45 ml dichloromethane over 1 hour under nitrogen. The solution is stirred at room temperature for 3.5 hours. The reaction mixture is poured into 100 ml of saturated aqueous $NaHCO_3$. The aqueous layer is extracted twice with 400 ml dichloromethane. The combined organic layers were washed successively with 100 ml water and with 100 ml brine, dried over $Na_2SO_4$ and evaporated to give the crude product as a brown foam. The crude product is used without purification for the next step.

Ret. Time (system Aa): 24.3 min.

G] Preparation of Compound 1-G

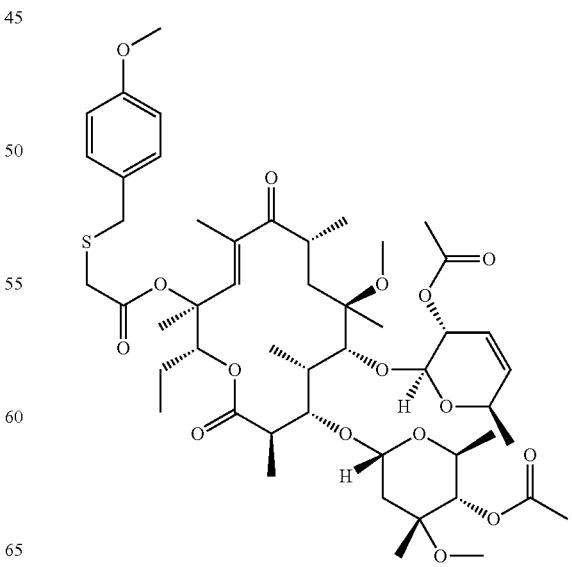

13.1 g of crude compound 1-F were dissolved under nitrogen in 370 ml acetone and 2.45 ml DBU, 117 mg sodium iodide and 2.52 g (4-methoxyphenyl)methanethiol were added in one portion. The reaction mixture is stirred under nitrogen at room temperature for 18 hours. Acetone is evaporated and the residue is taken up in 40 ml of DCM. The organic layer is washed with saturated aqueous ammonium chloride, water and brine, dried over $Na_2SO_4$ and evaporated in vacuo to give the crude product as a brown foam. The crude product is purified by column chromatography on silica gel (heptane:ethyl acetate 3:1→2:1) to give 9.89 g of the desired product as a white foam.

H] Preparation of Compound 1-H

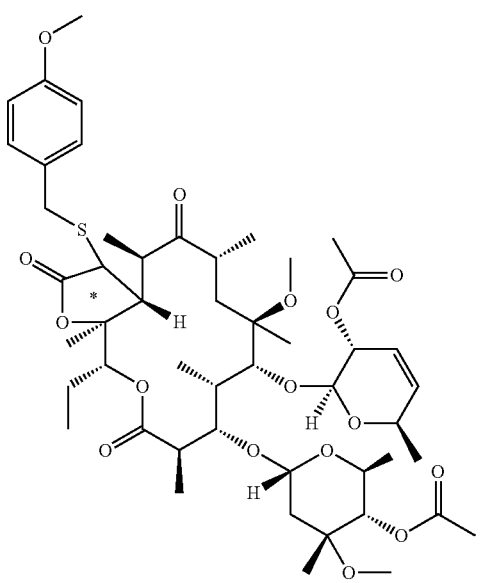 [SMILES: CC[C@H]1OC(=O)[C@H](C)[C@@H](O[C@H]2C[C@@](C)(OC)[C@@H](OC(C)=O)[C@H](C)O2)[C@H](C)[C@@H](O[C@@H]2O[C@H](C)C=C[C@H]2OC(C)=O)[C@](C)(OC)C[C@@H](C)C(=O)[C@H](C)[C@H]2C(SCc3ccc(OC)cc3)C(=O)O[C@@]21C]

0.804 g of compound of 1-G were dissolved under argon in 10 ml DMF and cooled with an ice bath. 0.0435 g sodium hydride oil dispersion (60%) were added and the dark red mixture is stirred during 3 hours at 0-5° C. Now 20 ml saturated aqueous $NH_4Cl$ were added and the mixture is extracted with 40 ml diethylether. The organic layer is washed with aqueous $NaHCO_3$ 5% and with brine. The aqueous layers were extracted with 40 ml diethylether and the combined organic layers were dried over $Na_2SO_4$ and evaporated in vacuo to afford the crude product. The crude product is purified by column chromatography on silica gel (heptane:ethyl acetate 3:1→2:1) to give 0.45 g (56%) of the desired product as a white foam.

$^1$H-NMR ($CDCl_3$):(diagnostic signals only) 7.36 (d, 2H); 6.87 (d, 2H); 5.79 (m, 1H); 5.54 (m, 2H); 5.25 (m, 1H); 4.95 (d, 1H); 4.90 (d, 1H); 4.69 (d, 1H); 4.56 (m, 1H); 4.40 (m, 1H); 4.36 (s, 1H); 4.14 (d, 1H); 4.09 (d, 1H); 3.83 (m, 1H); 3.81 (s, 3H); 3.67 (d, 1H); 3.31 (s, 3H); 3.12 (s, 3H); 2.99 (m, 1H); 2.84 (m, 1H); 2.52 (m, 2H); 2.39 (d, 1H); 2.12 (s, 3H); 2.07 (s, 3H); 1.93 (m, 2H); 1.45 (s, 3H); 1.39 (s, 3H).

I] Preparation of compound 1-I

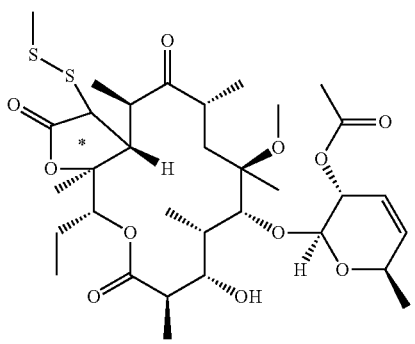 [SMILES: CC[C@H]1OC(=O)[C@H](C)[C@@H](O)[C@H](C)[C@@H](O[C@@H]2O[C@H](C)C=C[C@H]2OC(C)=O)[C@](C)(OC)C[C@@H](C)C(=O)[C@H](C)[C@H]2C(SSC)C(=O)O[C@@]21C]

0.45 g (0.47 mmol) of 1-H were dissolved in 10 ml DCM and 165 mg (0.84 mmol) dimethyl(methylthio) sulfonium tetrafluoroborate were added to the mixture and the reaction is stirred for 3 hours at room temperature. The reaction mixture is diluted with DCM and finished twice with 10 ml aqueous $NaHCO_3$ (5%), with 10 ml water and 10 ml brine, dried over $Na_2SO_4$, filtered and concentrated in vacuo to give 0.37 g of a brownish oil. The crude product is used without purification for the next step.

K] Preparation of Compound 1-K

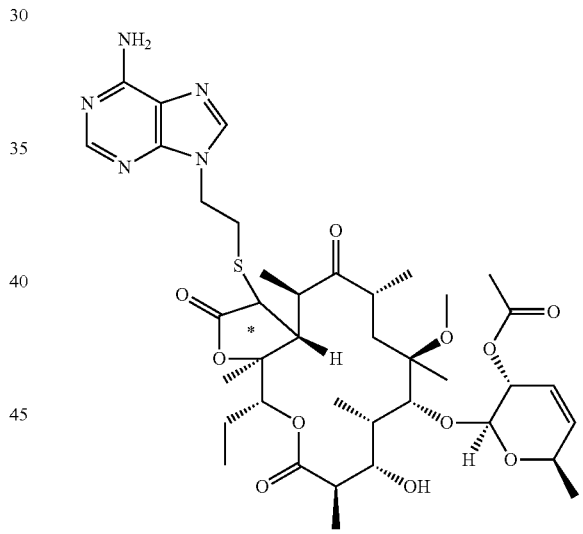

To a solution of 0.35 g of the product of example 1 step I dissolved in 10 ml DMF and 1 drop of water, 0.194 ml of tributylphosphine were added and the mixture is stirred for 2 hours at room temperature. Then 85 mg of 6-amino-9-(2-chloroethyl)-purine and 0.059 ml DBU were added to the solution. The reaction is stirred overnight at room temperature and concentrated in vacuo and the residue is taken up in 10 ml DCM. The organic layer is washed twice with aqueous $NaHCO_3$ (5%) and brine, dried over $Na_2SO_4$, filtered and concentrated in vacuo to give the crude product. The crude product is purified by flash chromatography on silica gel (DCM→DCM/MeOH/$NH_3$ 95:5:0.01) to give 31 mg of the desired product.

MS (ESI): 804.4 $[MH]^+$

L] Preparation of Compound I-1

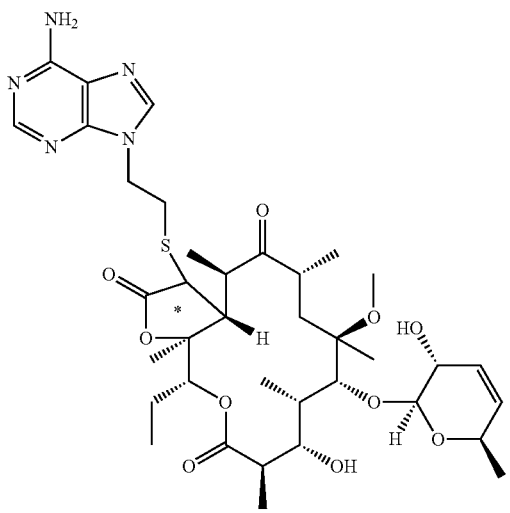 [SMILES: CC[C@H]1OC(=O)[C@H](C)[C@@H](O)[C@H](C)[C@@H](O[C@@H]2O[C@H](C)C=C[C@H]2O)[C@](C)(OC)C[C@@H](C)C(=O)[C@H](C)[C@H]2C(SCCn3cnc4c(N)ncnc43)C(=O)O[C@@]21C]

31 mg of the product of example 1 step K is dissolved in 1 ml methanol and 0.023 ml of DBU were added. The mixture is heated to reflux until no starting material remained (5 hours). Methanol is evaporated and the residue is taken up in 2 ml dichloromethane. The organic layer is washed with aqueous NaHCO$_3$ (5%) and brine, dried over Na$_2$SO$_4$, filtered and concentrated in vacuo to give the crude product. The crude product is purified by preparative HPLC (System Ap) to give 3.4 mg of the desired product as an adduct with formic acid.

MS: accurate mass (ESI): 762.3760 Da.

Ret. Time (system Ba): 22.4 min.

$^1$H-NMR (CDCl$_3$):(diagnostic signals only) 8.40 (s, 1H); 8.28 (s, 1H); 6.96 (s, br, 2H); 5.62-5.71 (m, 2H); 5.49 (dd, 1H); 4.71-4.79 (m, 1H); 4.52-4.62 (m, 3H); 4.32 (m, 1H); 4.13 (m, 1H); 3.82 (s, 1H); 3.62-3.71 (m, 1H); 3.56 (d, 1H); 2.97 (s, 3H); 2.04-2.05 (m, 1H); 1.89-1.99 (m, 2H); 1.51 (s, 3H); 1.41 (s, 3H); 0.85 (t, 3H).

Example 2

Preparation of I-2, compound of formula I where R1 is [2-(6-amino-9H-purin-9-yl)ethyl]thio, R2 is O-cladinosyl, R6 is hydroxyl, R7 is isobutyl-methyl-amino and R3, R4, R5, R8 and R9 are hydrogen.

A] Preparation of Compound 2-A

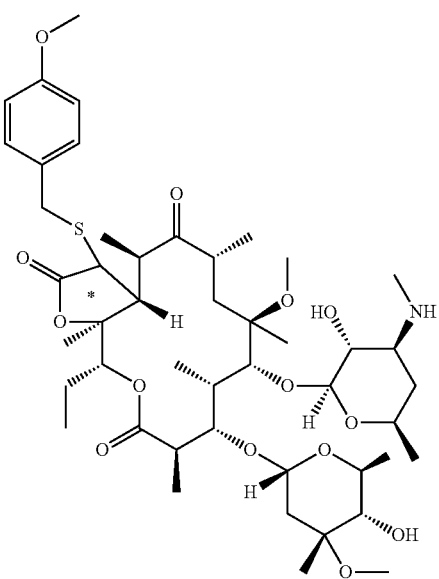 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](NC)[C@H]2O)[C@](C)(OC)C[C@@H](C)C(=O)[C@H](C)[C@H]2C(SCc3ccc(OC)cc3)C(=O)O[C@@]21C]

35 g (37.9 mmol) of the compound of formula VIIb where R1 is [(4-methoxy-phenyl)methyl]thio, R2 is O-cladinosyl, R6 is hydroxyl and R3, R4 and R5 are hydrogen (WO2006084410, example 10) were dissolved under nitrogen atmosphere in 500 ml methanol and 50 ml water. Then 15.7 g (189.4 mmol) sodium acetate and 38.5 g (151.48 mmol) of iodine were added. The reaction mixture is heated to 55° C. and irradiated with a high pressure mercury lamp (250W) for 3 hours. The reaction is quenched by adding 38 g of Na$_2$S$_2$O$_3$. Methanol is removed in vacuo and 500 ml of water is added to the residue. The mixture is extracted with three times 500 ml of DCM. The combined organic layers were washed twice with 500 ml water and twice with 500 ml brine, dried over Na$_2$SO$_4$ and concentrated in vacuo to give the crude product (33.5 g) as a yellow foam. The crude product is suspended in 150 ml of MTBE and the suspension is heated to reflux for 2 hours. 15 ml of DCM were added and stirring is continued for another 30 minutes. The warm suspension is filtered and the solids were washed with 100 ml MTBE and dried in vacuo to give 25.47 g of the desired product as an off-white solid.

Ret. Time (system Aa): 17.8 min.

MS (ESI): 910.3 [MH]$^+$

B] Preparation of Compound 2-B

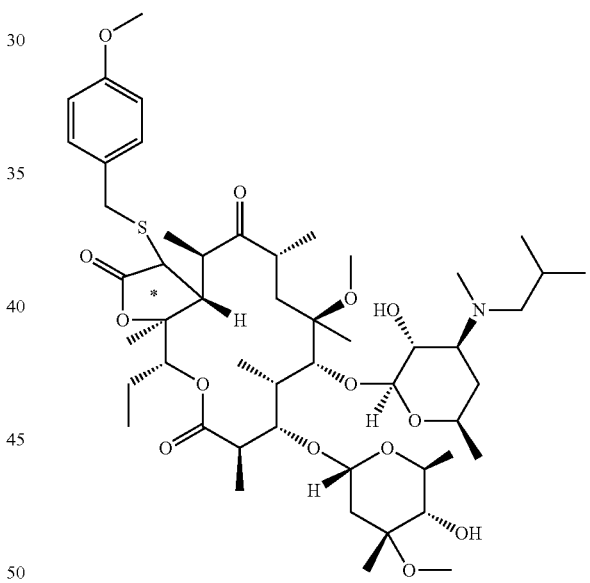

4.3 g (4.61 mmol) of the compound 2-A were dissolved under nitrogen atmosphere in 100 ml of methanol and 670 mg (9.21 mmol) of iso-butyraldehyde, 1.83 g (27.6 mmol) NaBH$_3$CN and 3 drops of acetic acid were added. The reaction mixture is stirred for 20 hours at room temperature and the solvent is removed under reduced pressure. The residue is taken up in 120 ml DCM and the organic layer is washed three times with 150 ml brine, dried over Na$_2$SO$_4$ and concentrated in vacuo to give the crude product as a light yellow foam. The crude product is purified by flash chromatography on silica gel (DCM/MeOH/NEt$_3$ 500:12:3) to give 3.75 g of the desired product as a white foam.

Ret. Time (system Aa): 20.4 min.

MS (ESI): 966.4 [MH]$^+$

C] Preparation of Compound 2-C

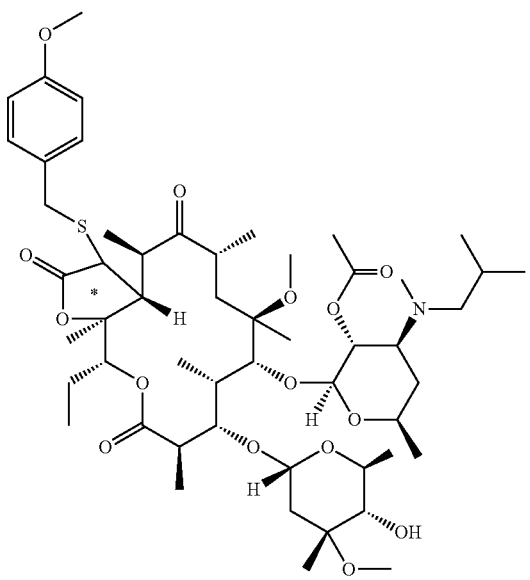 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CC(C)C)[C@H]2OC(C)=O)[C@](C)(OC)C[C@@H](C)C(=O)[C@H](C)[C@H]2C(SCc3ccc(OC)cc3)C(=O)O[C@@]21C]

3.65 g (3.69 mmol) of the product of example 2 step B were dissolved under nitrogen atmosphere in 25 ml DCM and 0.7 ml (7.37 mmol) acetic acid anhydride were added. The reaction mixture is stirred for 16 hours at room temperature. The solution is diluted with 100 ml DCM and the organic layer washed with 100 ml of water and 100 ml of brine, dried over $Na_2SO_4$ and concentrated in vacuo to give 3.79 g (99%) of the desired product as a white foam.

Ret. Time (system Aa): 21.2 min.
MS (ESI): 1008.4 $[MH]^+$
$^1$H NMR ($CDCl_3$): 7.32 (d, 2H); 6.83 (d, 2H); 5.48 (d, 1H); 4.87 (d, 1H); 4.72 (t, 1H); 4.53 (d, 1H); 4.31 (s, 1H); 4.07 (q, 2H); 3.95 (m, 1H); 3.78-3.74 (m, 4H); 3.57 (d, 1H); 3.44 (m, 1H); 3.34 (s, 3H); 3.10-2.87 (m, 5H); 2.79 (m, 1H); 2.43-2.62 (m, 3H); 2.32 (d, 1H); 2.27-2.06 (m, 7H); 2.01 (s, 3H); 1.86 (m, 2H); 1.72-1.44 (m, 6H); 1.41 (s, 3H); 1.37-1.14 (m, 14H); 1.14-0.98 (m, 7H); 0.96-0.72 (m, 12H).

D] Preparation of Compound 2-D

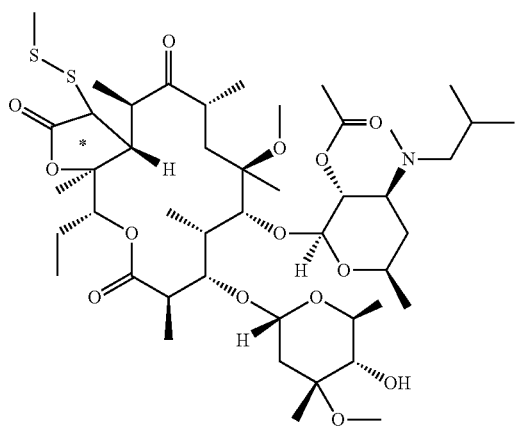 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CC(C)C)[C@H]2OC(C)=O)[C@](C)(OC)C[C@@H](C)C(=O)[C@H](C)[C@H]2C(SSC)C(=O)O[C@@]21C]

1.0 g (0.99 mmol) of 2-C were dissolved in 20 ml DCM and 233 mg (1.19 mmol) dimethyl(methylthio)sulfonium tetrafluoroborate and 12 g molecular sieves (4A) were added to the mixture and the reaction is stirred for 7 hours at room temperature. The reaction mixture is diluted with DCM and washed with 10 ml water and with 10 ml aqueous $NaHCO_3$ (5%), dried over $Na_2SO_4$, filtered and concentrated in vacuo to give the desired product as a foam. The crude product is used without purification for the next step.

MS (ESI): 934.6 $[MH]^+$

E] Preparation of Compound 2-E

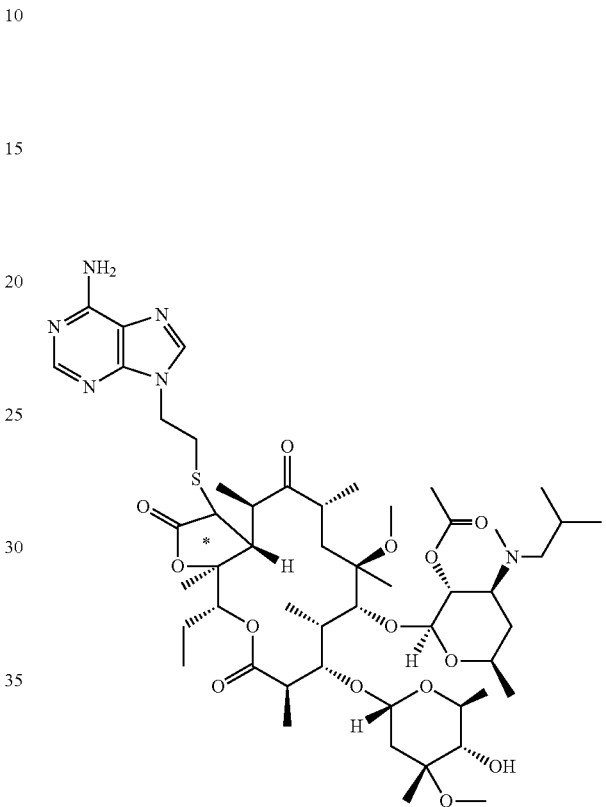

To a solution of 0.2 g of compound 2-D dissolved in 10 ml DMF and 1 drop of water, 0.105 ml of tributylphosphine are added and the mixture is stirred at room temperature until no starting material remained. Then 46.5 mg of 6-amino-9-(2-chloroethyl)-purine and 0.032 ml DBU are added to the solution. The reaction is stirred overnight at room temperature and concentrated in vacuo and the residue is taken up in 10 ml DCM. The organic layer is washed twice with 10 ml aqueous $NaHCO_3$ (5%) and twice with 10 ml brine, dried over $Na_2SO_4$, filtered and concentrated in vacuo to give the crude product. The crude product is partially purified by flash chromatography on silica gel (DCM/MeOH 95:5) to give 270 mg of the desired product which is used in the next step without further purification.

MS (ESI): 525.6 $[MH_z]^{++}$

F] Preparation of Compound I-2

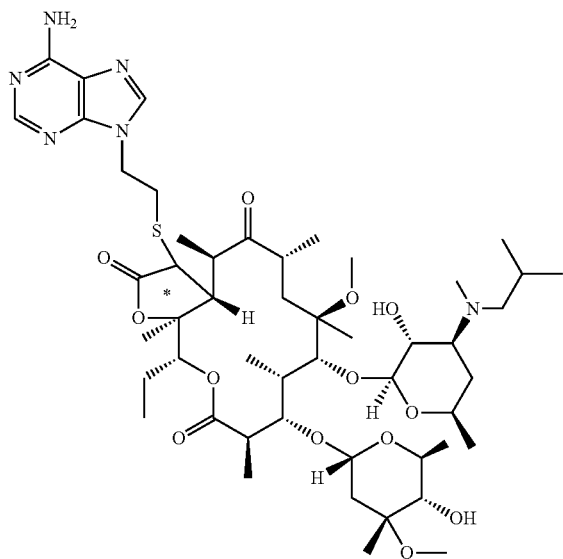 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CC(C)C)[C@H]2O)[C@](C)(OC)C[C@@H](C)C(=O)[C@H](C)[C@H]2C(SCCn3cnc4c(N)ncnc43)C(=O)O[C@@]21C]

260 mg of the partially purified product of example 2 step E is dissolved in 5 ml methanol. The mixture is stirred for three days at room temperature and for another 4 days at 40° C. Methanol is evaporated and the crude product is purified by preparative HPLC (System Ap) to give 28 mg of the desired product as a white solid.

MS: accurate mass (ESI): 1007.5750 Da.
Ret. Time (system Ba): 27.1 min.
$^1$H-NMR (DMSO-$d_6$) (diagnostic signals only): 8.24 (s, 1H); 8.14 (s, 1H); 7.21 (s, br, 2H); 5.22 (dd, 1H); 4.73 (d, 1H); 4.58 (m, 1H); 4.41-4.53 (m, 4H); 4.03 (m, 1H); 3.69 (m, 1H); 3.60 (dd, 2H); 3.42 (m, 1H); 3.21 (s, 3H); 3.04-3.12 (m, 3H); 2.91 (s, 3H); 0.76 (t, 3H).

Example 3

Preparation of I-3, compound of formula I where R1 is [2-[(3cyclopentyloxy-4-methoxy-phenyl)-(pyridin-4-yl-carbonyl)-amino]ethyl]thio, R2 is O-cladinosyl, R6 is hydroxyl, R7 is isobutyl-methyl-amino and R3, R4, R5, R8 and R9 are hydrogen.

A] Preparation of Compound 3-A

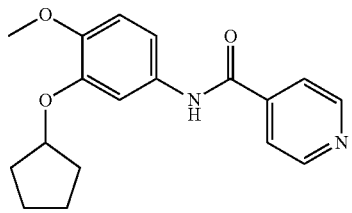 [SMILES: COc1ccc(NC(=O)c2ccncc2)cc1OC1CCCC1]

7.0 g (33.8 mmol) of 3-cyclopentyloxy-4-methoxy-phenylamine (Garcia et al., JOC, 2005, 70, p 1050) are dissolved in 150 ml of DCM. The solution is cooled to 0° C. and 5.74 g (40.5 mmol) isonicotinoyl chloride in 50 ml DCM are added to the solution. A precipitate is formed. The reaction mixture is subsequently stirred at room temperature during two hours. A solution of 2.7 g NaOH in 100 ml water is added to the reddish reaction mixture. The organic layer is separated, dried over Na$_2$SO$_4$ and evaporated. The crude product is purified by flash chromatography on silica gel (ethyl acetate/n-hexane 2:1) to afford 7.2 g (62%) of the desired product. MS (ESI): 313.1.

B] Preparation of Compound 3-B

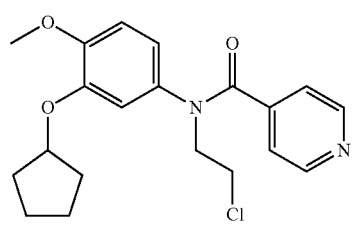 [SMILES: COc1ccc(N(CCCl)C(=O)c2ccncc2)cc1OC1CCCC1]

3.0 g (9.6 mmol) of the product of example 3 step A (3-A) are dissolved in 50 ml 1-bromo-2-chloroethane and 5.33 g (95 mmol) of potassium hydroxide are added to the solution. The reaction mixture is stirred at room temperature over night and then heated to 60° C. for four hours. The reaction mixture is cooled to room temperature and 50 ml water are added. The mixture is extracted with 50 ml of DCM. The organic layer is washed with water and brine, dried over Na$_2$SO$_4$ and evaporated. The crude product is purified by flash chromatography on silica gel (ethyl acetate/n-hexane 1:1) to afford 1.3 g (43%) of the desired product as a yellow oil.

$^1$H-NMR (DMSO-$d_6$): 8.45 (d, 2H); 7.21 (d, 2H); 6.8 (m, 3H); 4.63 (m, 1H); 4.13 (t, 2H); 3.76 (t, 2H); 3.66 (s, 3H); 1.4-1.8 (m, 8H).

C] Preparation of Compound 3-C

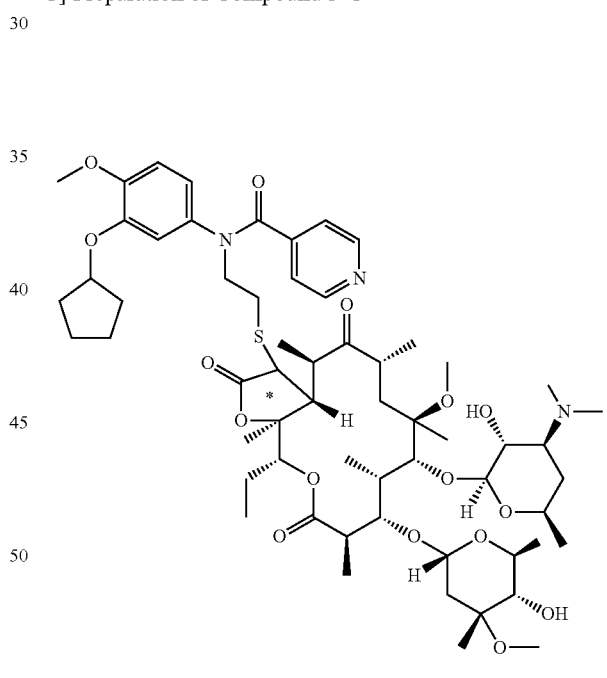

The title compound 3-C is prepared starting from N-(2-chloroethyl)-N-(3-cyclopentyloxy-4-methoxy-phenyl)-isonicotinamide (3-B) and compound of formula VIII where Rp$_4$ is methyl, R2 is O-cladinosyl, R6 is O—Rp$_1$, R7 is dimethyl-amino and R3, R4, R5, R8 and R9 are hydrogen and Rp$_1$ is acetyl (WO2006084410, example 4) following the procedures described in WO2006084410, example 4.

MS: accurate mass (ESI): 1141.6073 Da.

D] Preparation of Compound 3-D

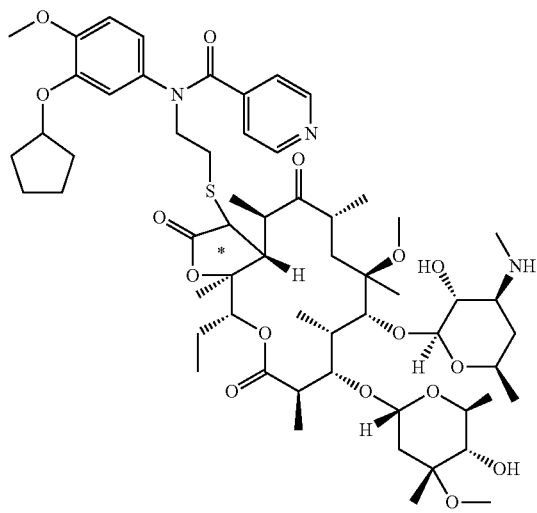 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](NC)[C@H]2O)[C@](C)(OC)C[C@@H](C)C(=O)[C@H](C)[C@H]2C(SCCN(C(=O)c3ccncc3)c3ccc(OC)c(OC4CCCC4)c3)C(=O)O[C@@]21C]

0.27 g (0.24 mmol) of the compound of formula 3-C (example 3, step C) is dissolved under nitrogen atmosphere in 40 ml methanol and 4 ml water. Then 0.097 g (1.18 mmol) sodium acetate and 0.24 g (0.95 mmol) of iodine are added. The reaction mixture is heated to 40° C. and irradiated with a high pressure mercury lamp (250W) for 2 hours. The reaction is quenched by adding an aqueous solution of $Na_2S_2O_3$. Methanol is removed in vacuo and 100 ml of water is added to the residue. The mixture is extracted with three times 100 ml of DCM. The combined organic layers are washed with 100 ml water and with 100 ml brine, dried over $MgSO_4$ and concentrated in vacuo to give the crude product (0.15 g) as an off-white solid. The crude product is used directly for the next step.

Ret. Time (system Aa): 12.8 min.
MS (ESI): 565.3 $[MH_z]^{++}$

E] Preparation of, Compound I-3

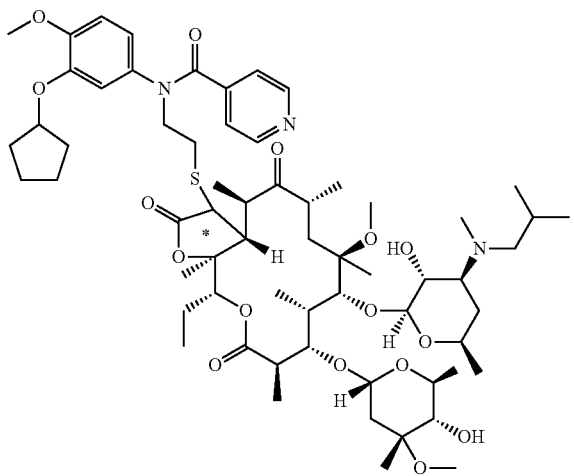 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CC(C)C)[C@H]2O)[C@](C)(OC)C[C@@H](C)C(=O)[C@H](C)[C@H]2C(SCCN(C(=O)c3ccncc3)c3ccc(OC)c(OC4CCCC4)c3)C(=O)O[C@@]21C]

0.15 g (0.13 mmol) of the compound 3-D are dissolved under nitrogen atmosphere in 15 ml of methanol and 19.2 mg (0.27 mmol) of iso-butyraldehyde, 50.1 mg (0.8 mmol) $NaBH_3CN$ and a drop of acetic acid are added. The reaction mixture is stirred for 48 hours at room temperature and the solvent is removed under reduced pressure. The residue is taken up in water and the aqueous layer is extracted with 3*50 ml DCM. The combined organic layers are washed with 100 ml water and 100 ml brine, dried over $Na_2SO_4$ and concentrated in vacuo to give the crude product as a light yellow foam. The crude product is purified by flash chromatography on silica gel (DCM/MeOH 50:1) to give 96 mg of the desired product as an off-white foam. The product is further purified by preparative HPLC (System Ap).

Ret. Time (system Aa): 15.4 min.
Ret. Time (system Ba): 31.8 min.
MS (ESI): 593.2 $[MH_z]^{++}$ $^1$H-NMR (CDCl$_3$): (diagnostic signals only, product contains some formic acid) 8.46 (d, 2H); 7.22 (d, 2H); 6.68 (m, 2H); 6.61 (s, 1H); 5.43 (dd, 1H); 4.91 (d, 1H); 4.55-4.65 (m, 3H); 4.38 (s, 1H); 4.28 (m, 2H); 4.01 (m, 1H); 3.79 (s, 3H); 3.70 (d, 1H); 3.61 (m, 1H); 3.48 (m, 1H); 3.31 (s, 3H); 3.21-3.32 (m, 2H); 3.10 (s, 3H); 2.55 (m, 2H); 0.85 (t, 3H).

Example 4

Preparation of I-4, compound of formula I where R1 is [2-[(3-cyclopentyloxy-4-methoxy-phenyl)-(3,5-dichloropyridin-4-yl-methyl)-amino]ethyl]thio, R2 is O-cladinosyl, R6 is hydroxyl, R7 is isobutyl-methyl-amino and R3, R4, R5, R8 and R9 are hydrogen.

A] Preparation of Compound 4-A

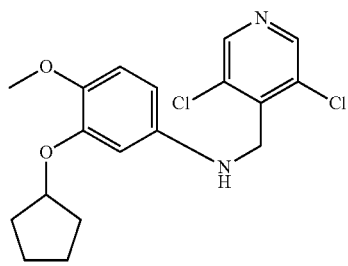 [SMILES: COc1ccc(NCc2c(Cl)cncc2Cl)cc1OC1CCCC1]

1.408 g (6.48 mmol) of 3-cyclopentyloxy-4-methoxy-phenylamine (Garcia et al., JOC, 2005, 70, p 1050) is dissolved in 20 ml toluene and 1.197 g (6.6 mmol) 3,5-dichloro-4-pyridinecarboxaldehyde, 3.6 ml (25.9 mmol) triethylamine and 1.85 ml (32.4 mmol) acetic acid are added. The mixture is stirred at 25° C. for 2 hours and then 1.629 g (25.9 mmol) $NaBH_3CN$ are added and the mixture is stirred for at 25° C. for one hour. The solvent is evaporated and the crude product is purified by flash chromatography on silica gel (petroleum ether/ethyl acetate 15:1) to give 1.98 g (82%) of the desired product as a light yellow solid.

$^1$H NMR (DMSO-d6): 8.61 (s, 2H); 6.70 (d, 1H); 6.30 (d, 1H); 6.15 (dd, 1H); 5.55 (t, 1H); 4.65 (m, 1H); 4.36 (d, 2H); 3.59 (s, 3H); 1.77-1.81 (m, 2H); 1.64-1.67 (m, 4H); 1.53-1.56 (m, 2H).

B] Preparation of Compound 4-B

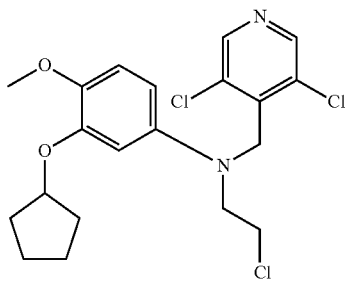 [SMILES: COc1ccc(N(CCCl)Cc2c(Cl)cncc2Cl)cc1OC1CCCC1]

1.9 g (4.96 mmol) of the compound 4-A are dissolved in 20 ml methanol and 5.8 g of a solution of chloroacetaldehyde (40% in water; 29.7 mmol, 6 eq), 1.87 g (77.4 mmol, 6. eq) of NaBH$_3$CN and 0.44 ml (7.69 mmol) of acetic acid are added. The mixture is stirred at 28° C. for 5 hours. Then the solvent is removed under reduced pressure and the residue is dissolved in 20 ml water and 40 ml dichloromethane. The mixture is separated and the aqueous phase is extracted with 30 ml DCM. The combined organic layers are washed with 30 ml water and with 30 ml brine, dried over Na$_2$SO$_4$ and evaporated in vacuo. The crude product is purified by flash chromatography on silica gel (petroleum ether/ethyl acetate 15:1 and 10:1) to afford 1.6 g (72%) of the desired product as a light yellow solid. $^1$H NMR (DMSO-d6): 8.59 (s, 2H); 6.77 (d, 1H); 6.40 (s, 1H); 6.38 (d, 1H); 4.66 (m, 1H); 4.65 (s, 2H); 3.62 (s, 3H); 3.60 (t, 2H); 3.55 (t, 2H); 1.51-1.65 (m, 8H).

C] Preparation of Compound 4-C

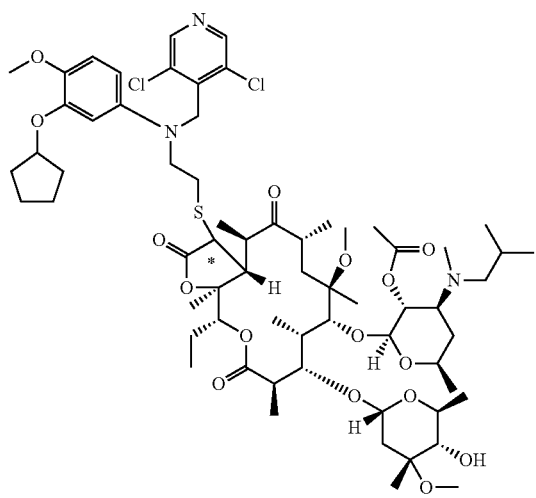 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CC(C)C)[C@H]2OC(C)=O)[C@](C)(OC)C[C@@H](C)C(=O)[C@H](C)[C@H]2C(SCCN(Cc3c(Cl)cncc3Cl)c3ccc(OC)c(OC4CCCC4)c3)C(=O)O[C@@]21C]

0.1 g (0.11 mmol) of the product of example 2 step D is dissolved under nitrogen atmosphere in 5 ml DMF and 1 drop of water and 0.053 ml (0.21 mmol) of tributylphosphine are added and the mixture is stirred at room temperature until no starting material remained (2 h). Then 50.6 mg (0.12 mmol) of (2-chloroethyl)-(3-cyclopentyloxy-4-methoxy-phenyl)-(3,5-dichloropyridin-4-yl-methyl)-amine (compound 4-B) and 0.016 ml DBU are added to the solution. The reaction is stirred for 20 hours at room temperature and concentrated in vacuo and the residue is taken up in 5 ml DCM. The organic layer is washed twice with 2 ml aqueous NaHCO$_3$ (5%) and with 2 ml brine, dried over Na$_2$SO$_4$, filtered and concentrated in vacuo to give the crude product (0.184 g) as a yellow oil.

The crude product is purified by flash chromatography on silica gel (DCM/MeOH/NH3 99.8:0.2:0.01→99:1:0.01) to give 0.072 mg of the desired product as a white solid. MS (ESI): 1280.6 ([MH]$^+$), 641.1 ([MH$_2$]$^{++}$).

D] Preparation of Compound I-4

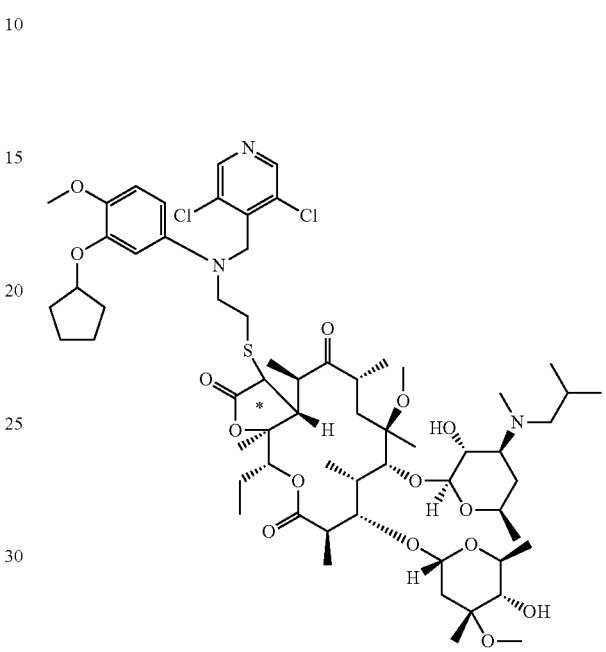

72 mg of the product of example 4 step C (4-C) is dissolved in 2 ml methanol. The mixture is stirred for ten days at room temperature. Methanol is evaporated and the crude product is purified by flash chromatography on silica gel (DCM/MeOH/NH$_3$ 99.8:0.2:0.01→99:1:0.01) followed by a purification by preparative HPLC (System Bp) to give 26 mg of the desired product as a white solid.

MS: accurate mass (ESI): 1238.6024 Da.

Ret. Time (system Ba): 41.7 min.

1H-NMR (CDCl$_3$) (diagnostic signals only): 8.45 (s, 2H); 6.77 (d, 1H); 6.51 (d, 1H); 6.46 (dd, 1H); 5.42 (dd, 1H); 4.92 (d, 1H); 4.73 (m, 1H); 4.65 (s, 2H); 4.31 (s, 1H); 4.01 (m, 1H); 3.82 (m, 1H); 3.80 (s, 2H); 3.10 (s, 3H); 0.87 (t, 3H).

Example 5

Preparation of I-5, compound of formula I where R1 is [2-[4-amino-7-(3,5-dichloro-pyridin-4-yl-amino-carbonyl)-imidazo[4,5-c]pyridin-1-yl]-ethyl]thio, R2 is O-cladinosyl, R5 is dimethylamino, R8 is methoxy, R3, R4, R6, R7 and R9 are hydrogen.

A] Preparation of Compound 5-A

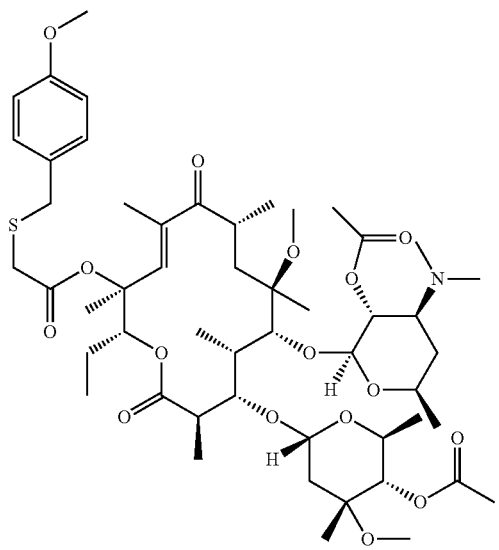 [SMILES: CC[C@H]1OC(=O)[C@H](C)[C@@H](O[C@H]2C[C@@](C)(OC)[C@@H](OC(C)=O)[C@H](C)O2)[C@H](C)[C@@H](O[C@@H]2O[C@H](C)C[C@H](N(C)C)[C@H]2OC(C)=O)[C@](C)(OC)C[C@@H](C)C(=O)/C(C)=C/[C@]1(C)OC(=O)CSCc1ccc(OC)cc1]

10.5 g of compound of formula V where R2 is 4"-ORp1-cladinosyl, R6 is ORp₁, R7 is dimethylamino, R3, R4, R5, R8 and R9 are hydrogen and Rp₁ is acetyl (WO2006084410, example 1) are dissolved under argon in 180 ml acetone and 2.42 g DBU, 20 mg sodium iodide and 2.20 g (4-methoxyphenyl)methanethiol are added in one portion. The reaction mixture is stirred under argon at room temperature for 2.5 hours. 250 ml of DCM are added to the reaction mixture. The organic layer is washed three times with 5% NaHCO₃, dried over Na₂SO₄ and evaporated in vacuo to give 11.7 g (98.4%) of a light brown foam. MS (ESI): 1008.4.

B] Preparation of Compound 5-B

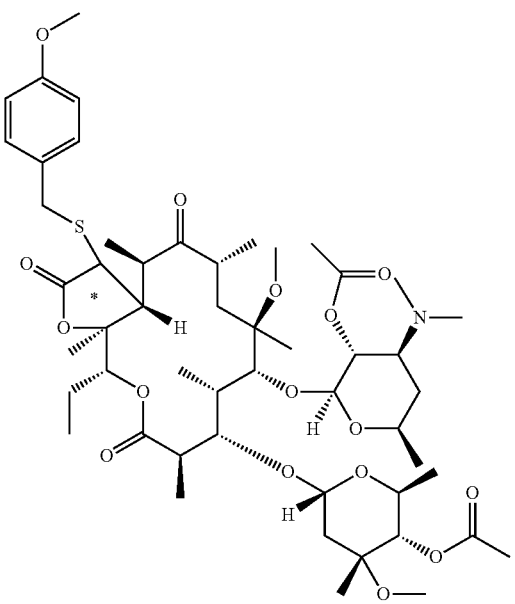 [SMILES: CC[C@H]1OC(=O)[C@H](C)[C@@H](O[C@H]2C[C@@](C)(OC)[C@@H](OC(C)=O)[C@H](C)O2)[C@H](C)[C@@H](O[C@@H]2O[C@H](C)C[C@H](N(C)C)[C@H]2OC(C)=O)[C@](C)(OC)C[C@@H](C)C(=O)[C@H](C)[C@H]2C(SCc3ccc(OC)cc3)C(=O)O[C@@]21C]

6.00 g of compound of compound 5-A are dissolved under nitrogen in 60 ml DMF and cooled with an ice bath. 0.39 g sodium hydride oil dispersion (60%) are added and the mixture is stirred during 3 hours at 0-5° C. Now aqueous KH₂PO₄ 0.5N are added and the mixture is extracted with 100 ml diethylether. The organic layer is washed three times with 60 ml aqueous NaHCO₃ 3% and with 80 ml brine, dried over Na₂SO₄ and evaporated in vacuo to afford 4.65 g crude product. MS (ESI): 1008.4 [MH]⁺.

C] Preparation of Compound 5-C

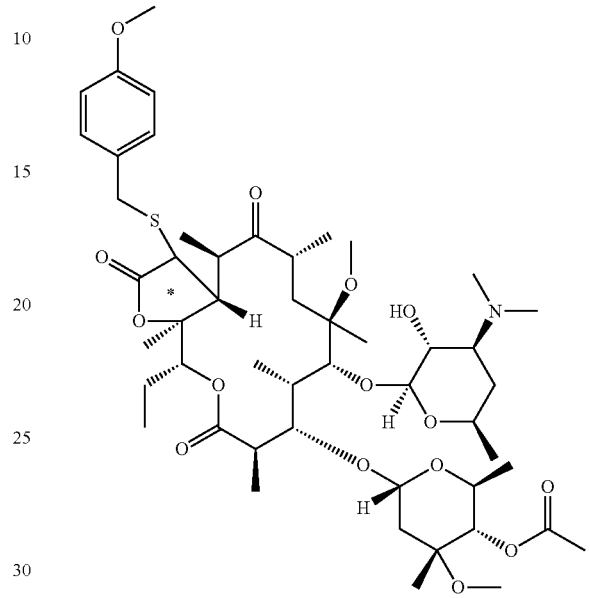

7.5 g of a product of example 5, step B are dissolved in 140 ml of methanol and the solution is stirred at 40° C. for 30 hours. The solvent is evaporated and the crude product is purified by flash chromatography on silica gel (DCM/MeOH 80:1 then 30:1) to give 4.2 g (65%) of the desired product as a yellow foam.

D] Preparation of Compound 5-D

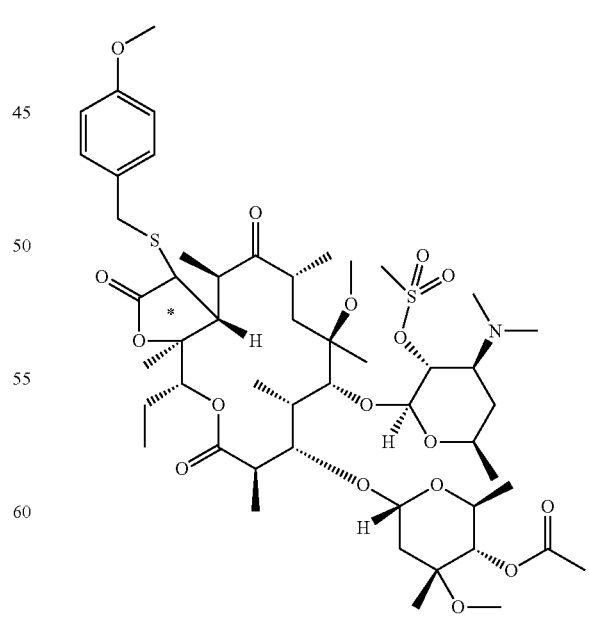

11.5 g (11.9 mmol) of a product 5-C are dissolved in 100 ml dry DCM under nitrogen atmosphere and 3.3 ml (41.7 mmol)

pyridine are added. The solution is cooled to 10° C. and 5.18 g (29.8 mmol) dissolved in 20 ml dry DCM are added dropwise over a period of 5 minutes. The solution is stirred at 27° C. for the 20 hours. The resulting suspension is filtered and the solids are washed with 200 ml DCM. The combined organic layers are washed three times with 200 ml water and with 200 ml brine, dried over $Na_2SO_4$ and evaporated in vacuo to give the product as a foam. The crude product is purified by flash chromatography on silica gel (DCM:methanol 200:1) to afford 9.05 g (73%) of the desired product as a light yellow solid.

$^1$H NMR (CDCl$_3$): (diagnostic signals only) 7.32 (d, 2H); 6.83 (d, 2H); 5.47 (dd, 1H); 4.92 (d, 1H); 4.66 (d, 1H); 4.63 (d, 1H); 4.31 (s, 1H); 4.22-4.30 (m, 2H); 4.10 (d, 1H); 4.04 (d, 1H); 3.81 (d, 1H); 3.78 (s, 3H); 3.60-3.72 (m, 2H); 3.30 (s, 3H); 3.17 (s, 3H); 3.06 (s, 3H); 2.93-3.01 (m, 1H); 2.70-2.84 (m, 2H); 2.55 (s, 1H); 2.50 (m, 1H); 2.38 (d, 1H); 2.28 (s, 6H); 2.10 (s, 3H); 1.82-1.95 (m, 2H); 1.72-1.81 (m, 2H); 1.42 (s, 3H); 1.31 (s, 3H); 1.03 (d, 3H); 0.85 (t, 3H).

E] Preparation of Compound 5-E

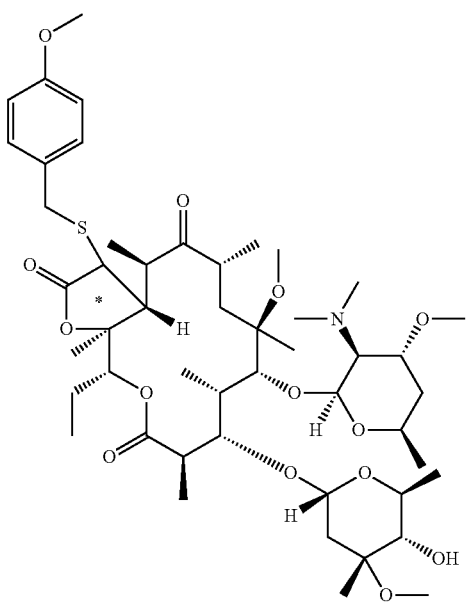 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@@H](OC)[C@@H]2N(C)C)[C@](C)(OC)C[C@@H](C)C(=O)[C@H](C)[C@H]2C(SCc3ccc(OC)cc3)C(=O)O[C@@]21C]

380 mg of the compound 5-D are suspended in 20 ml of methanol and the reaction mixture is heated to reflux. The clear solution is stirred at this temperature for 5 hours. Then 280 mg of DBU are added and the reaction mixture is stirred for 12 hours at 60° C. and subsequently concentrated under reduced pressure. The residue is dissolved in 40 ml ethyl acetate and the organic layer is washed three times with 40 ml water and 40 ml of brine, dried over $Na_2SO_4$ and evaporated in vacuo to give the crude product as a light yellow foam. The crude product is purified by column chromatography on silica gel (DCM:methanol 50:1) to give 310 mg (90%) of the desired product as white solid. $^1$H NMR (CDCl$_3$): 7.33 (d, 2H), 6.84 (d, 2H), 5.48 (d, 1H), 4.89 (s, 1H), 4.85 (d, 1H), 4.30 (s, 1H), 4.11 (d, 1H); 4.08 (d, 1H), 4.00 (m, 1H), 3.8 (d, 2H), 3.79 (s, 3H), 3.53 (m, 2H), 3.33 (s, 3H), 3.29 (s, 3H), 3.09 (s, 3H), 2.97 (m, 2H), 2.74 (m, 1H), 2.54 (m, 3H), 2.50 (s, 6H), 2.40 (s, 1H), 2.32 (d, 1H), 1.93-1.75 (m, 3H), 1.69-1.62 (m, 2H), 1.57-1.49 (m, 3H), 1.42 (s, 6H), 1.28 (d, 3H), 1.22 (s, 3H), 1.19 (s, 3H), 1.17 (d, 3H), 1.08 (d, 3H), 1.04 (d, 3H), 0.96 (d, 3H), 0.86 (t, 3H).

F] Preparation of Compound 5-F

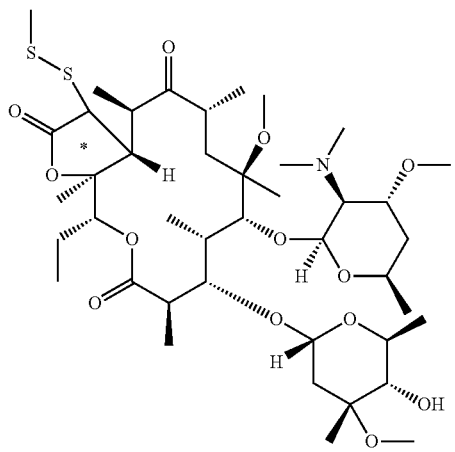 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@@H](OC)[C@@H]2N(C)C)[C@](C)(OC)C[C@@H](C)C(=O)[C@H](C)[C@H]2C(SSC)C(=O)O[C@@]21C]

2 g (2.13 mmol) of the product of example 5, step E are dissolved in 30 ml DCM and 0.95 g (4.82 mmol) dimethyl (methylthio)sulfonium tetrafluoroborate and 12 g molecular sieves (4A) are added to the mixture and the reaction is stirred for 4 hours at 10° C. The molecular sieves is filtered off and washed with 60 ml DCM. The combined organic layers are washed twice with 80 ml aqueous NaHCO$_3$ (5%), with 80 ml water and with 80 ml brine, dried over $Na_2SO_4$ and concentrated in vacuo to give 1.85 g of the desired product as a light yellow solid. The crude product is used without purification for the next step. MS (ESI): 864.5.

G] Preparation of Compound 5-G

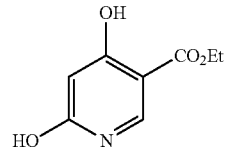 [SMILES: CCOC(=O)c1cnc(O)cc1O]

A mixture of 5.0 g (24.73 mmol) diethyl 1,3-acetonedicarboxylate, 5.05 g (49.45 mmol) acetic anhydride and 3.7 g (24.73 mmol) ethyl orthoformate is heated to 120° C. for 2 hours. Volatile components are removed under reduced pressure and the remaining mixture is treated with 10 ml of aqueous ammonia (25%). The mixture is stirred for 30 minutes at room temperature. Subsequently the pH of the mixture is adjust to pH 2 with aqueous HCl (2N). The solid is filtered off, washed with cold water and dried. 8 ml of toluene are added to the crude product, the mixture is stirred at 0° C. for 30 minutes and then filtered and dried to give 2.26 g (50%) of a red solid.

$^1$H-NMR (DMSO-d$_6$): 11.77 (s, br, 1H); 10.74 (s, br, 1H); 8.01 (s, 1H); 5.60 (s, 1H); 4.26 (q, 2H); 1.28 (t, 3H).

H] Preparation of Compound 5-H

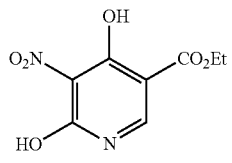

To a solution of 2.34 g (12.78 mmol) of compound 5-G in 9 ml of acetic acid is added dropwise at 60° C. 1.24 g nitric acid (65%; 12.78 mmol). The mixture is stirred at 90° C. for 20 hours. The reaction mixture is cooled to 0° C., filtered and the filter cake is washed with cold water. The solid is dried to give 2.2 g (75%) of the desired product as light yellow crystals.

MS (ESI): 229.0 ([MH]$^+$).

I] Preparation of Compound 5-I

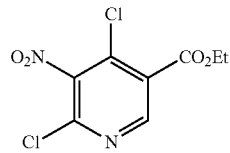 [SMILES: CCOC(=O)c1cnc(Cl)c([N+](=O)[O-])c1Cl]

2.0 g (8.77 mmol) of compound 5-H in 8.0 ml (86 mmol) phosphorus oxychloride are stirred at 80° C. for 74 hours. About half of the phosphorus oxychloride is then removed in vacuo and the remaining mixture is poured onto ice. The mixture is extracted with 3×30 ml of ethyl acetate. The combined organic phases are washed with 30 ml of aqueous sodium carbonate (10%), 2×30 ml water and 30 ml of brine, dried over $Na_2SO_4$ and evaporated in vacuo to give the crude product as a brown oil which is purified by column chromatography on silica gel (ethyl acetate/hexane 1:20) to give 1.67 g (72%) of the desired product as light yellow solid.

$^1$H-NMR (DMSO-$d_6$): 9.08 (s, 1H); 4.40 (q, 2H); 1.35 (t, 3H).

K] Preparation of Compound 5-K

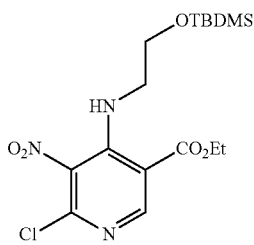 [SMILES: CCOC(=O)c1cnc(Cl)c([N+](=O)[O-])c1NCCO[Si](C)(C)C(C)(C)C]

A solution of 362 mg (1.37 mmol) of compound 5-1 and 138 mg (1.37 mmol) triethylamine in 4 ml of ethanol is heated to reflux. 240 mg (1.37 mmol) of 2-(tert-butyl-dimethyl-silanyloxy)-ethylamine is added dropwise to this solution and the mixture is stirred at reflux for an additional hour. The solvent is removed under reduced pressure and the resulting residue is purified by column chromatography on silica gel (hexane/ethyl acetate 80:1) to afford 430 mg (79%) of the desired product as yellow oil.

$^1$H-NMR (DMSO-$d_6$): 9.05 (m, 1H); 8.66 (s, 1H); 4.33 (q, 2H); 3.75 (t, 2H); 3.11 (t, 2H); 1.32 (t, 3H); 0.84 (s, 9H); 0.04 (s, 6H).

L] Preparation of Compound 5-L

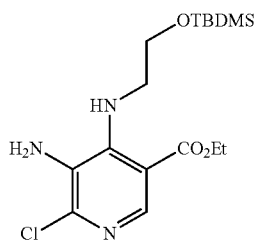

1.7 g (4.21 mmol) of compound 5-K are dissolved in 10 ml of ethanol and 0.5 g of Raney-nickel are added. The reaction mixture is stirred for 12 hours under an atmosphere of hydrogen gas (1 atm) at room temperature. The catalyst is removed by filtration through a pad of silica gel and the filtrate is concentrated under reduced pressure. The crude product is purified by column chromatography on silica gel (hexane/ethyl acetate 80:1→40:1→20:1) to afford 570 mg (36%) of the desired product as brown oil.

MS (ESI): 374.1 ([MH]$^+$).

$^1$H-NMR (DMSO-$d_6$): 8.01 (s, 1H); 7.25 (t, 1H); 4.94 (s, 2H); 4.27 (q, 2H), 3.65 (m, 2H); 3.42 (m, 2H); 1.30 (t, 3H); 0.81 (s, 9H); −0.02 (s, 6H).

M] Preparation of Compound 5-M

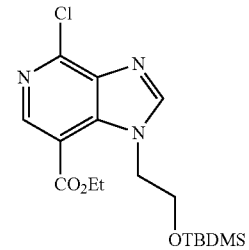

250 mg (0.67 mmol) of compound 5-L are dissolved in 3 ml triethylorthoformate and the mixture is heated to reflux during 44 hours. The mixture is concentrated under reduced pressure and the residue is purified by column chromatography on silica gel eluting with hexane/ethyl acetate (20/1→10/1→5/1) to afford 124 mg g (48%) of the desired compound as light brown oil.

$^1$H-NMR (DMSO-$d_6$): 8.59 (s, 1H); 8.52 (s, 1H); 4.72 (m, 2H); 4.40 (q, 2H); 3.81 (m, 2H); 1.36 (t, 3H); 0.64 (s, 9H); −0.28 (s, 6H).

N] Preparation of Compound 5-N

Approximately 20 ml of liquid ammonia are dissolve in 20 ml of ethanol in a 100 ml autoclave and 476 mg of compound 5-M are added. The mixture is stirred at 100° C. for 16 hours.

The reaction is cooled down and the solvent is evaporated under reduced pressure. The residue is purified by column chromatography on silica gel (DCM/MeOH 100:1, 80:1 then 50:1) to afford 160 mg (35%) of a white solid.

$^1$H-NMR (DMSO-d$_6$): 8.34 (s, 1H); 8.03 (s, 1H); 7.03 (s, 2H); 4.67 (m, 2H); 4.27 (q, 2H); 3.77 (m, 2H); 1.30 (t, 3H); 0.69 (s, 9H); –0.27 (s, 6H).

O] Preparation of Compound 5-O

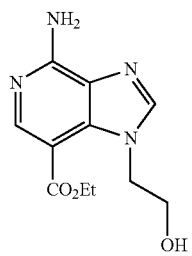 [SMILES: CCOC(=O)c1cnc(N)c2ncn(CCO)c12]

2.0 g (5.49 mmol) of compound 5-N are dissolved in 30 ml dry THF and 1.46 g (~5.6 mmol) tetrabutylammonium fluoride is added. The mixture is stirred at room temperature for 0.5 hour. The solvent is removed under reduced pressure and the residue is purified by preparative HPLC to give 300 mg (22%) of the desired product as a white solid.

$^1$H-NMR (DMSO-d$_6$): 8.31 (s, 1H); 8.01 (s, 1H); 7.04 (s, 2H); 4.80 (m, 1H); 4.57 (m, 2H); 4.26 (q, 2H); 3.57 (m, 2H); 1.29 (t, 3H).

P] Preparation of Compound 5-P

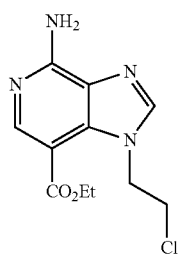 [SMILES: CCOC(=O)c1cnc(N)c2ncn(CCCl)c12]

A suspension of 100 mg of compound 5-O in 4 ml thionyl chloride is stirred at 70° C. for 5 hours. 0.05 ml of triethylamine are added and stirring is continued for 4 hours at 70° C. and another 13.5 hours at room temperature. After completion of the reaction 5 ml of diethyl ether is added to the cooled reaction mixture leading to the formation of a precipitate. The solid is isolated by filtration to give 65 mg (60%) of the desired product as a light yellow powder.

MS (ESI): 269.1 ([MH]$^+$).

$^1$H-NMR (DMSO-d$_6$): 9.00 (s, br, 2H); 8.53 (s, 1H); 8.31 (s, 1H); 4.96 (t, 2H); 4.33 (q, 2H); 4.00 (t, 2H); 1.32 (t, 3H).

Q] Preparation of Compound 5-Q

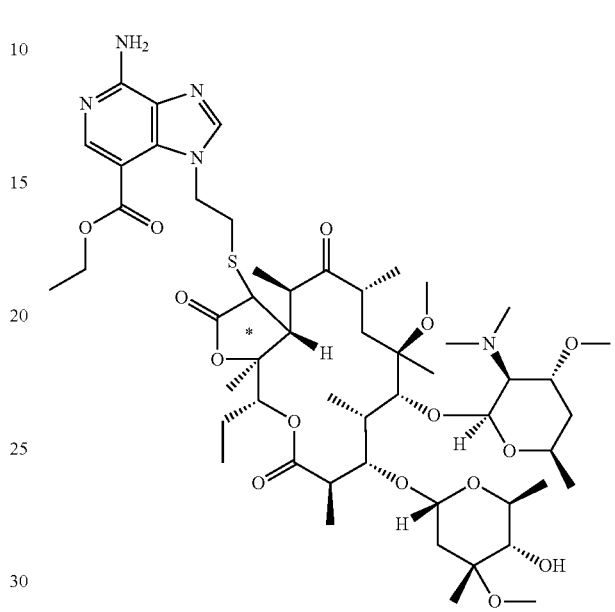

1.2 g (1.28 mmol) of compound 5-F is dissolved under nitrogen atmosphere in 50 ml DMF and 0.3 ml water and 775 mg (3.83 mmol) of tributylphosphine are added and the mixture is stirred at room temperature until no starting material remained (4 h). Then 342 mg (1.28 mmol) of compound 5-P and 230 mg DBU are added to the solution. The reaction is stirred for 20 hours at room temperature and then 120 ml water are added. The aqueous layer is extracted three times with 80 ml ethyl acetate. The combined organic phases are washed three times with 120 ml water and with 100 ml brine, dried over Na$_2$SO$_4$, filtered and concentrated in vacuo to give the crude product. The crude product is purified by flash chromatography on silica gel (DCM/MeOH 80:1 then 20:1) to give 380 mg of the desired product as a light yellow foam.

$^1$H NMR (CDCl$_3$) (diagnostic signals only): 8.57 (s, 1H), 8.18 (s, 1H), 5.63 (s, 2H), 5.31 (d, 1H), 5.27 (m, 1H), 4.95 (s, 1H), 4.82 (d, 1H), 4.74 (m, 1H), 4.47 (s, 1H), 4.33 (q, 2H), 3.99 (m, 1H), 3.85 (m, 1H), 3.75 (m, 2H), 3.61-3.49 (m, 2H), 3.34 (s, 3H), 3.28 (s, 3H), 3.08 (s, 3H), 3.12-2.92 (m, 3H), 2.75 (m, 2H), 2.62 (s, 6H), 2.54 (s, 1H), 2.43 (d, 2H), 2.30 (d, 2H), 1.84 (m, 3H), 1.70 (m, 2H), 1.60-1.48 (m, 3H), 1.46 (s, 3H), 1.44 (s, 3H), 1.4~21.38 (m, 3H), 1.28 (d, 3H), 1.22-1.02 (m, 9H), 0.96 (d, 3H), 0.86 (t, 3H).

R] Preparation of Compound 5-R

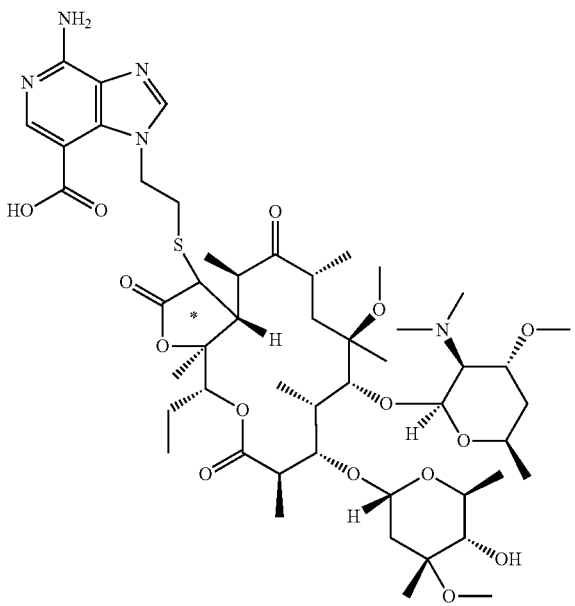 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@@H](OC)[C@@H]2N(C)C)[C@](C)(OC)C[C@@H](C)C(=O)[C@H](C)[C@H]2C(SCCn3cnc4c(N)ncc(C(=O)O)c43)C(=O)O[C@@]21C]

To a solution of 380 mg of compound 5-Q in 6 ml of THF and 1 ml of MeOH at 10° C. are added 2.7 ml of a 0.5 M aqueous solution of LiOH. The mixture is stirred over night at 28° C. The reaction mixture is neutralized with 2N aqueous HCl and dried in vacuo. The residue is purified by preparative HPLC (Column: Purospher STAR RP18e, 5 μm, 125×25 mm flow: 25 mL/min; detection: 254 nm; mobile phase A: 25 mM aqueous ammonium formate; mobile phase B: acetonitrile; gradient: linear from 20% to 40% B in 10 min, then linear from 40% to 100% B in 5 min) to give 180 mg (49%) of the desired product as light yellow solid.

MS (ESI): 511.8 ([MH]$^+$).

S] Preparation of Compound I-5

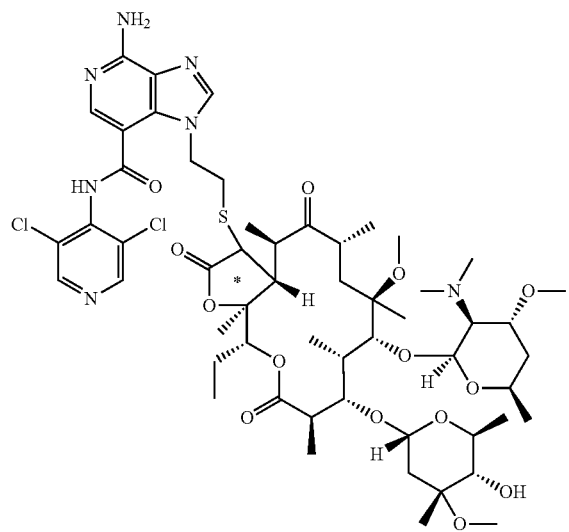 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@@H](OC)[C@@H]2N(C)C)[C@](C)(OC)C[C@@H](C)C(=O)[C@H](C)[C@H]2C(SCCn3cnc4c(N)ncc(C(=O)Nc5c(Cl)cncc5Cl)c43)C(=O)O[C@@]21C]

63 mg (1.57 mmol) of NaH (60% in oil) are added to a solution of 306 mg (1.88 mmol) 4-amino-3,5-dichloropyridine in 3 ml DMF. The suspension is stirred at 25° C. for 5 hours. In parallel, a solution of 160 mg (0.16 mmol) of compound 5-R, 96 mg (0.5 mmol) EDC.HCl and 47 mg (0.34 mmol) HOBt in 4 ml DMF is stirred for 1 hour at 25° C. This solution is then added at 0 to 10° C. to the solution of the sodium salt of 4-amino-3,5-dichloropyridine prepared above. The mixture is stirred at this temperature for 5 minutes and the reaction is quenched with aqueous HC12N. The reaction mixture is diluted with water and the aqueous layer is extracted several times with ethyl acetate. The combined organic layers are washed with water and brine, dried over Na$_2$SO$_4$, filtered and concentrated in vacuo to give the crude product. The crude product is purified by preparative HPLC (Column: Purospher STAR RP18e, 5 μm, 125×25 mm flow: 25 mL/min; detection: 254 nm; mobile phase A: 25 mM aqueous ammonium formate; mobile phase B: acetonitrile; gradient: linear from 20% to 68% B in 8.5 min, then linear from 68% to 100% B in 0.5 min). The fraction containing the product are evaporated and the product is further purified column chromatography on silica gel (DCM/MeOH 25:1 then 20:1) to give the desired product as a white solid.

MS: accurate mass (ESI): 1166.5011 Da.

Ret. Time (system Ba): 28.0 min.

$^1$H NMR (CDCl$_3$) (diagnostic signals only): 8.57 (s, 2H), 8.42 (s, 1H), 8.25 (s, 1H), 7.87 (s, 1H), 5.67 (s, 2H), 5.27 (dd, 1H), 5.06 (m, 1H), 4.91 (s, 1H), 4.81 (d, 1H), 4.67 (m, 1H), 4.33 (s, 1H), 3.99 (m, 1H), 3.84 (m, 1H), 3.73 (d, 1H), 3.59 (m, 1H), 3.55 (d, 1H), 3.52-3.42 (m, 1H), 3.33 (s, 3H), 3.28 (s, 3H), 3.00 (s, 3H), 3.1-2.92 (m, 3H), 2.75 (m, 1H), 2.62 (s, 2H), 2.54 (s, 6H), 2.49 (s, 1H), 2.31 (d, 1H), 1.60-1.48 (m, 3H), 1.46 (s, 3H), 1.41 (s, 3H), 0.95 (d, 3H), 0.81 (t, 3H).

Example 6

Preparation of I-6, compound of formula I where R1 is [2-[(3-cyclopentyloxy-4-methoxy-phenyl)-(pyridin-4-ylmethyl)-amino]-ethyl]thio, R2 is O-cladinosyl, R5 is dimethylamino, R8 is methoxy, R3, R4, R6, R7 and R9 are hydrogen.

A] Preparation of Compound 6-A

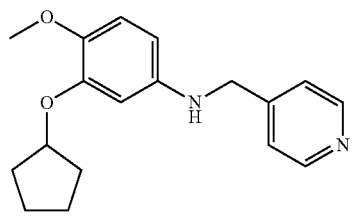 [SMILES: COc1ccc(NCc2ccncc2)cc1OC1CCCC1]

0.5 g (1.6 mmol) of compound 3-A is dissolved under nitrogen in 20 ml dry THF and 0.24 g (6.4 mmol) lithium aluminium hydride are added at room temperature. The reaction mixture is stirred for two hours at room temperature and then cooled to 0° C. and 2 ml of water are added. The mixture is extracted with 3×20 ml of ethyl acetate. The combined organic layers are washed with water and brine, dried over Na$_2$SO$_4$ and evaporated in vacuo to give the crude product as an oil. The crude product is purified by flash chromatography on silica gel (ethyl acetate/n-hexane 1:1) to afford 0.4 g (84%) of the desired product as an oil. MS (ESI): 299.2 ([MH]$^+$).

B] Preparation of Compound 6-B

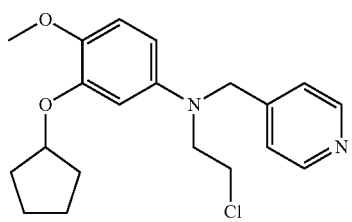 [SMILES: COc1ccc(N(CCCl)Cc2ccncc2)cc1OC1CCCC1]

3.85 g (12.9 mmol) of compound 6-A are dissolved in 50 ml methanol at 25° C. and 5.1 ml of a solution of chloroacetaldehyde (40% in water; 77.4 mmol, 6 eq), 4.86 g (77.4 mmol, 6. eq) of sodium cyano borohydride and 0.74 ml (12.9 mmol) of acetic acid are added. The mixture is stirred at 25° C. for 16 hours. Then the solvent is removed under reduced pressure and the residue is taken up in 100 ml dichloromethane. The mixture is washed with 3×50 ml brine, dried over Na$_2$SO$_4$ and evaporated in vacuo. The crude product is purified by flash chromatography on silica gel (ethyl acetate/n-hexane 1:4) to afford 1.66 g (35%) of the desired product as an oil.

MS (ESI): 361.2, 363.1 ([MH]$^+$).

$^1$H-NMR (CDCl$_3$): 8.52 (d, 2H); 7.17 (d, 2H); 6.75 (d, 1H); 6.18-6.24 (m, 2H); 4.6 (m, 1H); 4.52 (s, 2H); 3.75 (s, 3H); 3.64-3.73 (m, 4H); 1.5-1.9 (m, br, 8H).

C] Preparation of Compound I-6

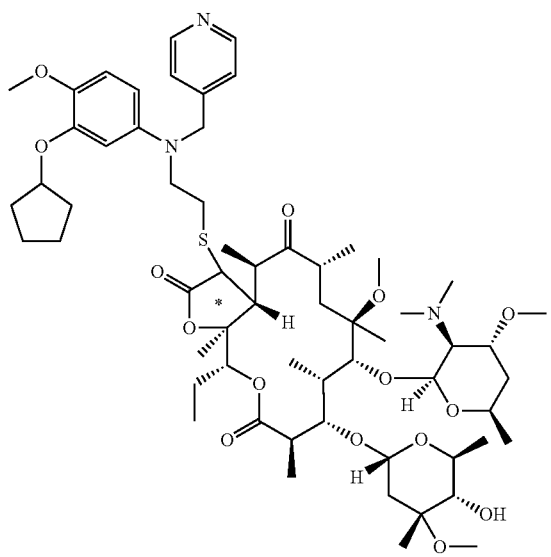

0.11 g (0.13 mmol) of compound 5-F is dissolved under nitrogen atmosphere in 10 ml DMF and 1 drop of water and 0.063 ml (0.25 mmol) of tributylphosphine are added and the mixture is stirred at room temperature until no starting material remained (2 h). Then 50.5 mg (0.14 mmol) of compound 6-B and 0.048 ml (0.13 mmol) DBU are added to the solution. The reaction is stirred overnight at room temperature. The solvent is evaporated in vacuo. The residue is dissolved in 20 ml DCM. The organic phase is washed with aqueous NaHCO$_3$ (5%) and with brine, dried over Na$_2$SO$_4$ and concentrated in vacuo to give the crude product. The crude product is purified by flash chromatography on silica gel (DCM/MeOH 98:2) to give 26 mg of the desired product as a light yellow amorphous solid.

$^1$H NMR (CDCl$_3$) (diagnostic signals only): 8.52 (d, 2H); 7.24 (d, 2H); 6.76 (d, 1H); 6.26 (d, 1H); 6.22 (dd, 1H); 5.48 (dd, 1H); 4.98 (s, 1H); 4.88 (d, 1H); 4.64 (m, 1H); 4.59 (d, 1H); 4.37 (s, 1H); 3.77 (s, 3H); 3.37 (s, 3H); 3.32 (s, 3H); 3.11 (s, 3H); 1.46 (s, 3H); 1.44 (s, 3H); 0.88 (t, 3H).

Example 7

Preparation of I-7, compound of formula I where R1 is [2-[(3-cyclopentyloxy-4-methoxy-phenyl)-(3,5-dichloropyridin-4-yl-methyl)-amino]ethyl]thio, R2 is O-cladinosyl, R5 is dimethylamino, R8 is methoxy, R3, R4, R6, R7 and R9 are hydrogen.

A] Preparation of Compound 7-A

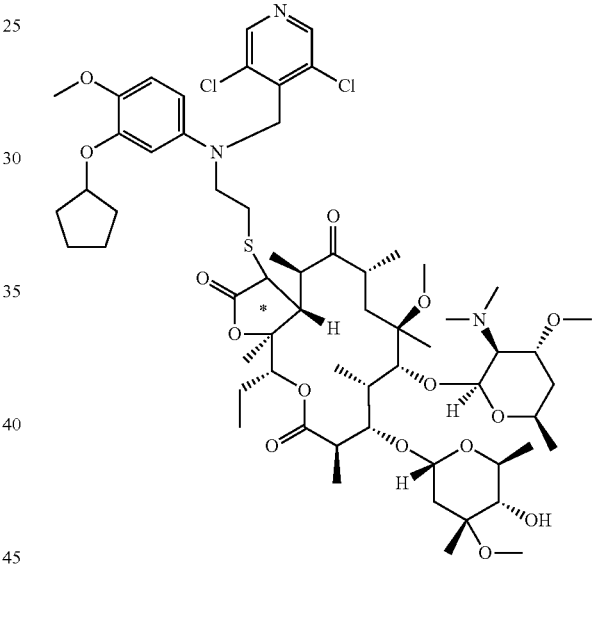

Compound 7-A is prepared from compound 5-F (example 5, step F) and 4-B (example 4, step B) following the procedure described in example 6 step C.

MS: accurate mass (ESI): 1210.5777 Da.

Ret. Time (system Ba): 42.0 min.

Example 8

Preparation of I-7, compound of formula I where R1 is [2-[(3-cyclopentyloxy-4-methoxy-phenyl)-(3,5-dichloropyridin-4-yl-methyl)-amino]ethyl]thio, R2 is OH, R5 is dimethylamino, R8 is methoxy, R3, R4, R6, R7 and R9 are hydrogen.

A] Preparation of Compound 8-A

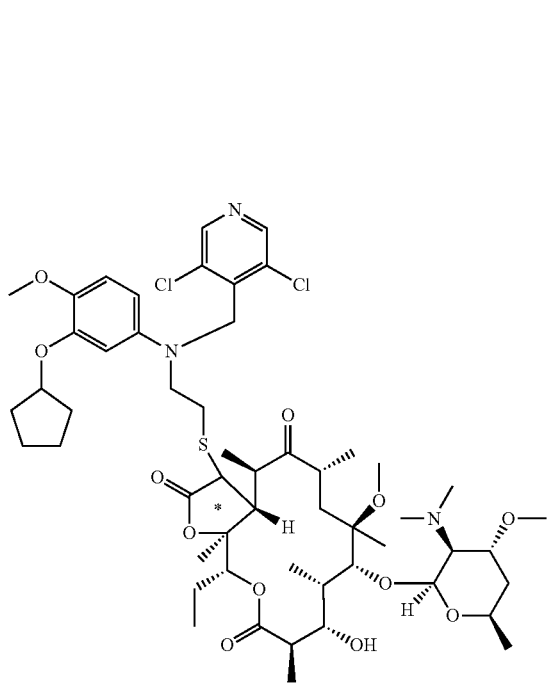

To a stirred solution of 20 mg of compound 7-A in 1 ml ethanol and 2 ml water is added dropwise 0.125 ml aqueous HCl (2N). The clear solution is stirred at room temperature for 20 hours. Additional 0.125 ml aqueous HCl (2N) are added and the reaction is stirred for another 20 hours. The reaction mixture is neutralized with aqueous NaOH (2N) and extracted twice with 10 ml ethyl acetate. The combined organic layers are washed with aqueous NaHCO$_3$ (5%) and with brine, dried over Na$_2$SO$_4$ and concentrated in vacuo to give the crude product (20 mg) as a yellow solid. The crude product is purified by flash chromatography on silica gel (DCM/MeOH/NH$_3$ 99.8:0.2:0.01→96:4:0.01) to give 13 mg of the desired product as a white solid.

MS: accurate mass (ESI): 1052.4845 Da

Ret. Time (system Ba): 39.0 min.

$^1$H-NMR (CDCl$_3$): (diagnostic signals only) 8.46 (s, 2H); 6.77 (d, 1H); 6.52 (d, 1H); 6.46 (dd, 1H); 5.52 (dd, 1H); 5.02 (s, br, 1H); 4.73 (m, 1H); 4.63 (m, 2H); 4.30 (m, 1H); 3.94 (m, 2H); 3.80 (s, 3H); 3.32 (s, 3H); 2.44 (s, 6H).

Example 9

Preparation of I-9, compound of formula I where R1 is [2-[(3-cyclopentyloxy-4-methoxy-phenyl)-(3,5-dichloropyridin-4-yl-methyl)-amino]ethyl]thio, R2 is —OH, R6 is —OCH$_3$, R7 is dimethylamino and R3, R4, R5, R8 and R9 are hydrogen.

A] Preparation of Compound 9-A

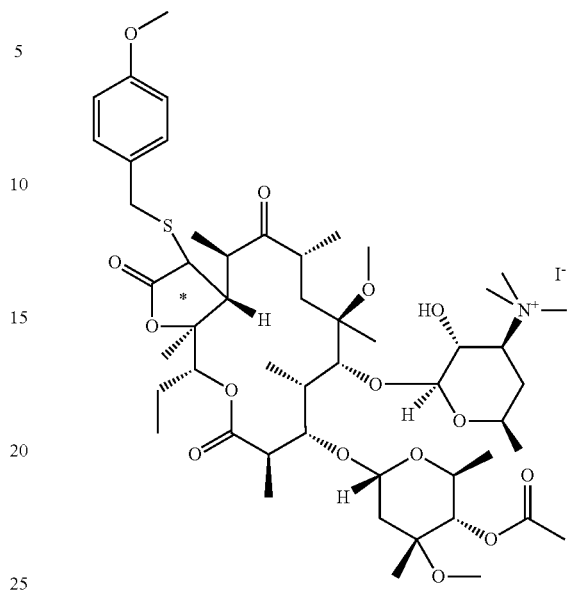

To a stirred solution of 1.93 g (2 mmol) of compound 5-C in 30 ml DCM is added 0.37 ml (6.0 mmol) methyl iodide. The reaction was stirred at 25° C. for 5 h and then the solvent was evaporated to give crude 9-A as a white solid (1.95 g).

MS (ESI): 980.5 ([MH]$^+$).

B] Preparation of compound 9-B

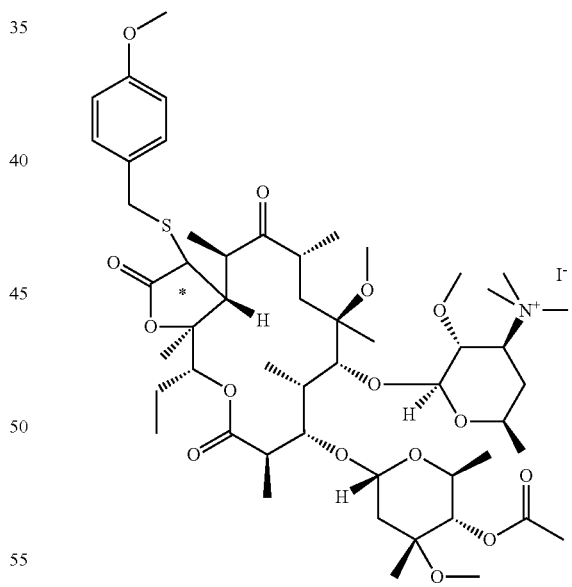

2.22 g (2.0 mmol) of compound 9-A are dissolved in 30 ml of dry THF. 153 mg of NaH (4 mmol) are added to the solution at 0° C. and the mixture is stirred at this temperature for 10 minutes. 2.5 ml (40.0 mmol) of methyl iodide are added and the reaction mixture is stirred for 2 hours at 0-10° C. The mixture is adjusted to pH=7 with diluted aqueous HCl and the solvent is subsequently removed in vacuo to give crude 9-B as light yellow solid. The product is used in the next step without further purification.

MS (ESI): 994.5 ([M]$^+$).

C] Preparation of Compound 9-C

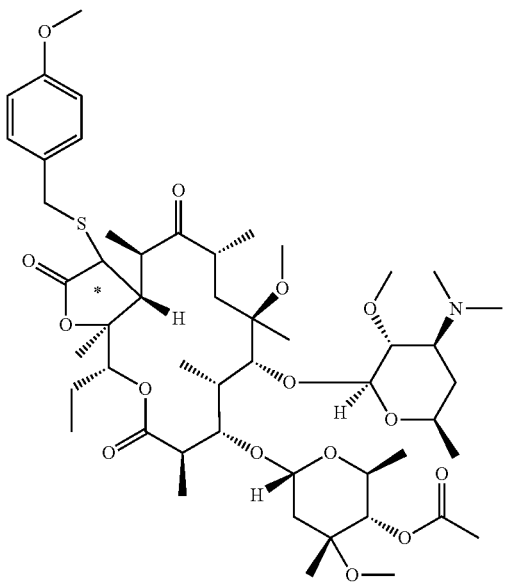 [SMILES: CC[C@H]1OC(=O)[C@H](C)[C@@H](O[C@H]2C[C@@](C)(OC)[C@@H](OC(C)=O)[C@H](C)O2)[C@H](C)[C@@H](O[C@@H]2O[C@H](C)C[C@H](N(C)C)[C@H]2OC)[C@](C)(OC)C[C@@H](C)C(=O)[C@H](C)[C@H]2C(SCc3ccc(OC)cc3)C(=O)O[C@@]21C]

18.8 g of crude compound 9-B is dissolved in 200 ml MeOH and 10.2 g of AgCl (10 eq.) are added. The mixture is stirred for 4 hours at room temperature and filtered. The filtrate is evaporated to dryness in vacuo to give a solid. A solution of 17.2 g (14.2 mmol) of this solid in 100 ml of dry acetonitrile is added to a solution of 12.7 g (0.11 mol) 4-pyridine-thiol and 2.7 g (0.11 mmol) of sodium hydride in 500 ml of dry acetonitrile, which was stirred for 1 hour at 20° C. The resulting mixture is heated to reflux at 90° C. under an atmosphere of nitrogen for 18 h. The mixture is filtered and the filtrate is concentrated in vacuo. The resulting residue is taken up in 800 ml of DCM and the organic layer is washed three times with 150 ml of saturated aqueous ammonium chloride solution, dried over $Na_2SO_4$ and concentrated in vacuo to give 18 g of the crude product. The crude product is purified by flash chromatography on silica gel (DCM/MeOH 150:1→10:1)) to give 6.49 g of the desired product as a light brown solid.

MS (ESI): 980.4 ([MH]$^+$).

D] Preparation of Compound 9-D

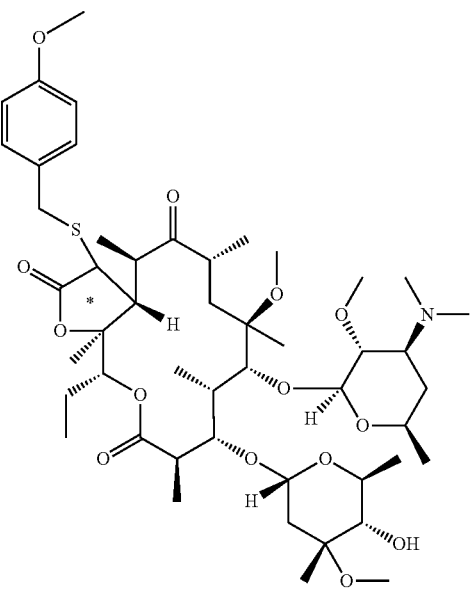 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C)[C@H]2OC)[C@](C)(OC)C[C@@H](C)C(=O)[C@H](C)[C@H]2C(SCc3ccc(OC)cc3)C(=O)O[C@@]21C]

5.78 g of compound 9-C is dissolved in 200 ml of methanol and 3.75 ml of DBU is added. The resulting mixture is stirred for 8 hours at 70° C. The solvent is removed and the crude product is purified by flash chromatography on silica gel (DCM/MeOH 50:1→10:1) to give 3.5 g of a product which is further purified by preparative TLC (DCM/MeOH 10:1) to afford 1.1 g a white solid. 15 ml of DCM is added to 0.48 g of this product and the mixture is filtered. The filtrate is evaporated to give 0.37 g of the desired product as a white solid. MS (ESI): 939.1 ([MH]$^+$).

E] Preparation of Compound 9-E

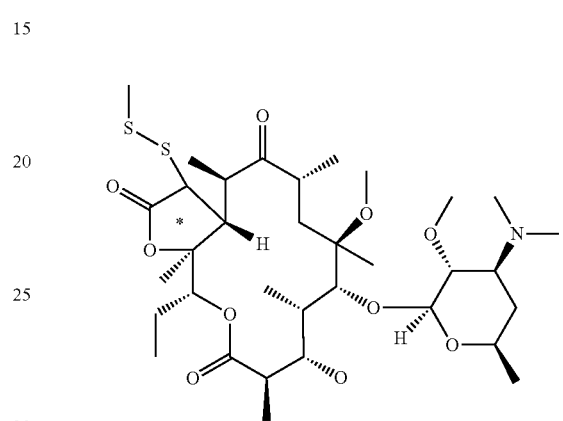

0.37 g (0.39 mmol) of compound 9-D is dissolved in 10 ml of DCM and 4.4 g of molecular sieves (4A) and 0.177 g (0.9 mmol) dimethyl(methylthio)sulfonium tetrafluoroborate are added. The mixture is stirred at room temperature for 3 h. The mixture is filtered and the organic layer si washed twice with aqueous $NaHCO_3$, with water and with brine, dried over $Na_2SO_4$ and concentrated in vacuo to give 0.25 g the desired product as a dark oil. The product is used in the next step without further purification.

F] Preparation of Compound I-9

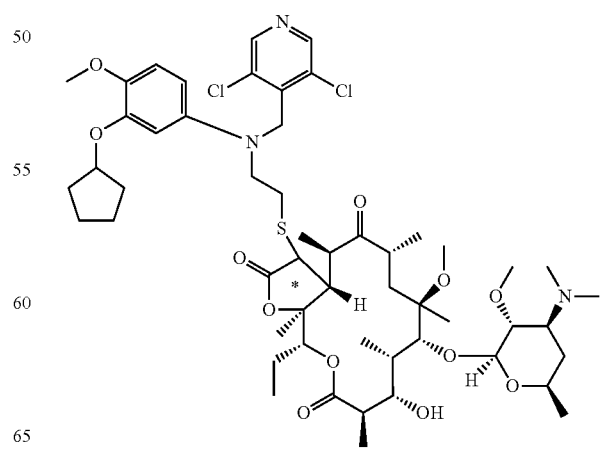

0.15 g (0.21 mmol) of the product of example 9 step E is dissolved under nitrogen atmosphere in 10 ml DMF and 1 drop of water and 0.105 ml (0.42 mmol) of tributylphosphine are added and the mixture is stirred at room temperature until no starting material remained (2 h). Then 100 mg (0.23 mmol) of (2-chloroethyl)-(3-cyclopentyloxy-4-methoxy-phenyl)-(3,5-dichloropyridin-4-yl-methyl)-amine (compound 4-B) and 0.032 ml DBU are added to the solution. The reaction is stirred for 20 hours at room temperature and concentrated in vacuo and the residue is taken up in 5 ml DCM. The organic layer is washed twice with 2 ml aqueous NaHCO$_3$ (5%) and with 2 ml brine, dried over Na$_2$SO$_4$, filtered and concentrated in vacuo to give the crude product (0.31 g) as a brown oil. The crude product is purified by flash chromatography on silica gel (DCM/MeOH/NH3 99.8:0.2:0.01→93:7:0.01) to give 0.079 mg of the product which was further purified by preparative HPLC (system Ap) to give 18 mg of the desired product as a white solid. Ret. Time (system Ba): 38.5 min.

MS (ESI): 1052.6, 1054.6 ([MH]$^+$).

Example 10

Preparation of I-10, compound of formula I where R1 is [2-[(3-cyclopentyloxy-4-methoxy-phenyl)-(3,5-dichloropyridin-4-yl-methyl)-amino]ethyl]thio, R2 is —O-cladinosyl, R6 is —OH, R7 is acetyl-methyl-amino and R3, R4, R5, R8 and R9 are hydrogen.

A] Preparation of Compound 10-A

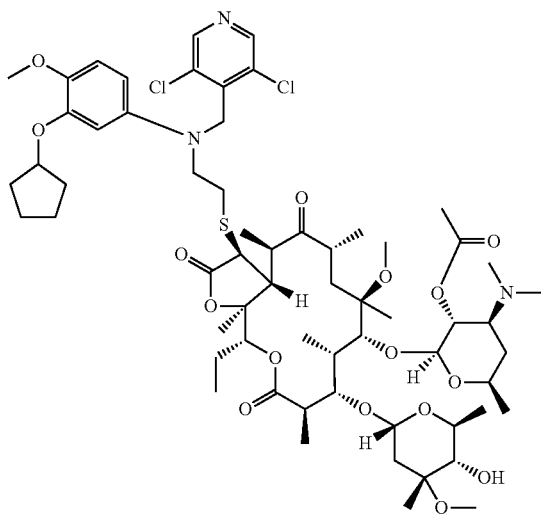

0.30 g (0.34 mmol) of the compound of formula VIII where Rp$_4$ is methyl, R2 is O-cladinosyl, R6 is O-acetyl, R7 is dimethylamino and R3, R4, R5, R8 and R9 are hydrogen (WO2008/017696, example 1, product of step N) is dissolved under nitrogen atmosphere in 10 ml DMF and 1 drop of water and 0.166 ml (0.67 mmol) of tributylphosphine are added and the mixture is stirred at room temperature until no starting material remained (2 h). Then 159 mg (0.37 mmol) of (2-chloroethyl)-(3-cyclopentyloxy-4-methoxy-phenyl)-(3,5-dichloropyridin-4-yl-methyl)-amine (compound 4-B) and 0.05 ml DBU are added to the solution. The reaction is stirred for 20 hours at room temperature and concentrated in vacuo and the residue is taken up in 10 ml DCM. The organic layer is washed twice with aqueous NaHCO$_3$ (5%) and with brine, dried over Na$_2$SO$_4$, filtered and concentrated in vacuo to give the crude product (0.64 g) as a yellow oil. The crude product is purified by flash chromatography on silica gel (DCM/MeOH/NH3 99.8:0.2:0.01→94:6:0.01) to give 0.20 g of the desired product as a white foam.

B] Preparation of Compound 10-B

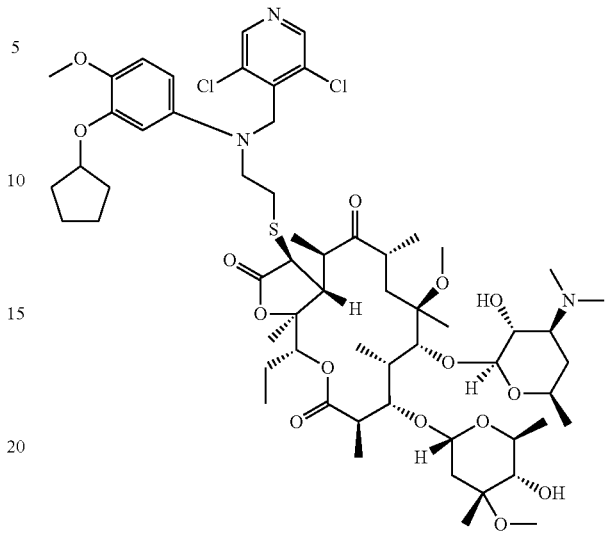

200 mg of compound 10-A is dissolved in 10 ml of methanol and the solution is stirred for 4 days at room temperature. The solvent is evaporated and the residue is purified by flash chromatography on silica gel (DCM/MeOH/NH3 99:1:0.01→92:8:0.01) to give 153 mg of the desired product as an off-white gum.

MS (ESI): 1197.1, 1199.1 ([MH]$^+$).

C] Preparation of Compound 10-C

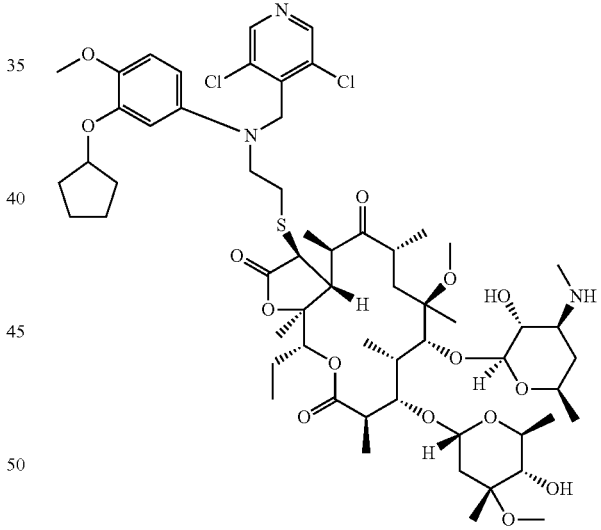

100 mg of compound 10-B is dissolved in 5 ml of methanol and 0.5 ml of water and 34 mg of sodium acetate are added. The mixture is stirred for 10 minutes and 42.4 mg of iodine are added. The dark mixture is heated to 60° C. for 6 hours and after addition of 42.4 mg of iodine the mixture is stirred for an additional 3 hours at 60° C. The reaction mixture is quenched with a 1M aqueous solution of Na$_2$S$_2$O$_3$. The solvent is removed in vacuo and the residue is taken up in DCM. The organic layer is washed with aqueous NaHCO$_3$ (5%), water and with brine, dried over Na$_2$SO$_4$, filtered and concentrated in vacuo to give the crude product (97 mg) as a brown oil. The crude product is purified by flash chromatography on silica gel (DCM/MeOH/NH$_3$ 99:1:0.01→86:14:0.01) to give 37 mg of a yellow solid. The product was used without further purification for the next step.

D] Preparation of Compound I-10

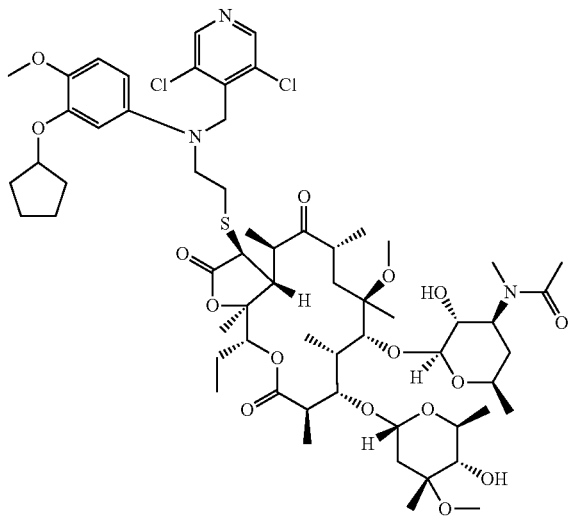 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C(C)=O)[C@H]2O)[C@](C)(OC)C[C@@H](C)C(=O)[C@H](C)[C@H]2[C@H](SCCN(Cc3c(Cl)cncc3Cl)c3ccc(OC)c(OC4CCCC4)c3)C(=O)O[C@@]21C]

37 mg of compound 10-C is dissolved in 2 ml DCM and 4.4 µl triethylamine and 3 µl acetic anhydride is added. The reaction mixture is stirred for 2 h at room temperature. The mixture is washed with aqueous NaHCO$_3$ (5%), water and with brine, dried over Na$_2$SO$_4$, filtered and concentrated in vacuo to give the crude product (51 mg) as a yellow oil. The crude product is purified by flash chromatography on silica gel (DCM/MeOH/NH$_3$ 99.5:0.5:0.01→97:3:0.01) to give 31 mg of the desired product as an off-white solid.

Ret. Time (system Ba): 46.0 min.
MS (ESI): 1224.9 ([MH]$^+$).

Example 11

Preparation of I-11, compound of formula I where R1 is [2-[(3-cyclopentyloxy-4-methoxy-phenyl)-(3,5-dichloropyridin-4-yl-methyl)-amino]ethyl]thio, R2 is —O-cladinosyl, R5 is dimethylamino, R8 is 4-morpholinyl and R3, R4, R6, R7 and R9 are hydrogen.

A] Preparation of Compound II-A

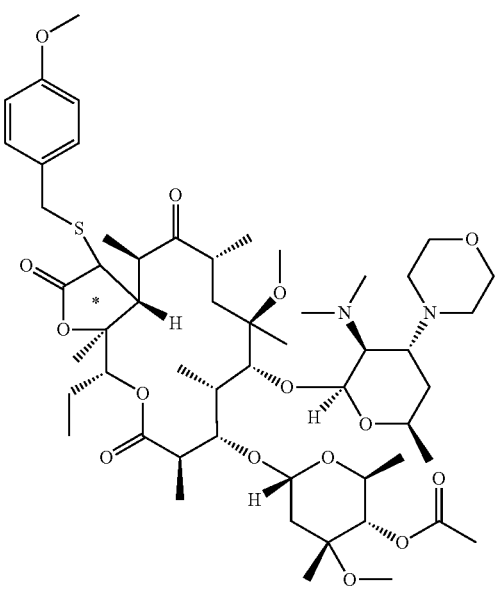 [SMILES: CC[C@H]1OC(=O)[C@H](C)[C@@H](O[C@H]2C[C@@](C)(OC)[C@@H](OC(C)=O)[C@H](C)O2)[C@H](C)[C@@H](O[C@@H]2O[C@H](C)C[C@@H](N3CCOCC3)[C@@H]2N(C)C)[C@](C)(OC)C[C@@H](C)C(=O)[C@H](C)[C@H]2C(SCc3ccc(OC)cc3)C(=O)O[C@@]21C]

3.25 g (3.1 mmol) of the product of example 5 step D are dissolved in 200 ml of THF and 18.5 ml (0.2 mol) morpholine are added. The mixture is heated to reflux for 20 hours. The solvent is evaporated and the residue is dissolved in DCM. The organic phase is washed with saturated aqueous NH$_4$Cl and brine, dried over MgSO$_4$ and evaporated to give 3.0 g of the crude desired product as a light yellow solid.

MS (ESI): 1035.6 ([MH]$^+$).

B] Preparation of Compound 11-B

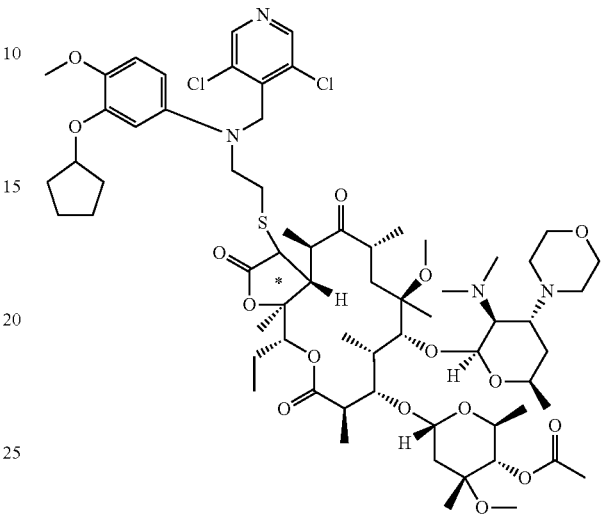

Compound 11-B is prepared from compound 11-A and compound 4-B (example 4, step B) following the procedures described in example 5 step F and example 10 step A.

C] Preparation of Compound I-11

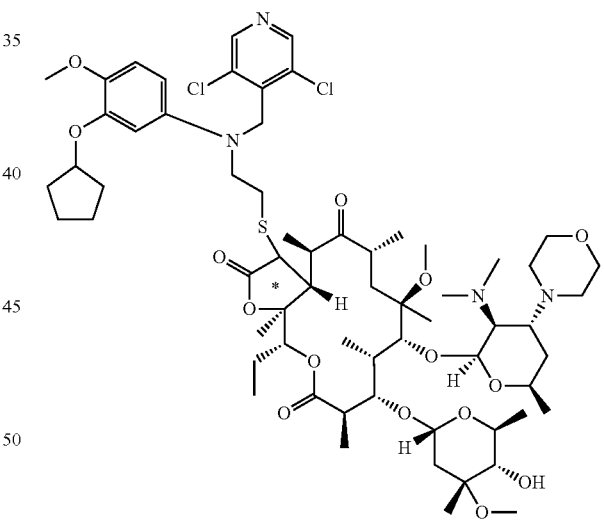

655 mg of compound II-B is dissolved in 20 ml of methanol and 0.4 ml of DBU is added. The reaction mixture is stirred at 70° C. for 5 hours. The solvent is removed under reduced pressure and the residue is dissolved in DCM. The organic layer was washed with water and brine, dried over MgSO$_4$ and concentrated in vacuo to give the crude product (0.64 g) as a yellow solid. The crude product is purified by flash chromatography on silica gel (DCM/MeOH 80:1→20:1) to give 0.5 g of the desired product which was further purified by preparative HPLC (system Ap) to give 200 mg of the desired product.

MS (ESI): 1265.7 [MH]$^+$, 633.6 [MH$_2$]$^{++}$
Ret. Time (system Ba): 41.1 min.

Example 12

Preparation of I-12, compound of formula I where R1 is [2-[(3-cyclopentyloxy-4-methoxy-phenyl)-(3,5-dichloropyridin-4-yl-methyl)-amino]ethyl]thio, R2 is —OH, R5 is dimethylamino, R8 is 4-morpholinyl and R3, R4, R6, R7 and R9 are hydrogen.

A] Preparation of Compound I-12

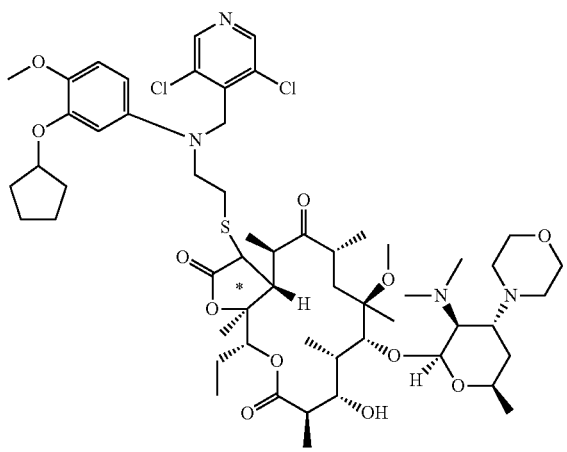 [SMILES: CC[C@H]1OC(=O)[C@H](C)[C@@H](O)[C@H](C)[C@@H](O[C@@H]2O[C@H](C)C[C@@H](N3CCOCC3)[C@@H]2N(C)C)[C@](C)(OC)C[C@@H](C)C(=O)[C@H](C)[C@H]2C(SCCN(Cc3c(Cl)cncc3Cl)c3ccc(OC)c(OC4CCCC4)c3)C(=O)O[C@@]21C]

655 mg of compound II-B is dissolved in 30 ml of methanol and 2 ml of concentrated HCl is added and the reaction is stirred at 25-28° C. After 24 hours additional 3 ml of concentrated HCl is added and the mixture is stirred for 30 hours. Methanol is evaporated and the remaining aqueous solution is neutralized with an aqueous NaOH solution. The aqueous layer is extracted twice with 50 ml DCM. The combined organic layers are washed with brine, dried over MgSO$_4$ and concentrated in vacuo to give the crude product (0.65 g). 400 mg of this crude product are purified by preparative HPLC (system Ap) to give 100 mg of the desired product.

MS (ESI): 1107.6 [MH]$^+$, 554.5 [MH$_2$]$^{++}$

Ret. Time (system Ba): 38.0 min.

Example 13

Preparation of I-13, compound of formula I where R1 is [2-[(3-cyclopropylmethyl-4-methoxy-phenyl)-(3,5-dichloropyridin-4-yl-methyl)-amino]ethyl]thio, R2 is —O-cladinosyl, R6 taken together with R7 is —O(CO)N(CH$_3$)— and R3, R4, R5, R8 and R9 are hydrogen.

A] Preparation of Compound 13-A

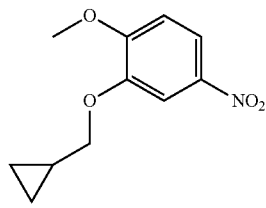 [SMILES: COc1ccc([N+](=O)[O-])cc1OCC1CC1]

5.0 g (29.5 mmol) of 2-methoxy-5-nitrophenol are dissolved under an atmosphere of nitrogen in 400 ml of acetone and 20.4 g (148 mmol) potassium carbonate, 13.4 g (148 mmol) (chloromethyl)-cyclopropane and 5 g (29.5 mmol) potassium iodide are added. The reaction mixture was heated to reflux for 30 hours, cooled to room temperature and the solids are removed by filtration. The filtrate is evaporated and the residue is dissolved in ethyl acetate and filtered through silica gel. The filtrate was evaporated to give the crude product as a light yellow solid. This solid was washed with petroleum ether to give 5.5 g of the desired product as a light yellow solid.

B] Preparation of Compound 13-B

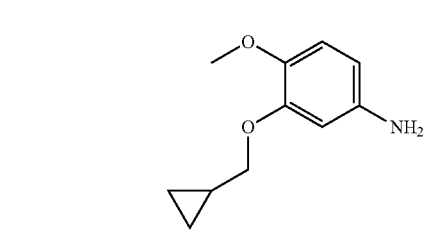

0.2 g (0.9 mmol) of compound 13-A is dissolved in 6 ml ethanol and 48 mg of palladium on charcoal (5%) are added. The mixture is stirred under an atmosphere of hydrogen gas for 3 hours at 25° C. The catalyst is filtered off through a layer of silica gel and the filtrate was evaporated under reduced pressure to give 170 mg of the desired crude product as a red oil.

C] Preparation of Compound 13-C

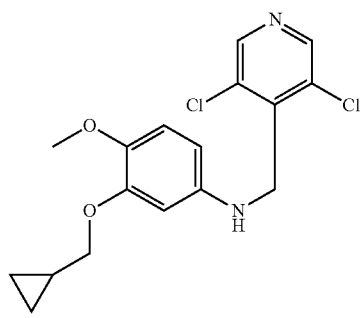 [SMILES: COc1ccc(NCc2c(Cl)cncc2Cl)cc1OCC1CC1]

To a solution of 4.1 g (21.22 mmol) in 60 ml toluene are added 3.8 g (21.64 mmol) 3,5-dichloro-4-pyridinecarboxaldehyde, 12 ml (84.9 mmol) triethylamine and 6 ml (106 mmol) acetic acid. The mixture is stirred at 25° C. for 2 hours and 5.33 g (84.9 mmol) NaBH$_3$CN are added. The reaction mixture is stirred at 25° C. for 3 hours and then to solvent is evaporated. The residue is purified by flash chromatography on silica gel (petroleum ether/ethyl acetate 20:1) to give 6.75 g of the desired product as a yellow solid.

MS (ESI): 353.0, 355.0 ([MH]$^+$).

D] Preparation of Compound 13-D

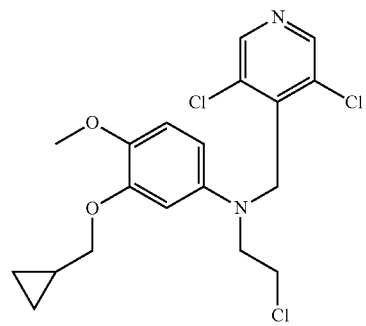 [SMILES: COc1ccc(N(CCCl)Cc2c(Cl)cncc2Cl)cc1OCC1CC1]

Compound 13-D is prepared from compound 13-C following the procedure described in example 4 step B.

E] Preparation of Compound 13-E

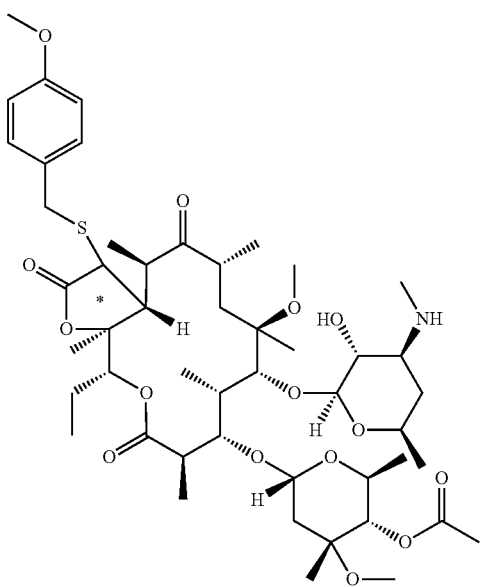 [SMILES: CC[C@H]1OC(=O)[C@H](C)[C@@H](O[C@H]2C[C@@](C)(OC)[C@@H](OC(C)=O)[C@H](C)O2)[C@H](C)[C@@H](O[C@@H]2O[C@H](C)C[C@H](NC)[C@H]2O)[C@](C)(OC)C[C@@H](C)C(=O)[C@H](C)[C@H]2C(SCc3ccc(OC)cc3)C(=O)O[C@@]21C]

9.8 g (9.7 mmol) of the compound of formula XXVIII wherein $Rp_1$ and $Rp_2$ are acetyl (WO2008/017696, example 1, product of step K) are dissolved in 100 ml methanol and 20 ml of water and 4.1 g (48.6 mmol) of sodium acetate and 10 g (38.8 mmol) of iodine are added. The dark mixture is heated to 45° C. for 3 hours. The reaction mixture is quenched with a 1M aqueous solution of $Na_2S_2O_3$. The solvent is removed in vacuo and 50 ml of water are added to the residue. The mixture is extracted 3 times with DCM. The combined organic layers are washed with water and with brine, dried over $Na_2SO_4$, filtered and concentrated in vacuo to give the crude product as yellow foam. The crude product is purified by flash chromatography on silica gel (DCM/MeOH 40:1) to give 5.4 g of the desired product as a light yellow foam.

MS (ESI): 952.3 ([MH]$^+$).

F] Preparation of Compound 13-F

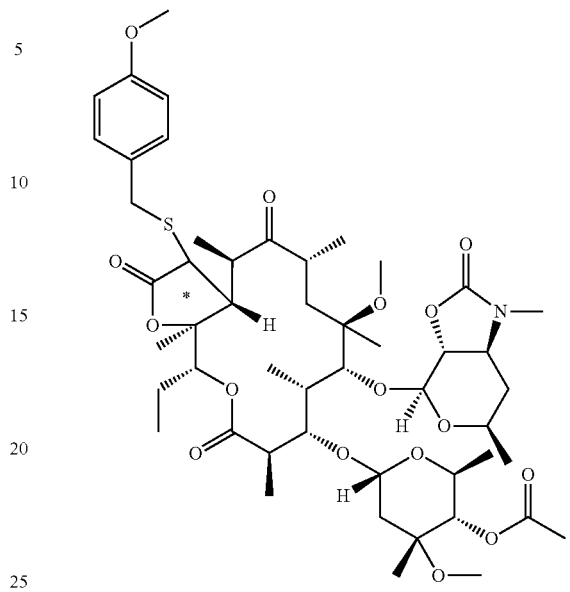

1 g (1.05 mmol) of compound 13-E is dissolved in 11 ml dioxane and 3.2 ml 1N NaOH is added at 0° C. Now 343 mg (1.16 mmol) bis(trichlormethyl)carbonate is added and the mixture is stirred for 2 hours at room temperature. 30 ml of saturated aqueous $NH_4Cl$ is added and the mixture is extracted with 200 ml of ethyl acetate. The organic layer is washed three times with 50 ml of water and with 50 ml brine, dried over $Na_2SO_4$ and concentrated in vacuo to give the crude product as light yellow solid. The crude product is purified by flash chromatography on silica gel (DCM/MeOH 200:1) to give 700 mg of the desired product as white solid.

G] Preparation of Compound 13-G

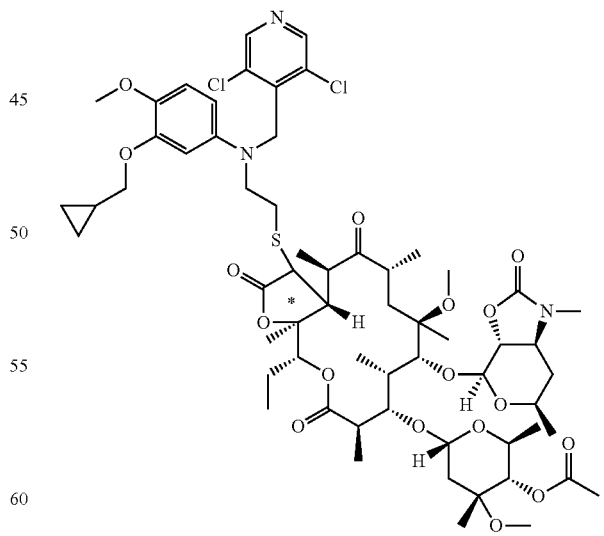

Compound 13-G is prepared from compound 13-F and compound 13-D (example 13, step D) following the procedures described in example 5 step F and example 10 step A.

MS (ESI): 1236.6, 1238.6 ([MH]$^+$).

H] Preparation of Compound I-13

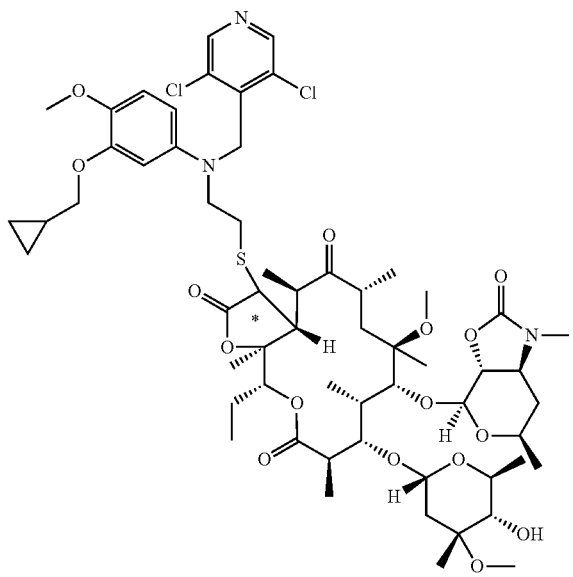 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H]3[C@H]2OC(=O)N3C)[C@](C)(OC)C[C@@H](C)C(=O)[C@H](C)[C@H]2C(SCCN(Cc3c(Cl)cncc3Cl)c3ccc(OC)c(OCC4CC4)c3)C(=O)O[C@@]21C]

75 mg of compound 13-G is dissolved in 5 ml methanol and 46 mg DBU is added. The mixture is stirred at 70° C. for 2 hours. The solvent is evaporated and the crude product is purified twice by preparative TLC (DCM/MeOH 25:1) to give 35 mg of the desired product which is further purified by flash chromatography on silica gel (DCM/MeOH 25:1) to give 27 mg of the desired product as white foam.

MS (ESI): 1194.6, 1196.6 [MH]+
Ret. Time (system Ba): 46.5 min

Example 14

Preparation of I-14, compound of formula I where R1 is [2-[5-(3,5-dichloropyridine-4-yl-aminocarbonyl)-2-methoxy-phenoxy]ethyl]thio, R2 is —O-cladinosyl, R6 is —OH, R7 is acetyl-methyl-amino and R3, R4, R5, R8 and R9 are hydrogen.

A] Preparation of Compound 14-A

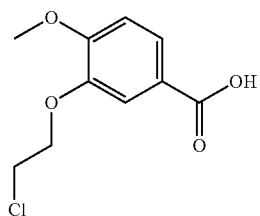

500 mg (2.97 mmol) of isovanillic acid are dissolved in 5 ml DMF and 1.07 g (7.74 mmol) potassium carbonate and 0.7 ml (8.49 mmol) 1-bromo-2-chloroethane are added. The mixture is heated to 50° C. for 6 hours and to 70° C. for one hour. Subsequently DMF is evaporated and 20 ml of water is added to the residue. The aqueous layer is extracted twice with 50 ml of ethyl acetate. The organic layers are combined and the solvent is evaporated under reduced pressure. The residue is dissolved in 20 ml THF and 20 ml methanol and 20 ml of 4N aqueous NaOH is added. The reaction mixture is stirred for 2 hours at room temperature and the organic solvents are evaporated. The aqueous phase is adjusted to pH=7 with concentrated aqueous HCl leading to precipitation of the product which is isolated by filtration and washed with water to give 347 mg of the desired product as grey solid.

B] Preparation of Compound 14-B

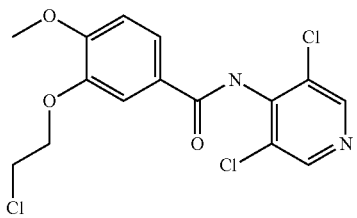 [SMILES: COc1ccc(C(=O)Nc2c(Cl)cncc2Cl)cc1OCCCl]

31 mg (0.74 mmol) sodium hydride are dissolved in 2 ml DMF and 134 mg (0.82 mmol) of 4-amino-3,5-dichloropyridine is added. The mixture is stirred for 3 hours at 28° C. to give "solution A".

50 mg (0.22 mmol) of compound 14-A, 99 mg (0.26 mmol) of HATU and 45 µl (0.26 mmol) of ethyldiisopropylamine are dissolved in 20 ml DMF and the resulting solution is stirred at 29° C. for 45 minutes. Solution A (see above) is added dropwise at 0-10° C. and the mixture is stirred at this temperature for 15 minutes. The pH of the mixture is adjusted to 6 by addition of aqueous HCl and DMF is evaporated under reduced pressure. The residue is dissolved in 70 ml ethyl acetate and the organic layer is washed twice with 50 ml 0.5 N aqueous HCl, with 50 ml water and twice with 50 ml brine, dried over $Na_2SO_4$ and concentrated in vacuo to give 120 mg of the crude product as brown solid. The crude product is purified by flash chromatography on silica gel (ethyl acetate/petroleum ether 1:2) to give 60 mg of the desired product as white solid.

$^1$H NMR (DMSO-d6): 3.86 (s, 3H), 3.96 (t, 2H), 4.30 (t, 2H), 7.14 (d, 1H), 7.58 (d, 1H), 7.70 (dd, 1H), 8.73 (s, 2H), 10.45 (s, 1H)

C] Preparation of Compound 14-C

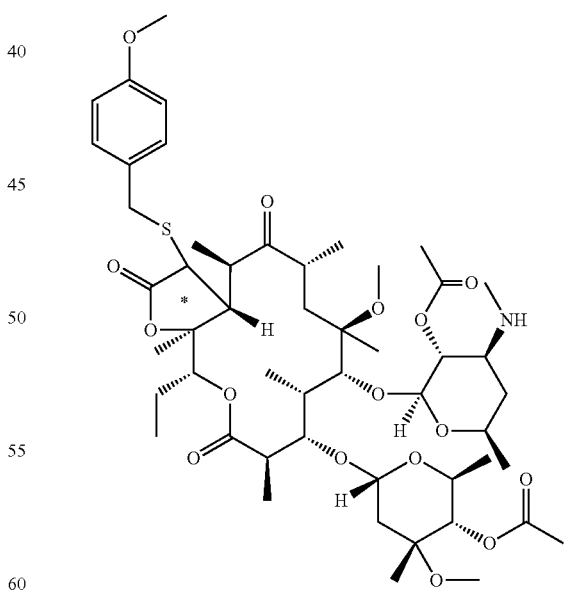

2.0 g (2.0 mmol) of compound 5-B are dissolved in 80 ml of methanol and 8 ml of water and 0.83 g (10.0 mmol) of sodium acetate are added. The mixture is stirred at room temperature for 10 minutes and 2.5 g (10.0 mmol) of iodine are added. The dark mixture is stirred at 25-30° C. for 2 hours and subsequently quenched with a 1M aqueous solution of Na₂S₂O₃. The solvent is removed in vacuo and the aqueous layer is extracted twice with 50 ml DCM. The combined organic layer is washed with water and with brine, dried over MgSO₄, filtered and concentrated in vacuo to give the crude product (2.0 g) as light yellow solid. The product was used without further purification for the next step.

MS (ESI): 994.6 [MH]⁺

D] Preparation of Compound 14-D

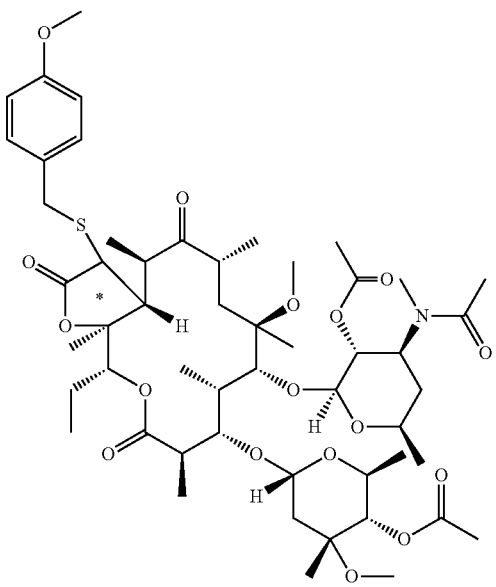 [SMILES: CC[C@H]1OC(=O)[C@H](C)[C@@H](O[C@H]2C[C@@](C)(OC)[C@@H](OC(C)=O)[C@H](C)O2)[C@H](C)[C@@H](O[C@@H]2O[C@H](C)C[C@H](N(C)C(C)=O)[C@H]2OC(C)=O)[C@](C)(OC)C[C@@H](C)C(=O)[C@H](C)[C@H]2C(SCc3ccc(OC)cc3)C(=O)O[C@@]21C]

To a solution of 3.81 g (4 mmol) of compound 14-C in 50 ml DCM is added 1.23 g (10 mmol) DMAP and 1.14 ml (12 mmol) acetic anhydride and the mixture is stirred at 25-28° C. for 20 hours. The organic layer is washed three times with saturated aqueous NH₄Cl, with water and brine, dried over MgSO₄, filtered and concentrated in vacuo to give the crude product which is purified by flash chromatography on silica gel (DCM/MeOH 100:1) to give 3.4 g of the desired product as light yellow solid.

MS (ESI): 1058.8 [MNa]⁺

E] Preparation of Compound 14-E

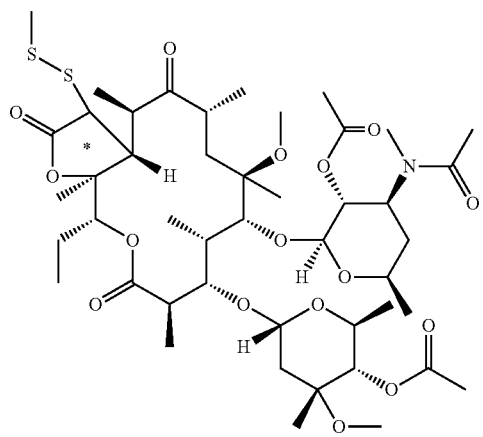 [SMILES: CC[C@H]1OC(=O)[C@H](C)[C@@H](O[C@H]2C[C@@](C)(OC)[C@@H](OC(C)=O)[C@H](C)O2)[C@H](C)[C@@H](O[C@@H]2O[C@H](C)C[C@H](N(C)C(C)=O)[C@H]2OC(C)=O)[C@](C)(OC)C[C@@H](C)C(=O)[C@H](C)[C@H]2C(SSC)C(=O)O[C@@]21C]

2.0 g (1.9 mmol) of the product of example 14, step D are dissolved in 100 ml DCM and 0.8 g (4.1 mmol) dimethyl (methylthio)sulfonium tetrafluoroborate and 0.8 g molecular sieves (4A) are added to the mixture and the reaction is stirred for 1 hour at 0-5° C. The molecular sieves is filtered off and washed with 60 ml DCM. The combined organic layers are washed twice with aqueous NaHCO₃ (5%), with water and with brine, dried over MgSO₄ and concentrated in vacuo to give 2 g of the desired product as a light yellow solid. The crude product is used without purification for the next step.

F] Preparation of Compound 14-F

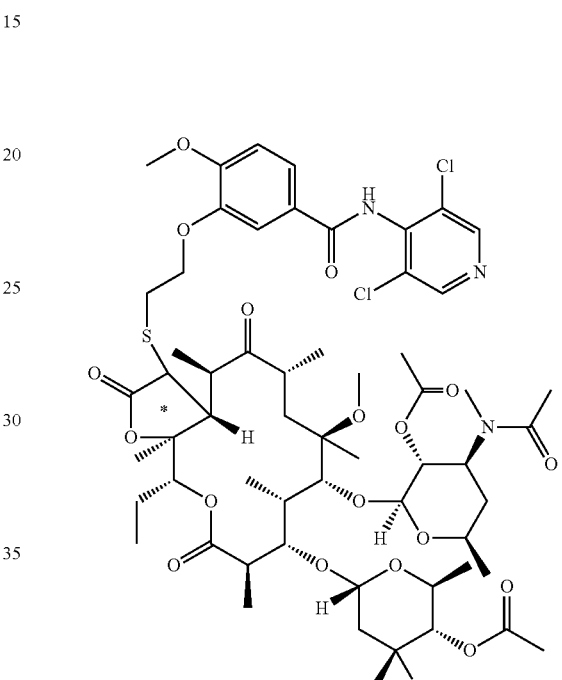

1.9 g (2.0 mmol) of the compound 14-E is dissolved under nitrogen atmosphere in 50 ml DMF and 2 ml of water and 1.0 ml (4.0 mmol) of tributylphosphine are added and the mixture is stirred at 0-5° C. until no starting material remained (1 h). Then 750 mg (2.0 mmol) of 3-(2-chloro-ethoxy)-N-(3,5-dichloro-pyridin-4-yl)-4-methoxy-benzamide (compound 14-B), 0.6 ml DBU (4.0 mmol) and 170 mg (0.5 mmol) KI are added to the solution. The reaction is stirred for 12 hours at room temperature and 50 ml of water is added. The mixture is extracted 3 times with 100 ml DCM. The combined organic layers are washed with saturated aqueous NH₄Cl, with water and brine, dried over MgSO₄ and concentrated in vacuo to give the crude product which is purified by flash chromatography on silica gel (DCM/MeOH 120:1→40:1) to give 1.4 g of the desired product as light yellow solid.

MS (ESI): 1253.7 [MH]⁺

G] Preparation of Compound I-14

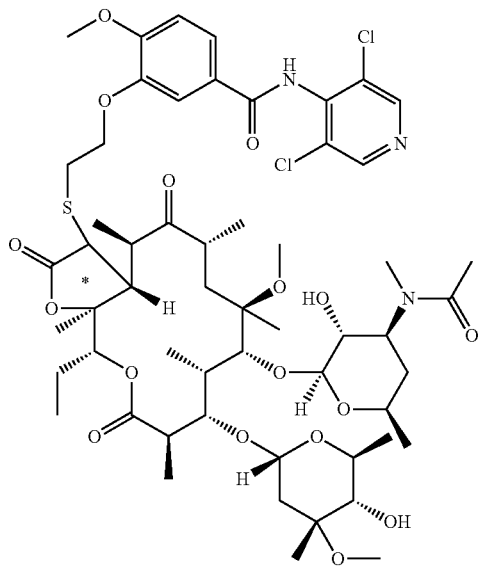 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C(C)=O)[C@H]2O)[C@](C)(OC)C[C@@H](C)C(=O)[C@H](C)[C@H]2C(SCCOc3cc(C(=O)Nc4c(Cl)cncc4Cl)ccc3OC)C(=O)O[C@@]21C]

1.3 g (0.42 mmol) of compound 14-F is dissolved in 50 ml of methanol and 1.0 ml (6.6 mmol) DBU is added. The mixture is heated to 70° C. for 30 hours. The solvent is removed under reduced pressure and the residue is dissolved in DCM. The organic layer is washed with water and brine, dried over MgSO$_4$ and concentrated in vacuo to give the crude product as light yellow solid. The crude product is purified by flash chromatography on silica gel (DCM/MeOH 80:1→30:1) to give 0.3 g of the desired product which was further purified by preparative HPLC (Column: Phenomenex Gemini C18, 110A 150×21.5 mm; flow: 16 ml/min; mobile phase A: 25 mM aqueous ammoniumacetate, mobile phase B: acetonitrile; gradient: 0-10 min linear from 55% B to 80% B) to give 230 mg of the desired product.

MS (ESI): 1170.5, 1172.5 [MH]$^+$

Ret. Time (system Ba): 37.0 min.

Example 15

Preparation of I-15, compound of formula I where R1 is [2-[5-(3,5-dichloropyridine-4-yl-aminocarbonyl)-2-methoxy-phenoxy]ethyl]thio, R2 is —O-cladinosyl, R6 is —OH, R7 is methyl-(morpholine-4-carbonyl)-amino and R3, R4, R5, R8 and R9 are hydrogen.

A] Preparation of Compound 15-A

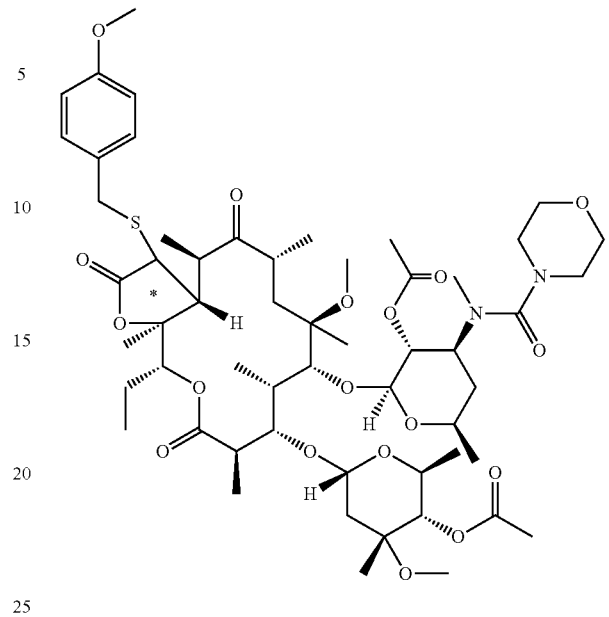

2.0 g (2.0 mmol) of compound 14-C are dissolved in 100 ml THF and 140 mg (6.0 mmol) NaH are added under an atmosphere of nitrogen at 0° C. The mixture is stirred a 0-5° C. for 10 minutes and 1.2 ml (10 mmol) of 4-morpholinecarbonyl chloride are added. The mixture is stirred at 0-25° C. for 18 hours and at 30-35° C. for two hours. The solvent is removed under reduced pressure and the residue is dissolved in DCM. The organic layer is washed with water and brine, dried over MgSO$_4$ and concentrated in vacuo to give the crude product as light yellow solid. The crude product is purified by flash chromatography on silica gel (DCM/MeOH 50:1→100:1) to give 1.8 g of the desired product as white solid.

MS (ESI): 1129.6 [MNa]$^+$

B] Preparation of I-15

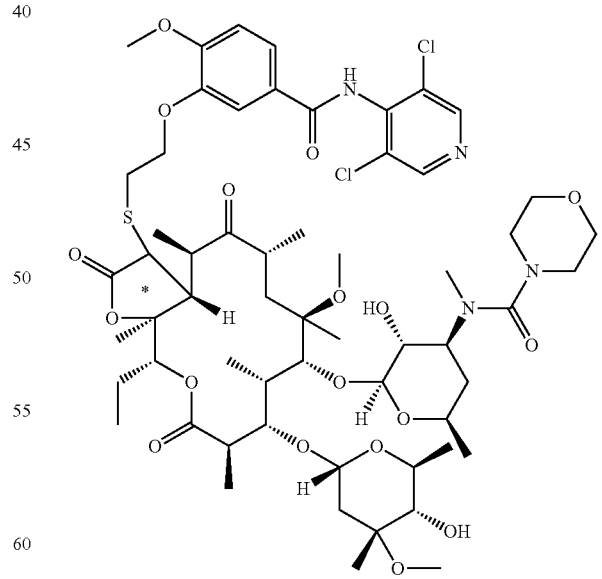

Compound I-15 is prepared from compound 15-A and compound 14-B (example 14, step B) following the procedures described in example 14 steps E-G.

MS (ESI): 1241.6 [MH]$^+$

Ret. Time (system Ba): 38.8 min.

Example 16

Preparation of I-16, compound of formula I where R1 is [2-[5-(3,5-dichloropyridine-4-yl-aminocarbonyl)-2-methoxy-phenoxy]propyl]thio, R2 is —O-cladinosyl, R6 is —OH, R7 is methyl-(morpholine-4-carbonyl)-amino and R3, R4, R5, R8 and R9 are hydrogen.

A] Preparation of Compound 16-A

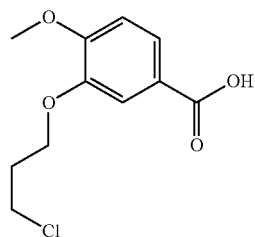 [SMILES: COc1ccc(C(=O)O)cc1OCCCCl]

200 mg (1.19 mmol) of isovanillic acid are dissolved in 10 ml DMF and 493 mg (3.57 mmol) potassium carbonate and 0.35 ml (3.57 mmol) 1-bromo-3-chloropropane are added. The mixture is heated to 50° C. for 4 hours. Subsequently 20 ml of water is added and the aqueous layer is extracted twice with 20 ml of ethyl acetate. The organic layers are combined and the solvent is evaporated under reduced pressure. The residue is dissolved in 20 ml THF and 20 ml methanol and 20 ml of 4N aqueous NaOH is added. The reaction mixture is stirred for 2 hours at room temperature and the organic solvents are evaporated. The aqueous phase is adjusted to pH=7 with concentrated aqueous HCl leading to precipitation of the product which is isolated by filtration and washed with water to give 100 mg of the desired product as white solid.

B] Preparation of Compound 16-B

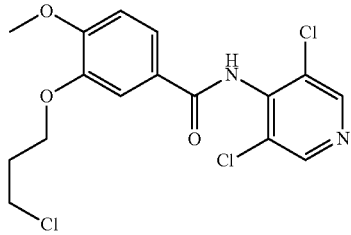 [SMILES: COc1ccc(C(=O)Nc2c(Cl)cncc2Cl)cc1OCCCCl]

Compound 16-B is prepared from compound 16-A following the procedure described in example 14 step B.

$^1$H NMR (DMSO-d6): 2.16-2.20 (m, 2H), 3.78-3.81 (m, 2H), 3.84 (s, 3H), 4.12-4.15 (m, 2H), 7.12 (d, 1H), 7.59 (s, 1H), 7.67 (d, 1H), 8.72 (s, 2H), 10.40 (bs, 1H)

C] Preparation of Compound 1-16

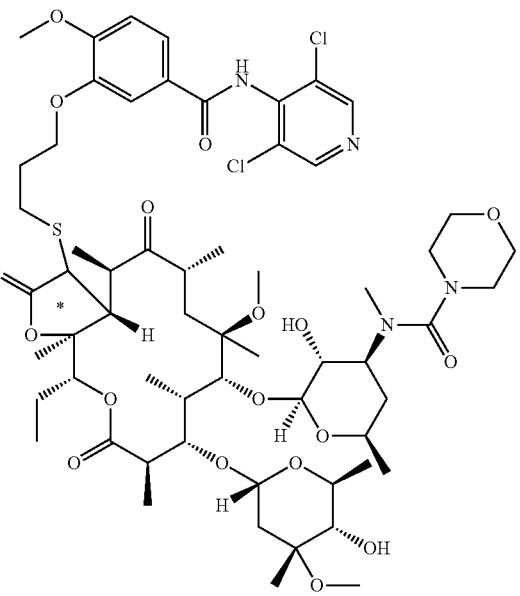

Compound I-16 is prepared from compound 15-A and compound 16-B following the procedures described in example 14 steps E-G.

MS (ESI): 1255.7 [MH]$^+$
Ret. Time (system Ba): 39.4 min.

Example 17

Preparation of I-17, compound of formula I where R1 is [2-[5-(3,5-dichloropyridine-4-yl-aminocarbonyl)-2-methoxy-phenoxy]propyl]thio, R2 is O-cladinosyl, R6 is —OH, R7 is isobutyl-methyl-amino and R3, R4, R5, R8 and R9 are hydrogen.

A] Preparation of Compound I-17

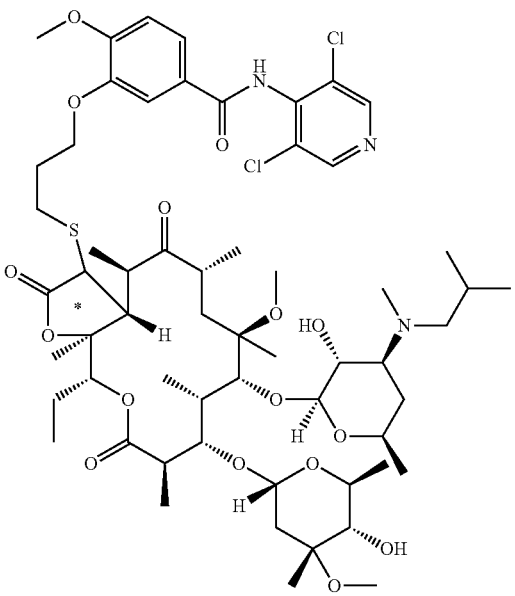 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)CC(C)C)[C@H]2O)[C@](C)(OC)C[C@@H](C)C(=O)[C@H](C)[C@H]2C(SCCCOc3cc(C(=O)Nc4c(Cl)cncc4Cl)ccc3OC)C(=O)O[C@@]21C]

Compound I-17 is prepared from compound 2-B and compound 16-B following the procedures described in example 2 steps E-F.

MS (ESI): 1198.8 [MH]+

Ret. Time (system Ba): 35.1 min.

Example 18

Preparation of I-18, compound of formula I where R1 is [2-[(3-cyclopentyloxy-4-methoxy-phenyl)-(3,5-dichloropyridin-4-yl-methyl)-amino]ethyl]thio, R2 is —O-cladinosyl, R6 is hydroxy, R8 and R9 taken together with the bond between the carbon atoms to which they are linked form a double bond, and R3, R4, R5 and R7 are hydrogen.

A] Preparation of Compound 18-A

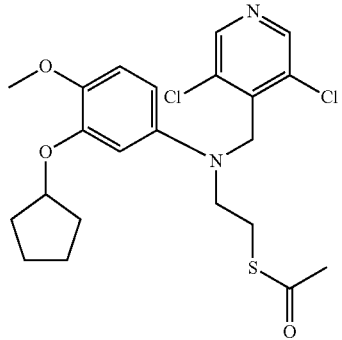 [SMILES: COc1ccc(N(CCSC(C)=O)Cc2c(Cl)cncc2Cl)cc1OC1CCCC1]

0.6 g (1.4 mmol) of compound 4-B is dissolved in 8 ml of acetone and 0.21 g (1.8 mmol) potassium thioacetate is added. The mixture is stirred at 60° C. for 36 hours and the solvent is evaporated. The residue is dissolved in 100 ml ethyl acetate and the organic layer is washed three times with brine, dried over Na2SO4 and concentrated in vacuo to give the crude product which is purified by flash chromatography on silica gel (ethyl acetate/petroleum ether 1:20) to give 90 mg of the desired product as brown oil and 520 mg of compound 4-B.

MS (ESI): 469.1 [MH]+

B] Preparation of Compound 18-B

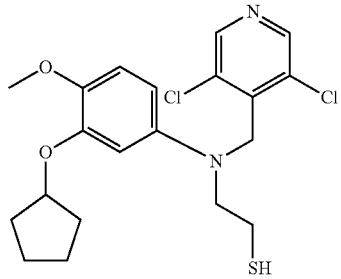 [SMILES: COc1ccc(N(CCS)Cc2c(Cl)cncc2Cl)cc1OC1CCCC1]

90 mg of compound 18-A is dissolved in 6 ml of methanol and ammonia gas is bubbled into the solution for 5 minutes. Stirring is continued for 30 minutes and the solvent is evaporated. The product is used directly for the next step.

C] Preparation of 18-C

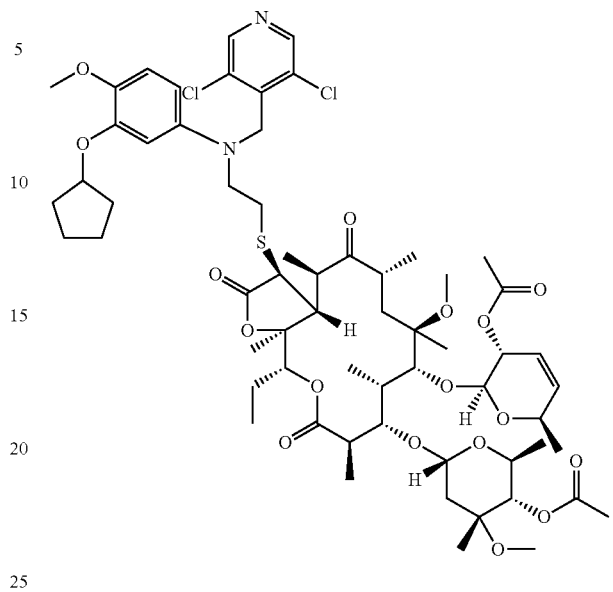

Compound 18-C is prepared from compound 18-B and compound 1-F following the procedures described in example 1 steps G-H.

D] Preparation of Compound I-18

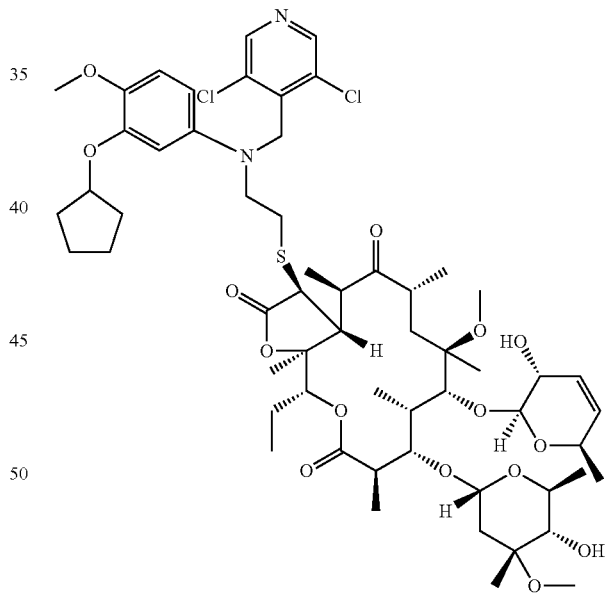

60 mg of crude compound 18-C is dissolved in 3 ml methanol and 15 mg DBU is added. The mixture is stirred for 24 hours at room temperature. 60 mg of DBU are added and the mixture is stirred for 24 hours at room temperature and 24 hours at 40° C. The solvent is removed under reduced pressure and the residue is purified by flash chromatography on silica gel (DCM/MeOH 250:1) to give 3 mg of the desired product.

MS (ESI): 1151.3, 1153.3 [MH]+

Ret. Time (system Ba): 48.2 min.

Example 19

Preparation of I-19, compound of formula I where R1 is [2-[(3-cyclopentyloxy-4-methoxy-phenyl)-(3,5-dichloropyridin-4-yl-methyl)-amino]ethyl]thio, R2 is —O-cladinosyl, R6 is hydroxy, and R3, R4, R5, R7, R8 and R9 are hydrogen.

A] Preparation of Compound 19-A

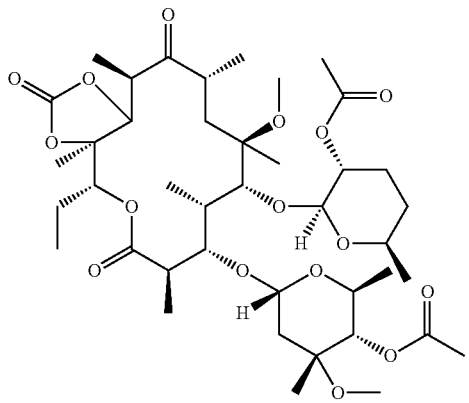 [SMILES: CC[C@H]1OC(=O)[C@H](C)[C@@H](O[C@H]2C[C@@](C)(OC)[C@@H](OC(C)=O)[C@H](C)O2)[C@H](C)[C@@H](O[C@@H]2O[C@H](C)CC[C@H]2OC(C)=O)[C@](C)(OC)C[C@@H](C)C(=O)[C@H](C)C2OC(=O)O[C@@]21C]

200 mg of compound 1-D is dissolved in 5 ml of ethanol and 5 ml of ethyl acetate and 26 mg of palladium on charcoal (10%) are added. The mixture is stirred under an atmosphere of hydrogen gas at 28° C. for 16 hours. The reaction mixture is filtered through a layer of silica gel and the filtrate is evaporated to give 0.2 g of the desired product as a white solid.

B] Preparation of I-19

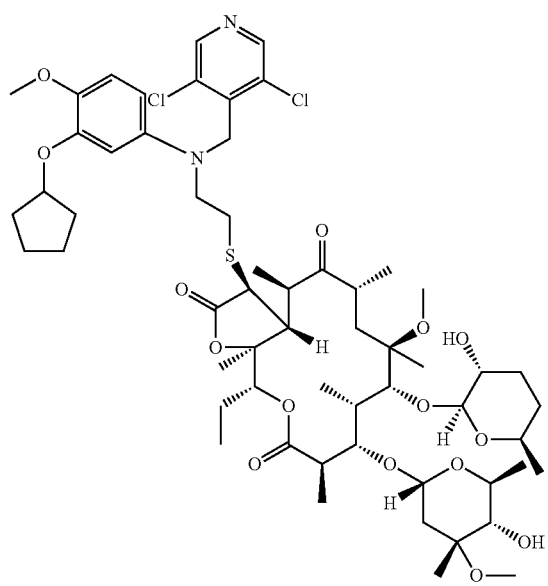

Compound I-19 is prepared from compound 19-A and compound 4-B following the procedures described in example 1 steps E-H, in example 14 steps E-G and in example 18 step D.

MS (ESI): 1153.5, 1155.5 [MH]$^+$

Ret. Time (system Ba): 49.0 min.

Example 20

Preparation of I-20, compound of formula I where R1 is [2-[5-(3,5-dichloropyridine-4-yl-aminocarbonyl)-2-methoxy-phenoxy]ethyl]thio, R2 is —O-cladinosyl, R6 is —OH, R7 is (2-dimethylaminoacetyl)-methyl-amino and R3, R4, R5, R8 and R9 are hydrogen.

A] Preparation of Compound 20-A

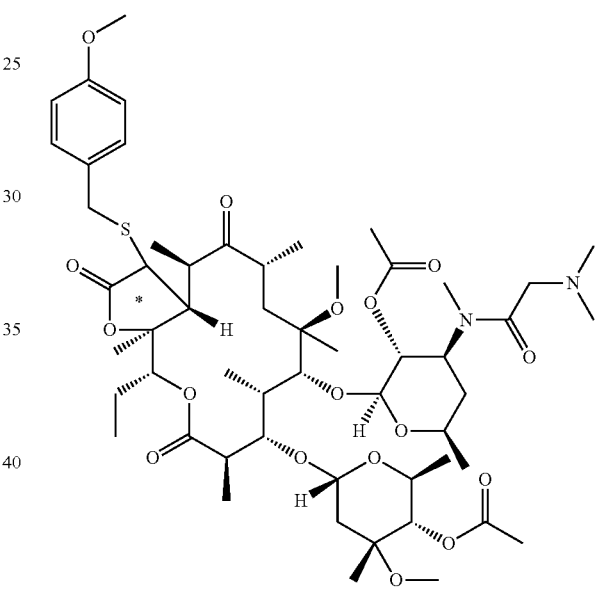

2.5 g (2.51 mmol) of compound 14-C are dissolved in 20 ml of DMF and 1.91 g (5.03 mmol) HATU, 1.63 g (12.6 mmol) ethyldiisopropylamine and 0.88 g (6.29 mmol) N,N-dimethylglycine hydrochloride are added and the mixture is stirred at 15° C. for 20 hours. Water is added and the mixture is extracted twice with 150 ml of DCM. The combined organic layers are washed with water and brine, dried over MgSO$_4$ and concentrated in vacuo to give the crude product which is purified by flash chromatography on silica gel (DCM/MeOH 50:1) to give 1.75 g of the desired product as light yellow solid. MS (ESI): 1079.6 [MH]$^+$ B] Preparation of Compound I-20

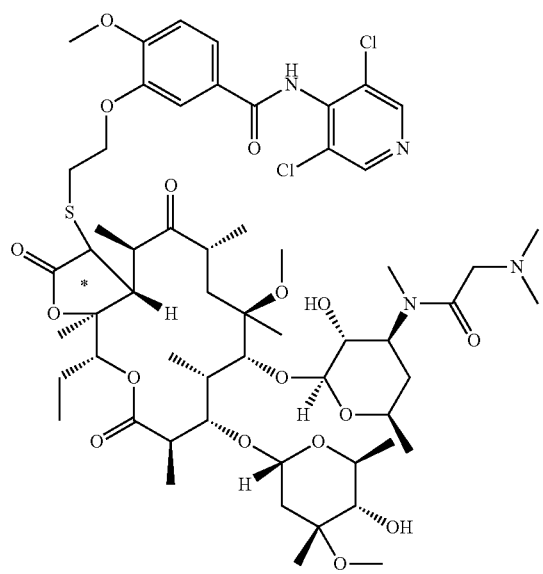 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C(=O)CN(C)C)[C@H]2O)[C@](C)(OC)C[C@@H](C)C(=O)[C@H](C)[C@H]2C(SCCOc3cc(C(=O)Nc4c(Cl)cncc4Cl)ccc3OC)C(=O)O[C@@]21C]

Compound I-20 is prepared from compound 20-A and compound 14-B following the procedures described in example 14 steps E-G.

MS (ESI): 1213.5, 1215.5 [MH]+

Ret. Time (system Ba): 32.3 min.

Biological Activity

The compounds of the invention exhibit substantial inhibitory activity towards human phosphodiesterases (PDEs), in particular towards PDE4. The following assay has been used to determine the inhibitory activity of the compounds.

Assay

PDE4 specifically hydrolyzes cAMP and releases the product AMP. The potency of PDE inhibition by said agents is determined in an in vitro enzymatic assay. The assay is commercially available (IMAP™ FP assay Molecular Devices Corp. (MDS)) and is optimized for the use of human PDE4. Fluorescently labeled cAMP is hydrolyzed by PDE4 and in a second step, binding of labeled product to a large binding partner allowed product detection by fluorescence polarization (FP) measurements.

PDE4 is partially purified from undifferentiated human monocytic cells (U-937) according to Thorpy et al. 1992 (*J. Pharmacol. Exp. Ther.* 263: 1195). Final preparations are specific for cAMP and did not hydrolyze cGMP above the detection limit of the assay. In addition, PDE4 preparations are validated by inhibition studies with PDE4-specific and unspecific PDE inhibitors.

Stock solutions of test compounds are made in DMSO and diluted in assay buffer (10 mM Tris-HCl, 10 mM $MgCl_2$, 0.1% BSA 0.05% $NaN_3$, pH 7.2) to the desired concentrations. The solutions used in the assay contained test compound in assay buffer with 2% DMSO.

10 μl of substrate (at a concentration recommended by the manufacturer) are mixed with 5 μl of appropriately diluted PDE and 5 μl of test compound solution. 5 μl of reaction buffer with 2% DMSO are used for control reactions. The final concentration of DMSO in the assay is 0.5%, which did not significantly alter the PDE activity. After incubation for 90 minutes at room temperature, 60 μl of binding reagent are added as specified by the manufacturer. Binding is allowed to proceed for 30 minutes and fluorescence polarization is measured. Dose dependence of PDE inhibition is measured by assaying dilution series of test compounds in duplicates. $IC_{50}$ values are determined from the measured activities by curve fitting.

| Results | |
|---|---|
| Example | $IC_{50}$ (PDE4) [μM] |
| 1 | 4.8 |
| 2 | 2.8 |
| 3 | 13.6 |
| 5 | 0.11 |
| 6 | 1.4 |
| 7 | 0.14 |
| 8 | 0.22 |
| 9 | 0.30 |
| 10 | 0.031 |
| 11 | 0.014 |
| 12 | 0.22 |
| 13 | 0.018 |
| 14 | 0.0027 |
| 15 | 0.071 |
| 16 | 0.22 |

The invention claimed is:
1. Macrolide compound of formula I:

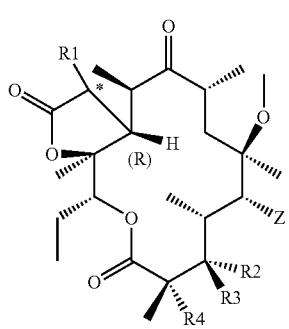

(I)

wherein
R1 is a residue -Y-X-Q;
Y is S, SO or $SO_2$;
X is a bond or a linear group consisting of hydrogen atoms and 1 to 9 atoms selected from C, N, O and S, of which up to 2 atoms can be N and one atom can be O or S, one carbon atom can appear as a CO group and the sulphur atom can appear as an $SO_2$ group and two adjacent C atoms can be present as —CH=CH— or —C≡C— and which group X is unsubstituted or is substituted with —COO—W or —CONH—W;
Q is a residue —V-A1-L-A2-W or, if X does not represent a bond, may also be —NR10R11
V is an optionally substituted divalent aromatic or heterocyclic group;
W is optionally substituted aryl or heterocyclyl;
A1 and A2 are, independently of each other, either absent or a $C_1$-$C_4$alkylene group;
L is —O—, —S—, —$SO_2$—, —NH—, —CO—, —(CO)O—, —O(OC)—, —(CO)NH—, —NH(CO)—, —($SO_2$)NH—, —HN($SO_2$)—, —HN(CO)NH—, —O(CO)NH—, —NH(CO)O—, or can also be absent if A1 and/or A2 are present;

R2 is OR2a or

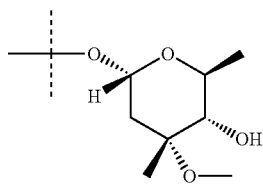

wherein

represents the bond between said group and the carbon atom of said macrolide compound to which it is linked;
R2a is hydrogen, acetyl, —(C═O)CH₂NR2bR2c, or —(C═O)CH₂CH₂NR2bR2c;
R2b and R2c independently of each other, are hydrogen or C1-C6 alkyl which can be substituted or unsubstituted and wherein up to two atoms can be N, O or S and one carbon atom can appear as C═O or, taken together with the nitrogen atom to which they are linked, form a 4-7 membered-ring of which up to two atoms can be N, O or S and one carbon can appear as C═O;
R3 is hydrogen or
R2 and R3 taken together with the carbon atom to which they are linked, represent a C═O group;
R4 is hydrogen or
R2 and R4 taken together with the bond between the carbon atoms to which they are linked, represent a double bond between said carbon atoms;
Z is

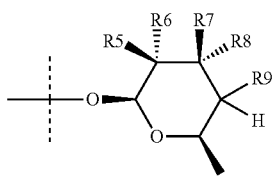

wherein

represents the bond between said group and the carbon atom of said macrolide compound to which it is linked;
R5 is hydrogen or —OR5a or —NR5bR5c;
R6 is hydrogen or —OR6a or —NR6bR6c; or
R5 and R6 taken together with the carbon atom to which they are linked, represent a C═O group;
R7 is hydrogen or —OR7a or —NR7bR7c;
R8 is hydrogen or —OR8a or —NR8bR8c; or
R7 and R8 taken together with the carbon atom to which they are linked, represent a C═O group; or one of
R5 and R6 taken together with one of
R7 and R8 represent a group of formula —NR56(CO)O— or —O(CO)NR78—
R9 is hydrogen or
R8 and R9 taken together with the bond between the carbon atoms to which they are linked, represent a double bond between said carbon atoms;
R5a,
R7a and R8a, independently of each other, are hydrogen or C1-C6 alkyl which can be substituted or unsubstituted and wherein one or more single bonds can be replaced by double and/or triple bonds and where one carbon atom can appear as C═O and up to two atoms can be N, O or S;
R6a is hydrogen or C1-C6 alkyl;
R56 and R78 are hydrogen or C1-C6 alkyl;
R5b, R5c,
R6b, R6c,
R7b, R7c,
R8b and R8c independently of one another, are hydrogen, C1-C6alkyl which can be substituted or unsubstituted and up to two atoms can be N, O or S and where one carbon atom can appear as C═O, or —(C═O)heterocyclyl or, taken together with the nitrogen atom to which they are linked, form a 4-7 membered-ring of which up to two atoms can be N, O or S and one carbon can appear as C═O;
R10 and R11 are independently selected from optionally substituted groups selected from aryl; aralkyl; heterocyclyl and heterocyclylalkyl; groups, and one of R10 and R11 can also be a group -L-A2-W; and
* indicates a chiral centre which is in the (R) or (S) form;
provided that
Z is not a group of formula

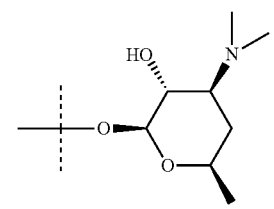

wherein

represents the bond between said group and the carbon atom of said macrolide compound to which it is linked,
or an acid addition salt, a N-oxide or an in vivo cleavable ester thereof.

2. A compound or an acid addition salt, a N-oxide thereof or an in vivo cleavable ester thereof according to claim 1, wherein one of
R5 and R6 and/or of R7 and R8 is hydrogen and the other is not hydrogen.

3. A compound or an acid addition salt, a N-oxide or an in vivo cleavable ester thereof according to claim 1, wherein R6a is hydrogen.

4. A compound or an acid addition salt, a N-oxide or an in vivo cleavable ester thereof according to claim 1, wherein
R5 is —NR5bR5c or
R7 is —NR7bR7c.

5. A compound or an acid addition salt, a N-oxide or an in vivo cleavable ester thereof according to claim 1, wherein
R6 is —OR6a or
R8 is —OR8a.

6. A compound or an acid addition salt, a N-oxide or an in vivo cleavable ester thereof according to claim 1, wherein
R8 and R9 taken together with the bond between the carbon atoms to which they are linked, form a double bond.

7. A compound or an acid addition salt, a N-oxide or an in vivo cleavable ester thereof compound according to claim 1, wherein
R9 is hydrogen.

8. A compound or an acid addition salt, a N-oxide or an in vivo cleavable ester thereof compound according to claim 1, wherein R5a, R7a and R8a, independently of each other are hydrogen, C1-C6 alkyl or vinyl.

9. A compound or an acid addition salt, a N-oxide or an in vivo cleavable ester thereof compound according to claim 1, wherein R5a, R7a, R8a, R56 and R78, R5b, R5c, R6b, R6c, R7b, R7c, R8b and R8c, independently of each other, are hydrogen or C1-C6 alkyl.

10. A compound or an acid addition salt, a N-oxide or an in vivo cleavable ester thereof according to claim 1, wherein
R2 is

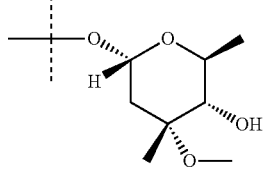

wherein

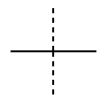

represents the bond between said group and the carbon atom of said macrolide compound to which it is linked.

11. A compound or an acid addition salt, a N-oxide or an in vivo cleavable ester thereof according to claim 1, wherein R2a is hydrogen.

12. A compound or an acid addition salt, a N-oxide or an in vivo cleavable ester thereof according to claim 1, wherein R2 and R3 taken together with the carbon atom to which they are linked, represent a C═O group.

13. A compound or an acid addition salt, a N-oxide or an in vivo cleavable ester thereof according to claim 1, wherein
R2 and R4 taken together with the bond between the carbon atoms to which they are linked, form a double bond.

14. A compound or an acid addition salt, a N-oxide or an in vivo cleavable ester thereof according to claim 1, wherein
Y is $SO_2$ or S.

15. A compound or an acid addition salt, a N-oxide or an in vivo cleavable ester thereof according to claim 1, wherein
Q is a residue —V-A1-L-A2-W.

16. A compound or an acid addition salt, a N-oxide or an in vivo cleavable ester thereof according to claim 1, wherein
V is a divalent group of formula

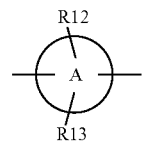

wherein

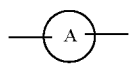

is a phenylene ring or a x-member saturated or unsaturated divalent heterocycloaliphatic or heteroaromatic ring containing from 2 to (x−1) carbon atoms with x being 5 or 6, and from 1 to 4 hetero atoms selected from the group consisting of sulfur, oxygen and nitrogen, R12 and R13 are independently selected from the group consisting of hydrogen, $C_1$-$C_4$alkyl, $C_1$-$C_4$alkoxy, $C_3$-$C_7$cycloalkyloxy, $C_3$-$C_7$cycloalkyl-$C_1$-$C_4$alkoxy, halogen, halogen-substituted $C_1$-$C_4$alkyl groups, halogen-substituted $C_1$-$C_4$alkoxy groups, cyano, nitro, amino, $C_1$-$C_4$alkylamino, di($C_1$-$C_4$)alkylamino, $C_1$-$C_4$alkylthio, mercapto, hydroxy, carbamoyl, a carboxyl group, an oxo group; or when both substituents R12 and R13 are located at adjacent carbon atoms of the ring

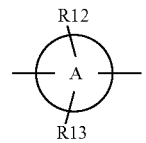

these two substituents, taken together with said adjacent carbon atoms, can also form a 5- or 6- member aromatic or a x-member saturated or unsaturated heterocycloaliphatic or heteroaromatic ring containing from 2 to (x−1) carbon atoms with x being 5 or 6, and from 1 to 4 hetero atoms selected from the group consisting of sulfur oxygen and nitrogen, and wherein V can have altogether one to four substituents of the kind as defined for R12 and R13 and the free valences can be located either on one or on both rings of the group V.

17. A compound or an acid addition salt, a N-oxide or an in vivo cleavable ester thereof according to claim 16, wherein
V is a divalent group of formula

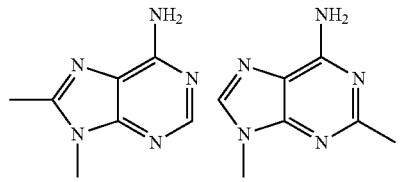

-continued

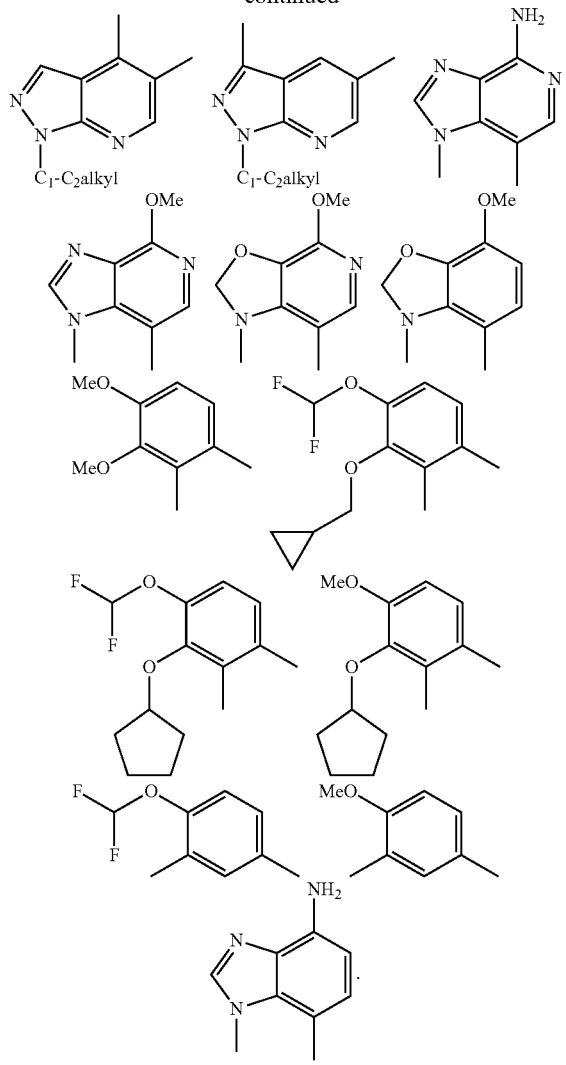

18. A compound or an acid addition salt, a N-oxide or an in vivo cleavable ester thereof according to claim 1, wherein W is heterocyclyl.

19. A compound or an acid addition salt, a N-oxide or an in vivo cleavable ester thereof according to claim 1, wherein W is a group of formula

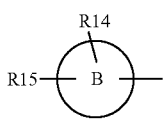

wherein

is a phenyl ring or a x-membered saturated or unsaturated heterocycloaliphatic or heteroaromatic ring containing from 2 to (x−1) carbon atoms with x being 5 or 6, and from 1 to 4 hetero atoms selected from the group consisting of sulfur, oxygen and nitrogen, R14 and R15 are independently selected from the group consisting of hydrogen, $C_1$-$C_4$alkyl, $C_1$-$C_4$alkoxy, $C_3$-$C_7$cycloalkyloxy, $C_3$-$C_7$cycloalkyl-$C_1$-$C_4$alkoxy, halogen, halogen-substituted $C_1$-$C_4$alkyl groups, halogen-substituted $C_1$-$C_4$alkoxy groups, cyano, nitro, amino, $C_1$-$C_4$alkylamino, di($C_1$-C4)alkylamino, $C_1$-$C_4$alkylthio, mercapto, hydroxy, carbamoyl, a carboxyl group, and an oxo group; or when both substituents R14 and R15 are located at adjacent carbon atoms of the ring

these two substituents, taken together with said adjacent carbon atoms, can also form a 5- or 6-membered aromatic or a x-membered saturated or unsaturated heterocycloaliphatic or heteroaromatic ring containing from 2 to (x−1) carbon atoms with x being 5 or 6, and from 1 to 3 hetero atoms selected from the group consisting of sulfur, oxygen and nitrogen, wherein W can have altogether one to four substituents of the kind as defined for R14 and R15 and the free valence can be located on either ring of the group W.

20. A compound or an acid addition salt, a N-oxide or an in vivo cleavable ester thereof according to claim 19, wherein W is a group of one of the formulae

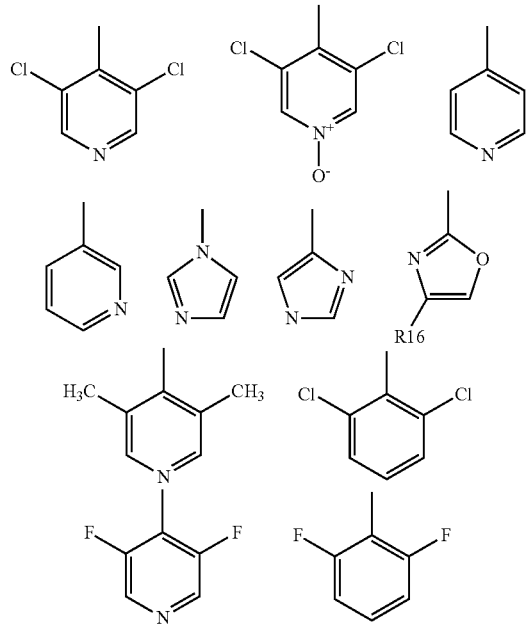

wherein R16 is hydrogen or $C_1$-$C_4$alkyl.

21. A compound or an acid addition salt, a N-oxide or an in vivo cleavable ester thereof according to claim 1, wherein Q is —NR10R11.

22. A compound or an acid addition salt, a N-oxide or an in vivo cleavable ester thereof according to claim 1, wherein
A1, A2 are independently of each other either absent or a $C_1$-$C_2$alkylene group; and
L is —NH—, —(CO)NH— or —NH(CO)— or is absent.

23. A compound or an acid addition salt, a N-oxide or an in vivo cleavable ester thereof according to claim 22, wherein A1, A2 are independently of each other either absent or a C₁-C₂alkylene group;

L is —NH—, —(CO)NH— or —NH(CO)—;

V is a divalent group of formula

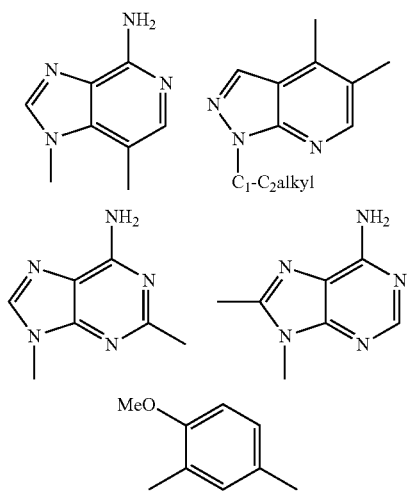

W is a group of formula

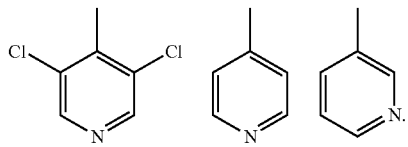

24. A compound or an acid addition salt, a N-oxide or an in vivo cleavable ester thereof according to claim 1, wherein Y is —S— and X is —CH₂—CH₂—CH₂—, —CH₂—CH₂—NH—, —CH₂—CH₂—O—, —CH₂—CH₂—CH₂—NH— or —CH₂—CH₂—CH₂—O— linked to the residue Q via the NH group or O atom respectively, or —CH₂—CH₂—.

25. A compound or an acid addition salt, a N-oxide or an in vivo cleavable ester thereof according to claim 21, wherein —NR10R11 is a group of one of the following formulae

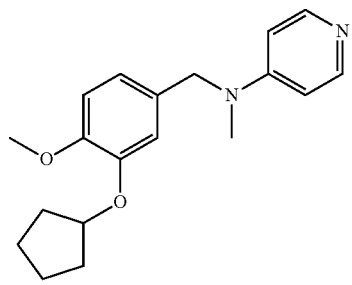

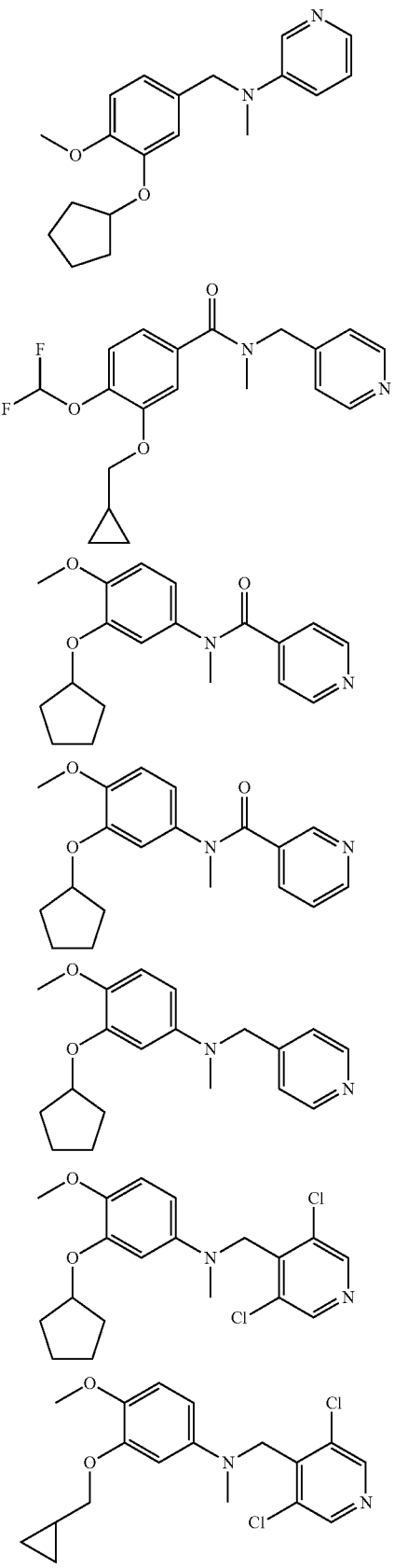

wherein
means a methoxy residue.
26. A compound or an acid addition salt, a N-oxide or an in vivo cleavable ester thereof according to claim 1 said compound having the formula
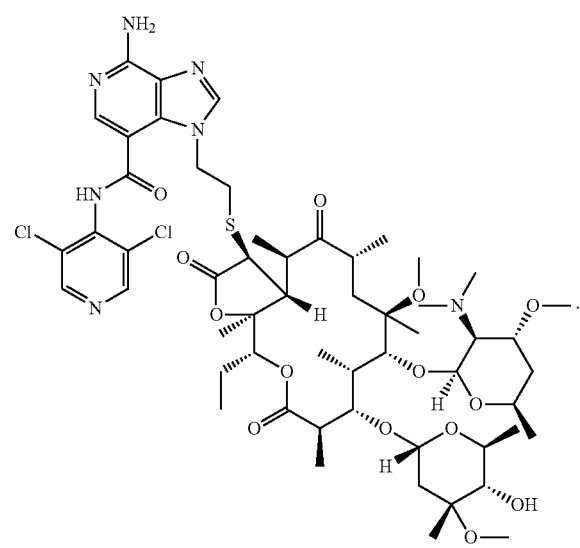 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@@H](OC)[C@@H]2N(C)C)[C@](C)(OC)C[C@@H](C)C(=O)[C@H](C)[C@H]2[C@H](SCCn3cnc4c(N)ncc(C(=O)Nc5c(Cl)cncc5Cl)c43)C(=O)O[C@@]21C]
27. A compound or an acid addition salt, a N-oxide or an in vivo cleavable ester thereof according to claim 1, said compound having one of the following formulae:
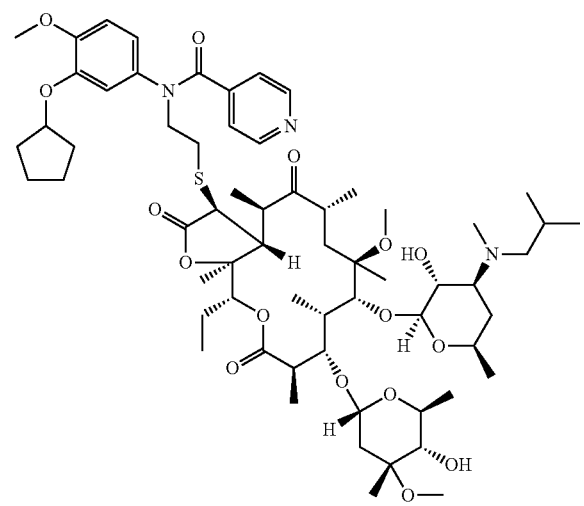
-continued
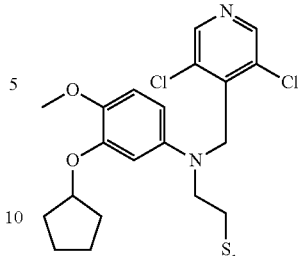
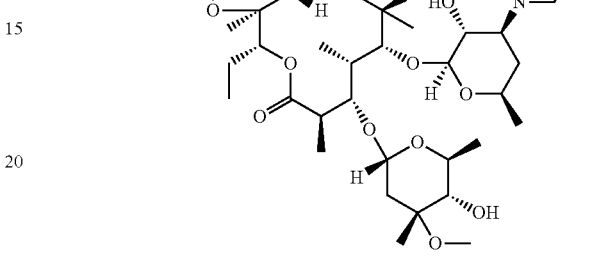
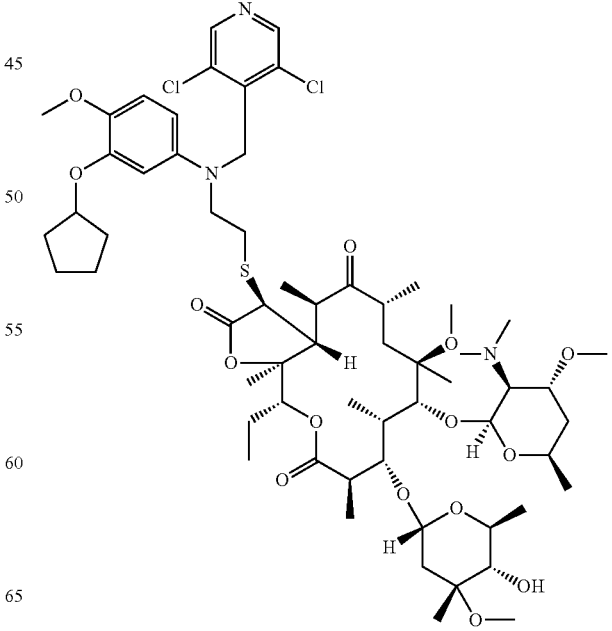

-continued

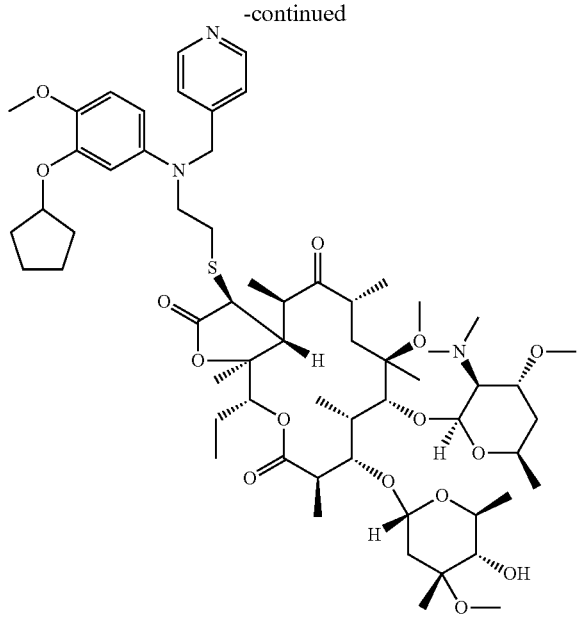
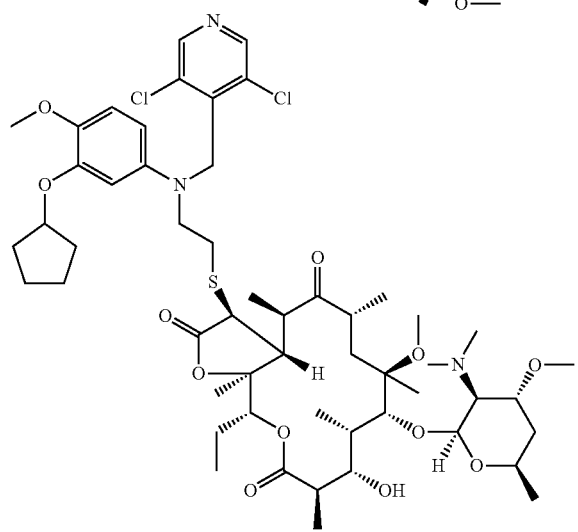
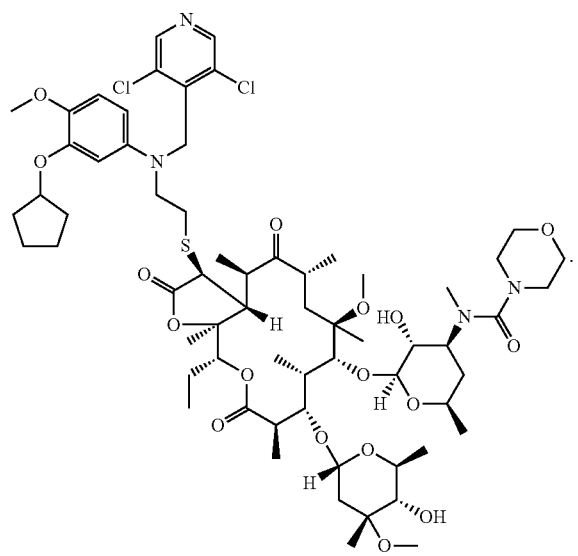

28. An in vivo cleavable ester of a compound according to claim 1, which is an ester of the 2'-hydroxy group of the sugar moiety.

29. An ester of a compound according to claim 1 which is an acetate ester, pivaloyl ester, tartrate ester, maleate ester or succinate ester.

30. The macrolide compound of claim 1, wherein said macrolide compound is an N oxide.

31. A medicament comprising a compound or an acid addition salt, a N-oxide or an in vivo cleavable ester thereof according to claim 1 and a pharmaceutically acceptable carrier.

32. A medicament according to claim 31 for use for treatment of inflammatory or allergic diseases or cancer, in said subject selected from an animal and a human.

33. A medicament according to claim 31 for use for the treatment of asthma, chronic bronchitis, emphysema, atopic dermatitis, urticaria, allergic rhinitis, allergic conjunctivitis, psoriasis, rheumatoid arthritis, chronic obstructive pulmonary disease (COPD), septic shock, ulcerative colitis, inflammatory bowel disease, e.g. Crohn's disease, adult respiratory distress syndrome or multiple sclerosis.

34. A medicament according to claim 31 for use for the treatment of chronic obstructive pulmonary disease (COPD), asthma, rheumatoid arthritis, psoriasis or atopic dermatitis.

35. A compound according to claim 1 or an acid addition salt, a N-oxide or an in vivo cleavable ester thereof for use for the treatment of inflammatory or allergic diseases or cancer in a subject selected from an animal and a human.

36. A method for treating an inflammatory or allergic disease or cancer in a subject selected from an animal and a human, in need of such treatment wherein an amount of a compound according to claim 1 or an acid addition salt, a N-oxide or an in vivo cleavable ester thereof which amount is effective in treating said inflammatory or allergic disease or said cancer disease is administered to said subject.

37. A method for treating a human affected by a disorder or disease which can be ameliorated by inhibition of human phosphodiesterases, wherein an amount of a compound according to claim 1 or an acid addition salt, a N-oxide or an in vivo cleavable ester thereof is administered to said human which amount is effective for ameliorating said disorder or disease, wherein said disorder or disease is an inflammatory or allergic disease or disorder or cancer.

38. A process for the manufacture of a compound of formula (I) according to claim 1, comprising
a) converting a macrolide compound having the formula (II)

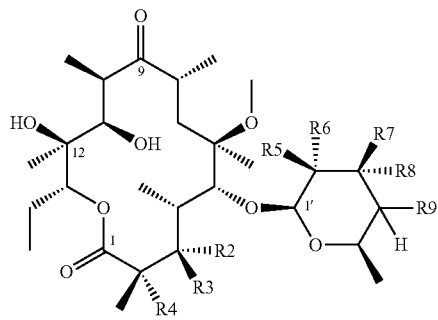

wherein the groups R2 to R9 are defined as in claim 1, after appropriate protection where necessary, in a manner known per se to a compound of formula IV

IV

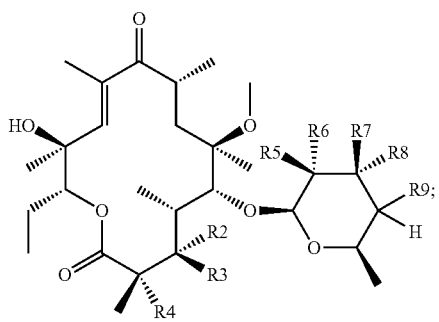

b) converting said compound of formula IV in a manner known per se to a compound of formula VI

VI

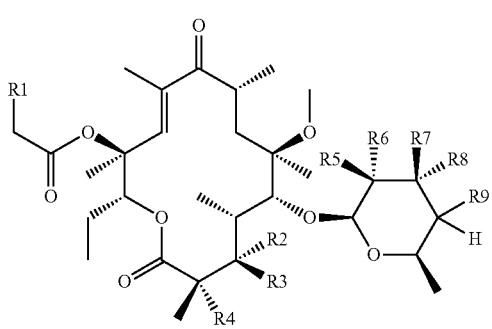

wherein R1 is as defined in claim 1 or is a group of formula —S-Rp$_3$ wherein Rp$_3$ is a sulfur protecting group, c) reacting said compound of formula VI in an aprotic solvent with an alkali metal base to form a compound of formula VII

VII

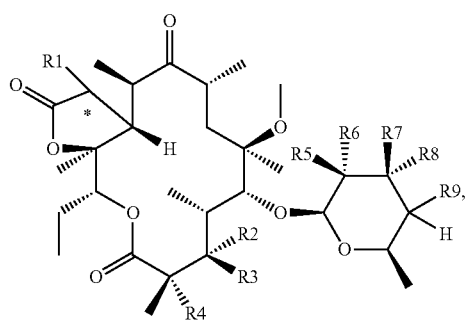

wherein R1 to R9 have the meaning above, and removing any protecting groups where necessary to form the compound of formula I, with the proviso that in case that R1 is S-Rp$_3$ the compound of formula VII is transformed into the disulfide derivative of formula VIII, in the presence of a molecular sieve if R2 represents a cladinosyl group, before removing the hydroxyl protecting groups Rp$_1$ and Rp$_2$

VIII

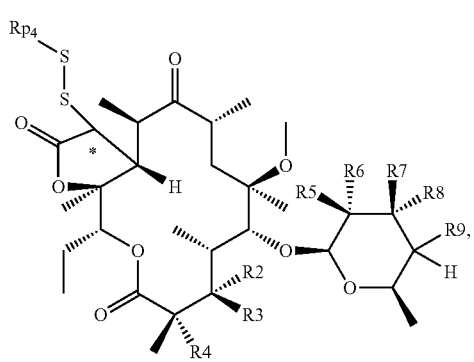

wherein Rp$_4$ is C$_1$-C$_4$alkyl, in particular methyl, or 3-nitro-2-pyridinyl, which compound is treated with a reducing agent, in particular trialkyl phosphine or triaryl phosphine, in a solvent, in particular aqueous acetone, aqueous DMF, aqueous dioxane or aqueous THF, to give a compound of formula IX

IX

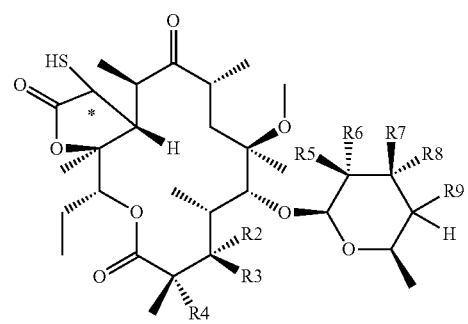

wherein R2 to R9 have the above meaning, which compound is then reacted with a compound of formula Q-X-Lg, wherein Q and X are as defined in claim 1 and Lg is a leaving group or, when X represents a carbonyl or sulfonyl group, a vinyl group, to give the compound of formula VII wherein R1 is as defined in claim 1.

39. A process for the manufacture of a compound of formula I according to claim 1, comprising converting a compound selected from the compounds of the formulae

I-1

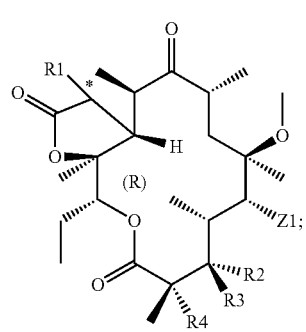

151
-continued

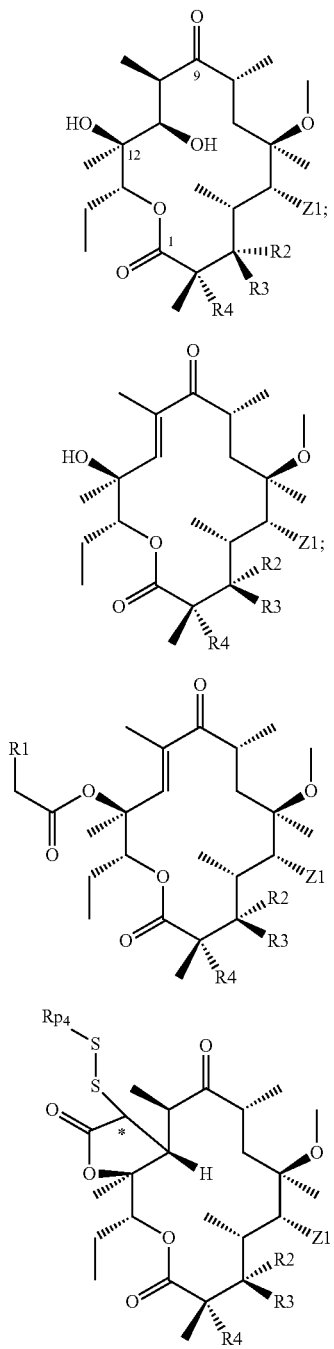

II-1

IV-1

VI-1 and

VIII-1 wherein
R1, R2, R3 and R4 have on of the meanings as defined in claim 1 and
Z1 is a group of formula

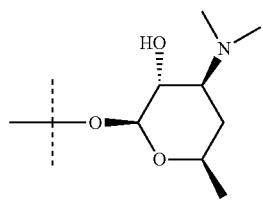

152 wherein

represents the bond between said group and the carbon atom of said macrolide compound to which it is linked;

in a manner known per se to the compound of formula (I) according to claim 1.

40. A process according to claim 39 wherein the compounds of formula (I-1); (II-1); (IV-1); (VI-1) or (VII-1) are obtained according to the following process scheme:

a) converting a macrolide compound having the formula (II-1)

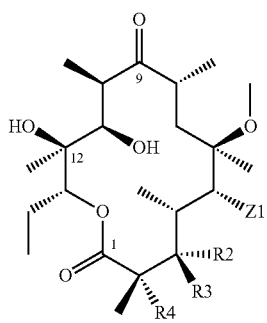

II-1 wherein the groups R2 to R4 and Z1 are defined as in claim 37, after appropriate protection where necessary, in a manner known per se to the corresponding compound of formula (IV-1)

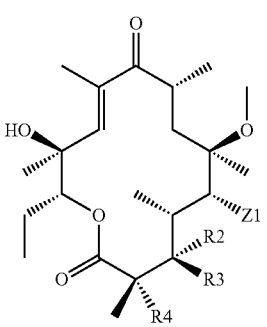

IV-1 b) converting said compound of formula (IV-1) in a manner known per se to the corresponding compound of formula (VI-1)

VI-1

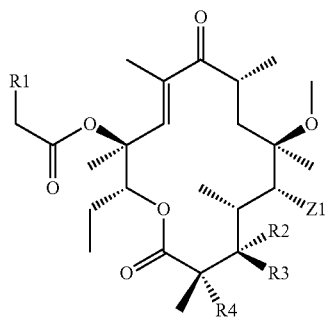

wherein R1 is as defined in claim 1 or is a group of formula —S-Rp$_3$ wherein Rp$_3$ is a sulfur protecting group,
c) reacting said compound of formula (VI-1) in an aprotic solvent with an alkali metal base to form the corresponding compound of formula (VII-1)

VII-1

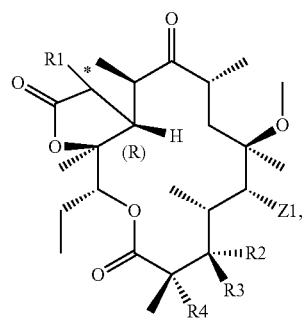

and removing any protecting groups where necessary to foils the compound of formula (I-1), or, in case that R1 is S-Rp$_3$, the compound of formula (VII-1) is transformed into the disulfide derivative of formula (VIII-1), in the presence of a molecular sieve if R2 represents a cladinosyl group, before removing any hydroxyl protecting groups

VIII-1

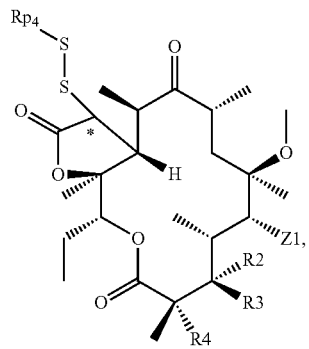

wherein Rp$_4$ is C$_1$-C$_4$alkyl, in particular methyl, or 3-nitro-2-pyridinyl, and the compound of formula (I-1); (II-1); (IV-1); (VI-1) or (VIII-1) are processed according to claim 39.

41. A compound or an acid addition salt, a N-oxide or an in vivo cleavable ester thereof according to claim 1, wherein in Z,
R7 is —NR7bR7c selected from the group consisting of

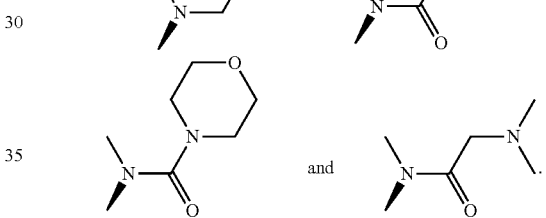

42. The compound or an acid addition salt, a N-oxide or an in vivo cleavable ester thereof of claim 41, wherein R6 is hydroxyl.

* * * * *